US012709752B2

(12) United States Patent
Ostriker et al.

(10) Patent No.: US 12,709,752 B2
(45) Date of Patent: Aug. 18, 2026

(54) COMPOSITIONS AND METHODS FOR INHIBITING XDH EXPRESSION

(71) Applicant: NOVO NORDISK A/S, Bagsværd (DK)

(72) Inventors: Allison Cherry Ostriker, Lexington, MA (US); Martin Lee Koser, Westford, MA (US)

(73) Assignee: NOVO NORDISK A/S, Bagsværd (DK)

( * ) Notice: Subject to any disclaimer, the term of this patent is extended or adjusted under 35 U.S.C. 154(b) by 0 days.

(21) Appl. No.: 19/306,057

(22) Filed: Aug. 21, 2025

(65) Prior Publication Data

US 2026/0055414 A1 Feb. 26, 2026

Related U.S. Application Data

(60) Provisional application No. 63/685,395, filed on Aug. 21, 2024.

(51) Int. Cl.
*C07H 21/02* (2006.01)
*C07H 21/04* (2006.01)
*C12N 15/113* (2010.01)

(52) U.S. Cl.
CPC .. *C12N 15/1137* (2013.01); *C12Y 117/01004* (2013.01); *C12N 2310/14* (2013.01); *C12N 2310/315* (2013.01); *C12N 2310/321* (2013.01); *C12N 2310/351* (2013.01)

(58) Field of Classification Search
CPC .......................... C12N 15/113; C12N 2310/14
See application file for complete search history.

(56) References Cited

U.S. PATENT DOCUMENTS 7,491,805 B2 2/2009 Vargeese et al.
7,645,747 B2 1/2010 Boojamra et al.
7,696,345 B2 4/2010 Allerson et al.
7,750,144 B2 7/2010 Zamore et al.
7,786,290 B2 8/2010 Woppmann et al.
7,923,547 B2 4/2011 McSwiggen et al.
8,084,598 B1 12/2011 Bentwich
8,084,599 B2 12/2011 Rossi et al.
8,273,866 B2 9/2012 McSwiggen et al.
8,334,373 B2 12/2012 Vornlocher et al.
8,513,207 B2 8/2013 Brown
8,779,114 B2 7/2014 Han et al.
8,877,917 B2 11/2014 Forst et al.
8,883,996 B2 11/2014 Rossi et al.
8,927,513 B2 1/2015 Manoharan et al.
8,927,705 B2 1/2015 Brown
8,987,435 B2 3/2015 Swayze et al.
8,993,532 B2 3/2015 Hannon et al.
9,012,138 B2 4/2015 Tuschl et al.
9,012,621 B2 4/2015 Tuschl et al.
9,074,213 B2 7/2015 Kreutzer et al.
9,193,753 B2 11/2015 Tuschl et al.
9,222,091 B2 12/2015 Manoharan et al.
9,260,471 B2 2/2016 Cancilla et al.
9,320,798 B2 4/2016 Brown
9,326,941 B2 5/2016 Chae et al.
9,328,345 B2 5/2016 Li et al.
9,549,983 B2 1/2017 Brown et al.
9,771,583 B2 9/2017 Puri et al.
9,790,498 B2 10/2017 Brown et al.
9,943,604 B2 4/2018 Seth et al.
10,144,725 B2 12/2018 Brown
10,487,330 B2 11/2019 Brown et al.
10,676,742 B2 6/2020 Brown et al.
10,876,119 B2 12/2020 Khvorova et al.
11,326,166 B1 5/2022 Mclninch et al.
11,414,659 B2 8/2022 Wang et al.
11,504,391 B1 11/2022 Schlegel et al.
11,674,141 B2 6/2023 Yokota et al.
11,873,488 B2 1/2024 Wang et al.
2008/0317839 A1 12/2008 Quay et al.
2009/0023675 A1 1/2009 McSwiggen et al.
2009/0176725 A1 7/2009 Morrissey et al.
2009/0220587 A1 9/2009 Allon et al.
2009/0285881 A1 11/2009 Dande et al.
2010/0055168 A1 3/2010 Dande et al.
2010/0063135 A1 3/2010 Dande et al.
2010/0173973 A1 7/2010 Brown
2010/0173974 A1 7/2010 Brown
2010/0197023 A1 8/2010 Leake et al.
2010/0204305 A1 8/2010 Young et al.
2011/0110972 A1 5/2011 Vasievich et al.
2011/0111056 A1 5/2011 Basu et al.
2011/0118340 A1 5/2011 Manoharan et al.
(Continued)

FOREIGN PATENT DOCUMENTS

CA 2677068 A1 3/2011
CA 3209281 A1 * 9/2022 .......... C12N 15/113
(Continued)

OTHER PUBLICATIONS

Elbashir et al. (The EMBO Journal, vol. 20, No. 23, pp. 6877-6888, 2001).*
Zhang et al. (Biologia Plantarum, 57(3), 547-554, 2013).*
Wang et al. (Hindawi Publishing Corporation, Mediators of Inflammation, vol. 2015, Article ID 680853, 1-6).*
Sliva et al. (e Virology Journal 2010, 7:248, 1-11).*
McIntyre et al. (BMC Molecular Biology 2011, 12:34, 1-12).*
Antao et al., "A thermodynamic study of unusually stable RNA and DNA hairpins", Nucleic Acid Research, 1991, vol. 19, No. 21, pp. 5901-5905.
Cheong et al., "Solution structure of an unusually stable RNA hairpin, 5GGAC(UUCG)GUCC", Nature, Aug. 1990, vol. 346, pp. 680-682.
(Continued)

*Primary Examiner* — Amy Rose Hudson
(74) *Attorney, Agent, or Firm* — Novo Nordisk A/S

(57) ABSTRACT

Oligonucleotides are provided herein that inhibit XDH expression. Also provided are compositions including the same and uses thereof, particularly uses relating to treating diseases, disorders and/or conditions associated with aberrant XDH expression.

5 Claims, 10 Drawing Sheets

Specification includes a Sequence Listing.

(56) References Cited

U.S. PATENT DOCUMENTS

| | | | |
|---|---|---|---|
| 2011/0288147 | A1 | 11/2011 | Brown |
| 2012/0095200 | A1 | 4/2012 | Brown |
| 2012/0121515 | A1 | 5/2012 | Dang et al. |
| 2013/0338210 | A1 | 12/2013 | Manoharan et al. |
| 2015/0203847 | A1 | 7/2015 | Manoharan et al. |
| 2015/0265708 | A1 | 9/2015 | Manoharan et al. |
| 2019/0002880 | A1 | 1/2019 | Woolf et al. |
| 2019/0151461 | A1 | 5/2019 | Brown et al. |
| 2019/0177729 | A1 | 6/2019 | Wang et al. |
| 2020/0031862 | A1 | 1/2020 | Brown et al. |
| 2020/0270605 | A1 | 8/2020 | Khvorova et al. |
| 2021/0388358 | A1 | 12/2021 | Brown |
| 2022/0125823 | A1 | 4/2022 | Nair et al. |
| 2022/0135972 | A1 | 5/2022 | Yokota et al. |
| 2022/0170025 | A1 | 6/2022 | Brown et al. |
| 2022/0177880 | A1 | 6/2022 | Brown et al. |
| 2022/0307024 | A1 | 9/2022 | Nair et al. |
| 2022/0389430 | A1 | 12/2022 | Wang et al. |
| 2022/0411801 | A1 | 12/2022 | McIninch et al. |
| 2023/0002773 | A1 | 1/2023 | Nicholas et al. |
| 2023/0069235 | A1 | 3/2023 | Brown et al. |
| 2023/0089478 | A1 | 3/2023 | Cardia et al. |
| 2023/0110876 | A1 | 4/2023 | Maier et al. |
| 2023/0123981 | A1 | 4/2023 | Wang et al. |
| 2023/0277675 | A1 | 9/2023 | Wang et al. |
| 2023/0287424 | A1 | 9/2023 | Brown et al. |
| 2024/0287512 | A1 | 8/2024 | Grim et al. |
| 2024/0287513 | A1 | 8/2024 | Rigo et al. |
| 2024/0360455 | A1 | 10/2024 | Nair et al. |
| 2025/0163097 | A1 | 5/2025 | Komisarski et al. |

FOREIGN PATENT DOCUMENTS

| | | | |
|---|---|---|---|
| EP | 2513334 | A1 | 10/2012 |
| EP | 2774989 | A1 | 9/2014 |
| EP | 2280070 | B1 | 5/2015 |
| EP | 3503730 | A1 | 7/2019 |
| EP | 4021915 | A1 | 7/2022 |
| EP | 4225919 | A1 | 8/2023 |
| EP | 4284933 | A1 | 12/2023 |
| EP | 4392556 | A1 | 7/2024 |
| EP | 4430 190 | A2 | 9/2024 |
| EP | 4426839 | A1 | 9/2024 |
| EP | 4493568 | A1 | 1/2025 |
| WO | WO-2004/045543 | A2 | 6/2004 |
| WO | WO-2009/129385 | A1 | 10/2009 |
| WO | WO-2010/030730 | A1 | 3/2010 |
| WO | WO-2010/033225 | A2 | 3/2010 |
| WO | WO-2010/054405 | A1 | 5/2010 |
| WO | WO-2010/141726 | A2 | 12/2010 |
| WO | WO-2011/005860 | A2 | 1/2011 |
| WO | WO-2011/022460 | A1 | 2/2011 |
| WO | WO-2011/072292 | A2 | 6/2011 |
| WO | WO-2011/075188 | A1 | 6/2011 |
| WO | WO-2011/075656 | A1 | 6/2011 |
| WO | WO-2011/123621 | A2 | 10/2011 |
| WO | WO-2011/133871 | A2 | 10/2011 |
| WO | WO-2012/000104 | A1 | 1/2012 |
| WO | WO-2012/030683 | A2 | 3/2012 |
| WO | WO-2013/032643 | A2 | 3/2013 |
| WO | WO-2013/033230 | A1 | 3/2013 |
| WO | WO-2013/074974 | A2 | 5/2013 |
| WO | WO-2013/165816 | A2 | 11/2013 |
| WO | WO-2015/069932 | A1 | 5/2015 |
| WO | WO-2015/085158 | A1 | 6/2015 |
| WO | WO-2015/106128 | A2 | 7/2015 |
| WO | WO-2016/028649 | A1 | 2/2016 |
| WO | WO-2016/100401 | A1 | 6/2016 |
| WO | WO-2016/149020 | A1 | 9/2016 |
| WO | WO-2016/149313 | A1 | 9/2016 |
| WO | WO-2016/168286 | A1 | 10/2016 |
| WO | WO-2018/039364 | A1 | 3/2018 |
| WO | WO-2018/045317 | A1 | 3/2018 |
| WO | WO-2018/185241 | A1 | 10/2018 |
| WO | WO-2019/200124 | A1 | 10/2019 |
| WO | WO-2019/217459 | A1 | 11/2019 |
| WO | WO-2019/232255 | A1 | 12/2019 |
| WO | WO-2020/123083 | A1 | 6/2020 |
| WO | WO-2020/132227 | A2 | 6/2020 |
| WO | WO-2020/206350 | A1 | 10/2020 |
| WO | WO-2020/226960 | A1 | 11/2020 |
| WO | WO-2020/257194 | A1 | 12/2020 |
| WO | WO-2021/067744 | A1 | 4/2021 |
| WO | WO-2021/146488 | A1 | 7/2021 |
| WO | WO-2022/187622 | A1 | 9/2022 |
| WO | WO-2022/269346 | A2 | 12/2022 |
| WO | WO-2022/271573 | A1 | 12/2022 |
| WO | WO-2023/081822 | A1 | 5/2023 |
| WO | WO-2023/245061 | A2 | 12/2023 |
| WO | WO-2024/040041 | A1 | 2/2024 |
| WO | WO-2024/073709 | A2 | 4/2024 |
| WO | WO-2024/216155 | A1 | 10/2024 |
| WO | WO-2024/233864 | A2 | 11/2024 |
| WO | WO-2024/249680 | A2 | 12/2024 |
| WO | WO-2025/054459 | A1 | 3/2025 |

OTHER PUBLICATIONS

Cornish-Bowden, "Nomenclature for incompletely specified bases in nucleic acid sequences: recommendations 1984", Nucleic Acids Res., May 1985, vol. 13, No. 9, pp. 3021-3030.

Heus et al., "Structural Features That Give Rise to the Unusual Stability if RNA Hairpins Containing GNRA Loops", Science, 1991, vol. 253, pp. 191-194.

Huch et al., "In vitro expansion of single Lgr5+ liver stem cells induced by Wnt-driven regeneration", Nature, Feb. 2013, vol. 494, pp. 247-250.

Imanishi et al., "BNAs: novel nucleic acid analogs with a bridged sugar moiety", Chem Commun. (Camb), Aug. 2002, vol. 21, pp. 1653-1659.

Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition", Tetrahedon, Apr. 1998, vol. 54, pp. 3607-3630.

Nakano et al., "Selection for thermodynamically stable DNA tetraloops using temperature gradient gel electrophoresis reveals four motifs: d(cGNNAg), d(cGNABg), d(cCNNGg), and d(gCNNGc)", Biochemistry, Dec. 2002, vol. 41, pp. 14281-92.

Prakash et al., "Identification of metabolically stable 5'-phosphate analogs that support single- stranded siRNA activity", Nucleic Acids Res., Mar. 2015, vol. 43, pp. 2993-3011.

Shinji et al., Nippon Kagakkai Koen Yokoshu, 2000, vol. 78, p. 731.

Snead et al., "5' Unlocked Nucleic Acid Modification Improves siRNA Targeting", Mol. Ther-Nucl. Acids, Jul. 2013, vol. 2, No. 7, e103, pp. 1-7.

Woese et al., "Architecture of ribosomal RNA: constraints on the sequence of "tetra-loops"", PNAS, Nov. 1990, vol. 87, pp. 8467-8471.

Allerson et al., "Fully 2'-Modified Oligonucleotide Duplexes with Improved in Vitro Potency and Stability Compared to Unmodified Small Interfering RNA", Journal of Medicinal Chemistry, vol. 48, No. 4, Jan. 20, 2005, pp. 901-904.

Biscans et al., "The valency of fatty acid conjugates impacts siRNA pharmacokinetics, distribution, and efficacy in vivo". Journal of controlled release. May 28, 2019; 302: 116-25. Epub Mar. 30, 2019.

Bottaro et al., "Mapping the Universe of RNA Tetraloop Folds", Biophysical Journal, 2017, vol. 113, pp. 257-267.

Chang et al., "Asymmetric shorter-duplex siRNA structures trigger efficient gene silencing with reduced nonspecific effects", Mol Ther. Apr. 2009;17(4):725-32.

Chernikov et al., "Current Development of siRNA Bioconjugates: From Research to the Clinic," Front Pharmacol. 2019;10:444.

Dicerna Pharmaceuticals, Inc., "Taking RNAi under the skin," Nature.com. 2016:B12; Retrieved from the Internet: https://media.nature.com/original/magazine-assets/d43747-020-00189-y/d43747-020-00189-y.pdf.

Foster, et al., "Advanced siRNA Designs Further Improve In Vivo Performance of GalNAc-siRNA Conjugates", Molecular Therapy, vol. 26, No. 3, Mar. 2018, pp. 708-717.

(56) References Cited

OTHER PUBLICATIONS

Hall, “Mighty tiny”, RNA, Apr. 1, 2015, vol. 21, pp. 630-631.
Kenski, et al., “siRNA-optimized Modifications for Enhanced In Vivo Activity”, Molecular Therapy-Nucleic Acids, vol. 1, e5, Jan. 24, 2012, pp. 1-8.
Koizumi, M., “Nucleic acids therapeutics using chemical modified oligonucleotides,”. Medchem News, vol. 25, No. 2, May 1, 2015, pp. 103-108.
Kubo et al., “Lipid-Conjugated 27-Nucleotide Double-Stranded RNAs with Dicer-Substrate Potency Enhance RNAi-Mediated Gene Silencing”, Molecular Pharmaceuticals, May 7, 2012, vol. 9, No. 5, pp. 1374-1382.
Leonard et al., “Effects of osmolytes and macromolecular crowders on stable GAAA tetraloops and their preference for a CG closing base pair”, PeerJ, 2018, 6:e4236; DOI 10.7717/peerj.4236, 16 pages.
Mikula, H.; Svatunek, D.; Lumpi, D.; Glocklhofer, F.; Hametner, Frolich, DMDO preparation and glycal epoxidation, J. Org, Process Res. Dev. 2013, 17, 313-316.
Minikel, “Antisense part III: chemistries,” CureFFI.org, Comparison of Chemical Modifications, Aug. 28, 2018, 16 Pages.
Nair, et al., “Impact of Enhanced Metabolic Stability on Pharmacokinetics and Pharmacodynamics of GalNAc—siRNA Conjugates”, Nucleic Acids Research, vol. 45, No. 19, Published online Sep. 15, 2017, pp. 10969-10977, pp. 1-11.
Podbevsek et al., “Solution-state structure of a fully alternately 2'-F/2'-OMe modified 42-nt dimeric siRNA construct,” Nucleic Acids Res. Nov. 2010;38(20):7298-307.
Zhou et al., “Current RNA-based Therapeutics in Clinical Trials,” Curr Gene Ther. 2019;19(3):172-196.
International Search Report and Written Opinion for International Application No. PCT/IB25/00418 dated Feb. 20, 2026.

* cited by examiner

COMPOSITIONS AND METHODS FOR INHIBITING XDH EXPRESSION

CROSS-REFERENCE TO RELATED APPLICATIONS

This application claims the benefit of U.S. Provisional Patent Application Ser. No. 63/685,395 filed Aug. 21, 2024, which is incorporated by reference herein in its entirety.

REFERENCE TO AN ELECTRONIC SEQUENCE LISTING

The application contains a Sequence Listing which has been submitted electronically in .XML format and is hereby incorporated by reference in its entirety. Said .XML copy, created on Aug. 19, 2025, is named "DCY-13401.xml" and is 360,197 bytes in size. The sequence listing contained in this .XML file is part of the specification and is hereby incorporated by reference herein in its entirety.

BACKGROUND

Chronic hyperuricemia is linked to various diseases, including gout. Gout results from an inflammatory response to uric acid crystals in joints due to inadequate renal clearance or excessive production of uric acid. Uric acid, the final product of purine metabolism, is produced by the oxidation of hypoxanthine to xanthine and then to uric acid, catalyzed by xanthine oxidase (XO) and xanthine dehydrogenase (XDH). These enzymes, primarily expressed in the intestine and liver, are interconvertible forms of the same molybdopterin-containing flavoprotein. Strategies for targeting the XDH gene to prevent diseases associated with chronic hyperuricemia are needed.

SUMMARY OF DISCLOSURE

In some aspects, the disclosure provides a composition comprising a first RNA oligonucleotide and a second RNA oligonucleotide, wherein the first RNA oligonucleotide comprises the sequence set forth in SEQ ID: 23, and the second RNA oligonucleotide comprises the sequence set forth in SEQ ID: 24. In some embodiments, the first RNA oligonucleotide consists of the sequence set forth in SEQ ID: 23. In some embodiments, the second RNA oligonucleotide consists of the sequence set forth in SEQ ID: 24.

In some aspects, the disclosure provides a composition comprising a first RNA oligonucleotide and a second RNA oligonucleotide, wherein the first RNA oligonucleotide comprises the sequence set forth in SEQ ID: 21, and the second RNA oligonucleotide comprises the sequence set forth in SEQ ID: 22. In some embodiments, the first and second RNA oligonucleotides each comprise at least one modified nucleotide.

In some aspects, the disclosure provides a pharmaceutical composition comprising a composition described herein and a pharmaceutically acceptable carrier, delivery agent or excipient.

In some aspects, the disclosure provides a pharmaceutical composition comprising a first oligonucleotide and a second RNA oligonucleotide described herein and a pharmaceutically acceptable carrier, delivery agent or excipient.

In some aspects, the disclosure provides a method of treating a disease associated with chronic hyperuricemia in a subject in need thereof, the method comprising administering to the subject a composition or pharmaceutical composition described herein. In some embodiments, the disease associated with chronic hyperuricemia is gout.

In some aspects, the disclosure provides a method of treating a disease associated with gout in a subject in need thereof, the method comprising administering to the subject a composition or pharmaceutical composition described herein.

In some aspects, the disclosure provides a method for reducing XDH expression in a subject in need thereof, the method comprising administering to the subject a composition or pharmaceutical composition described herein.

In some aspects, the disclosure provides a method for reducing XDH expression in a cell, the method comprising contacting the cell with a composition or pharmaceutical composition described herein.

DETAILED DESCRIPTION

Figure 1A:
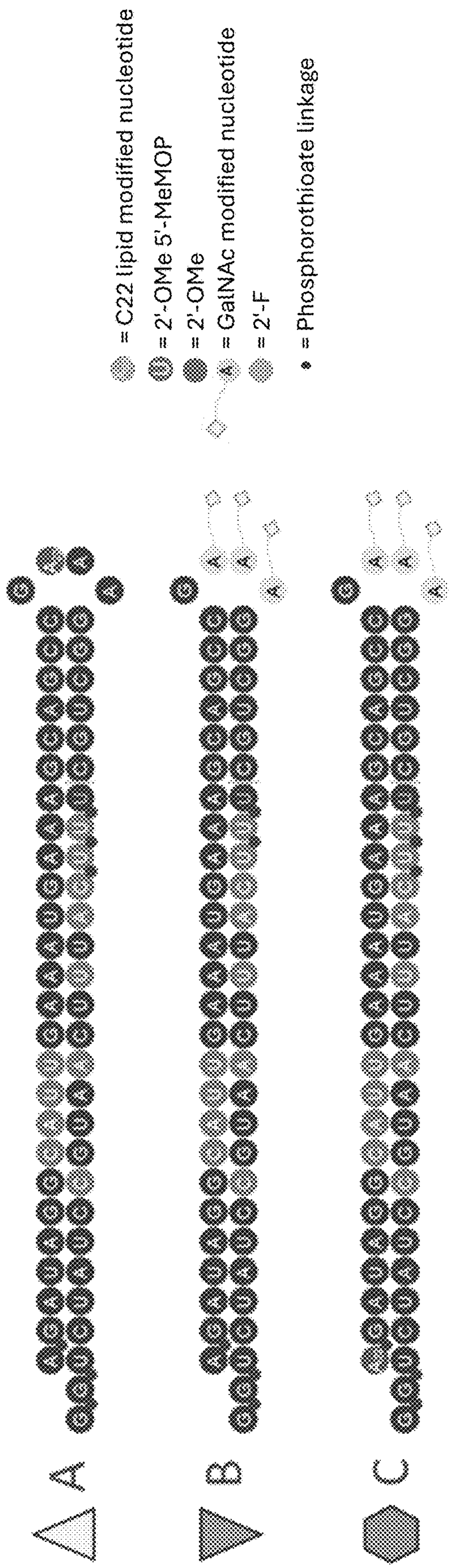
FIG. 1A provides schematics of RNAi oligonucleotide molecules targeting xanthine dehydrogenase (XDH) and conjugated to (i) a C22 hydrocarbon chain lipid at a nucleotide of the tetraloop (top), the RNAi oligonucleotide molecule comprising a sense strand and antisense strand having of the sequences of SEQ ID NOs: 30 and 31, respectively, (ii) a GalNAc molecule at three nucleotides of the tetraloop (middle), the RNAi oligonucleotide molecule comprising a sense strand and antisense strand having of the sequences of SEQ ID NOs: 32 and 33, respectively, and (iii) a C22 hydrocarbon chain lipid at the 5' nucleotide of the sense strand and a GalNAc molecule at three nucleotides of the tetraloop (bottom) ("dual C22/GalNAc-conjugated"), the RNAi oligonucleotide molecule comprising a sense strand and antisense strand having of the sequences of SEQ ID NOs: 34 and 35, respectively.

Xanthine dehydrogenase (XDH) is an enzyme linked to various diseases and disorders, collectively termed "XDH-associated diseases". These conditions, including hyperuricemia and gout, are associated with elevated serum uric acid levels and may benefit from reduced XDH gene expression or protein activity According to some aspects, the disclosure provides oligonucleotides (e.g., RNAi oligonucleotides) that reduce XDH expression in the liver. In some embodiments, the oligonucleotides provided herein are designed to treat diseases associated with XDH expression in the liver. In some respects, the disclosure provides methods of treating a disease associated with overall XDH expression by reducing XDH expression in specific cells (e.g., cells of the liver) or in organs (e.g., liver).

Oligonucleotide Inhibitors of XDH Expression

XDH Target Sequences

In some embodiments, an oligonucleotide herein (e.g., an RNAi oligonucleotide) is targeted to a target sequence comprising an XDH mRNA. In some embodiments, an oligonucleotide described herein is targeted to a target sequence within an XDH mRNA sequence. In some embodiments, the oligonucleotide described herein corresponds to a target sequence within an XDH mRNA sequence. In some embodiments, the oligonucleotide, or a portion, fragment, or strand thereof (e.g., an antisense strand or a guide strand of a double-stranded (ds) RNAi oligonucleotide) binds or anneals to a target sequence comprising XDH mRNA, thereby inhibiting XDH expression.

Through examination of the nucleotide sequence of mRNAs encoding XDH, including mRNAs of multiple different species (e.g., human, cynomolgus monkey, and mouse) and as a result of in vitro and in vivo testing (see, e.g., Examples 1-3), it has been discovered that certain nucleotide sequences of XDH mRNA are more amenable than others to oligonucleotide-based inhibition and are thus useful as target sequences for the oligonucleotides herein. In some embodiments, a sense strand of an oligonucleotide (e.g., an RNAi oligonucleotide) described herein comprises an XDH target sequence. In some embodiments, a portion or region of the sense strand of an oligonucleotide described herein (e.g., an RNAi oligonucleotide) comprises an XDH target sequence.

XDH Targeting Sequences

In some embodiments, the oligonucleotides herein (e.g., RNAi oligonucleotides) have regions of complementarity to XDH mRNA (e.g., within a target sequence of XDH mRNA) for purposes of targeting the XDH mRNA in cells and inhibiting and/or reducing XDH expression. In some embodiments, the oligonucleotides herein comprise an XDH targeting sequence (e.g., an antisense strand or a guide strand of an RNAi oligonucleotide) having a region of complementarity that binds or anneals to an XDH target sequence by complementary (Watson-Crick) base pairing. The targeting sequence or region of complementarity is generally of a suitable length and base content to enable binding or annealing of the oligonucleotide (or a strand thereof) to an XDH mRNA for purposes of inhibiting and/or reducing XDH expression. In some embodiments, the targeting sequence or region of complementarity is at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29 or at least about 30 nucleotides in length. In some embodiments, the targeting sequence or region of complementarity is about 12 to about 30 (e.g., 12 to 30, 12 to 22, 15 to 25, 17 to 21, 18 to 27, 19 to 27, or 15 to 30) nucleotides in length. In some embodiments, the targeting sequence or region of complementarity is about 12, 13, 14, 15, 16, 17, 18, 19, 20, 21, 22, 23, 24, 25, 26, 27, 28, 29 or 30 nucleotides in length. In some embodiments, the targeting sequence or region of complementarity is 18 nucleotides in length. In some embodiments, the targeting sequence or region of complementarity is 19 nucleotides in length. In some embodiments, the targeting sequence or region of complementarity is 20 nucleotides in length. In some embodiments, the targeting sequence or region of complementarity is 21 nucleotides in length. In some embodiments, the targeting sequence or region of complementarity is 22 nucleotides in length. In some embodiments, the targeting sequence or region of complementarity is 23 nucleotides in length. In some embodiments, the targeting sequence or region of complementarity is 24 nucleotides in length.

In some embodiments, an oligonucleotide herein (e.g., an RNAi oligonucleotide) comprises a targeting sequence or a region of complementarity (e.g., an antisense strand or a guide strand of a double-stranded oligonucleotide) that is fully complementary to an XDH target sequence. In some embodiments, the targeting sequence or region of complementarity is partially complementary to an XDH target sequence. In some embodiments, the oligonucleotide comprises a targeting sequence or region of complementarity that is fully complementary to an XDH target sequence. In some embodiments, the oligonucleotide comprises a targeting sequence or region of complementarity that is partially complementary to an XDH target sequence. In some embodiments, an oligonucleotide herein (e.g., an RNAi oligonucleotide) comprises a targeting sequence or region of complementarity that is complementary to a contiguous sequence of nucleotides within an XDH mRNA, wherein the contiguous sequence of nucleotides is about 12 to about 30 nucleotides in length (e.g., 12 to 30, 12 to 28, 12 to 26, 12 to 24, 12 to 20, 12 to 18, 12 to 16, 14 to 22, 16 to 20, 18 to 20 or 18 to 19 nucleotides in length). In some embodiments, the oligonucleotide comprises a targeting sequence or region of complementarity that is complementary to a contiguous sequence of nucleotides within an XDH mRNA, wherein the contiguous sequence of nucleotides is 10, 11, 12, 13, 14, 15, 16, 17, 18, 19 or 20 nucleotides in length. In some embodiments, the oligonucleotide comprises a targeting sequence or region of complementarity that is complementary to a contiguous sequence of nucleotides within an XDH mRNA, wherein the contiguous sequence of nucleotides is 19 nucleotides in length. In some embodiments, the oligonucleotide comprises a targeting sequence or region of complementarity that is complementary to a contiguous sequence of nucleotides within an XDH mRNA, wherein the contiguous sequence of nucleotides is 20 nucleotides in length.

In some embodiments, an oligonucleotide herein (e.g., an RNAi oligonucleotide) comprises a targeting sequence or region of complementarity having one or more base pair (bp) mismatches with the corresponding XDH target sequence. In some embodiments, the targeting sequence or region of complementarity may have up to about 1, up to about 2, up to about 3, up to about 4, up to about 5, etc. mismatches with the corresponding XDH target sequence provided that the ability of the targeting sequence or region of complementarity to bind or anneal to the XDH mRNA under appropriate hybridization conditions and/or the ability of the oligonucleotide to inhibit XDH expression is maintained. Alternatively, the targeting sequence or region of complementarity may have no more than 1, no more than 2, no more than 3, no more than 4, or no more than 5 mismatches with the corresponding XDH target sequence provided that the ability of the targeting sequence or region of complementarity to bind or anneal to the XDH mRNA under appropriate hybridization conditions and/or the ability of the oligonucleotide to inhibit XDH expression is maintained. In some embodiments, the oligonucleotide comprises a targeting sequence or region of complementarity having 1 mismatch with the corresponding target sequence. In some embodiments, the oligonucleotide comprises a targeting sequence or region of complementarity having 2 mismatches with the corresponding target sequence. In some embodiments, the oligonucleotide comprises a targeting sequence or region of complementarity having 3 mismatches with the corresponding target sequence. In some embodiments, the oligonucleotide comprises a targeting sequence or region of complementarity having 4 mismatches with the corresponding target sequence. In some embodiments, the oligonucleotide comprises a targeting sequence or region of complementarity having 5 mismatches with the corresponding target sequence. In some embodiments, the oligonucleotide comprises a targeting sequence or region of complementarity having more than one mismatch (e.g., 2, 3, 4, 5 or more mismatches) with the corresponding target sequence, wherein at least 2 (e.g., all) of the mismatches are positioned consecutively (e.g., 2, 3, 4, 5 or more mismatches in a row), or wherein the mismatches are interspersed throughout the targeting sequence or region of complementarity. In some embodiments, the oligonucleotide comprises a targeting sequence or region of complementarity having more than one mismatch (e.g., 2, 3, 4, 5 or more mismatches) with the corresponding target sequence, wherein at least 2 (e.g., all) of the mismatches are positioned consecutively (e.g., 2, 3, 4, 5 or more mismatches in a row), or wherein at least one or more non-mismatched base pair is located between the mismatches, or a combination thereof.

Types of Oligonucleotides

A variety of oligonucleotide types and/or structures are useful for targeting XDH in the methods herein including, but not limited to, RNAi oligonucleotides, antisense oligonucleotides (ASOs), miRNAs, etc. Any of the oligonucleotide types described herein or elsewhere are contemplated for use as a framework to incorporate an XDH targeting sequence herein for the purposes of inhibiting XDH expression.

In some embodiments, the oligonucleotides herein inhibit XDH expression by engaging with RNA interference (RNAi) pathways upstream or downstream of Dicer involvement. For example, RNAi oligonucleotides have been developed with each strand having sizes of about 19-25 nucleotides with at least one 3' overhang of 1 to 5 nucleotides (see, e.g., U.S. Pat. No. 8,372,968). Longer oligonucleotides also have been developed that are processed by Dicer to generate active RNAi products (see, e.g., U.S. Pat. No. 8,883,996). Further work produced extended dsRNAs where at least one end of at least one strand is extended beyond a duplex targeting region, including structures where one of the strands includes a thermodynamically stabilizing tetraloop structure (see, e.g., U.S. Pat. Nos. 8,513,207 and 8,927,705, as well as Intl. Patent Application Publication No. WO 2010/033225). Such structures may include single-stranded (ss) extensions (on one or both sides of the molecule) as well as double-stranded (ds) extensions.

In some embodiments, the oligonucleotides herein engage with the RNAi pathway downstream of the involvement of Dicer (e.g., Dicer cleavage). In some embodiments, the oligonucleotides described herein are Dicer substrates. In some embodiments, upon endogenous Dicer processing, double-stranded nucleic acids of 19-23 nucleotides in length capable of reducing XDH expression are produced. In some embodiments, the oligonucleotide has an overhang (e.g., of 1, 2, or 3 nucleotides in length) in the 3' end of the antisense strand. In some embodiments, the oligonucleotide (e.g., siRNA) comprises a 21-nucleotide guide strand that is antisense to a target RNA and a complementary passenger strand, in which both strands anneal to form a 19-bp duplex and 2 nucleotide overhangs at either or both 3' ends. Longer oligonucleotide designs also are available including oligonucleotides having a guide strand of 23 nucleotides and a passenger strand of 21 nucleotides, where there is a blunt end on the right side of the molecule (3' end of passenger strand/5' end of guide strand) and a two nucleotide 3'-guide strand overhang on the left side of the molecule (5' end of the passenger strand/3' end of the guide strand). In such molecules, there is a 21 bp duplex region. See, e.g., U.S. Pat. Nos. 9,012,138; 9,012,621 and 9,193,753.

In some embodiments, the oligonucleotides herein comprise sense and antisense strands that are both in the range of about 17 to 36 (e.g., 17 to 36, 20 to 25 or 21-23) nucleotides in length. In some embodiments, the oligonucleotides described herein comprise an antisense strand of 19-30 nucleotides in length and a sense strand of 19-50 nucleotides in length, wherein the antisense and sense strands are separate strands which form an asymmetric duplex region having an overhang of 1-4 nucleotides at the 3' terminus of the antisense strand. In some embodiments, an oligonucleotide comprises sense and antisense strands, such that there is a 3'-overhang on the antisense strand.

In some embodiments, the antisense oligonucleotide shares a region of complementarity with XDH mRNA. In some embodiments, the antisense oligonucleotide targets various areas of the human XDH gene identified as NM_000379.4. In some embodiments, the antisense oligonucleotide is 15-50 nucleotides in length. In some embodiments, the antisense oligonucleotide is 15-25 nucleotides in length. In some embodiments, the antisense oligonucleotide is 22 nucleotides in length. In some embodiments, the antisense oligonucleotide differs by 1, 2, or 3 nucleotides from the target sequence.

Double-Stranded Oligonucleotides

In some aspects, the disclosure provides double-stranded (ds) RNAi oligonucleotides for targeting XDH mRNA and inhibiting XDH expression (e.g., via the RNAi pathway) comprising a sense strand (also referred to herein as a passenger strand) and an antisense strand (also referred to herein as a guide strand). In some embodiments, the sense strand and antisense strand are separate strands and are not covalently linked. In some embodiments, the sense strand and antisense strand are covalently linked. In some embodiments, the sense strand and antisense strand form a duplex region, wherein the sense strand and antisense strand, or a portion thereof, binds with one another in a complementary fashion (e.g., by Watson-Crick base pairing).

In some embodiments, a first region (R1) of the sense strand and the antisense strand form a first duplex (D1). In some embodiments, D1 is at least about 15 (e.g., at least 15, at least 16, at least 17, at least 18, at least 19, at least 20 or at least 21) nucleotides in length. In some embodiments, D1 is in the range of about 12 to 30 nucleotides in length (e.g., 12 to 30, 12 to 27, 15 to 22, 18 to 22, 18 to 25, 18 to 27, 18 to 30 or 21 to 30 nucleotides in length). In some embodiments, D1 is at least 12 nucleotides in length (e.g., at least 12, at least 15, at least 20, at least 25, or at least 30 nucleotides in length). In some embodiments, D1 is 12, 13, 14, 15, 16, 17, 18, 19, 20, 21, 22, 23, 24, 25, 26, 27, 28, 29 or 30 nucleotides in length. In some embodiments, D1 is 20 nucleotides in length. In some embodiments, D1 comprising sense strand and antisense strand does not span the entire length of the sense strand and/or antisense strand. In some embodiments, D1 comprising the sense strand and antisense strand spans the entire length of either the sense strand or antisense strand or both.

In some embodiments, the sense strand has a second region (R2), wherein R2 comprises a first subregion (S1), a loop (L), such as a tetraloop (tetraL), and a second subregion (S2), wherein L is located between S1 and S2, and wherein S1 and S2 form a second duplex (D2). D2 may have various length. In some embodiments, D2 is about 1-6 bp in length. In some embodiments, D2 is 2-6, 3-6, 4-6, 5-6, 1-5, 2-5, 3-5 or 4-5 bp in length. In some embodiments, D2 is 1, 2, 3, 4, 5 or 6 bp in length. In some embodiments, D2 is 6 bp in length.

In some embodiments, an oligonucleotide provided herein (e.g., an RNAi oligonucleotide) comprises a sense strand having a sequence of any one of SEQ ID NOs: 1, 5, 9, 13, 17, 21, and 25 and an antisense strand comprising a complementary sequence selected from SEQ ID NOs: 2, 6, 10, 14, 18, 22, and 26 as is arranged in Table 2.

In some embodiments, an oligonucleotide provided herein (e.g., an RNAi oligonucleotide) comprises a sense strand and an antisense strand comprising nucleotide sequences selected from:

(a) SEQ ID NOs: 1 and 2, respectively;
(b) SEQ ID NOs: 5 and 6, respectively;
(c) SEQ ID NOs: 9 and 10, respectively;
(d) SEQ ID NOs: 13 and 14, respectively;
(e) SEQ ID NOs: 17 and 18, respectively;
(f) SEQ ID NOs: 21 and 22, respectively; and
(g) SEQ ID NOs: 25 and 26, respectively.

In some embodiments, the sense strand comprises the sequence of SEQ ID NO: 21 and the antisense strand comprises the sequence of SEQ ID NO: 22.

It should be appreciated that, in some embodiments, sequences presented in the Sequence Listing may be referred to in describing the structure of an oligonucleotide (e.g., an RNAi oligonucleotide) or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification when compared with the specified sequence while retaining essentially same or similar complementary properties as the specified sequence.

In some embodiments, oligonucleotides herein (e.g., RNAi oligonucleotides) have one 5' end that is thermodynamically less stable when compared to the other 5' end. In some embodiments, an asymmetric oligonucleotide is provided that includes a 3'-overhang at the 3' end of an antisense strand. In some embodiments, the 3'-overhang on the antisense strand is about 1-8 nucleotides in length (e.g., 1, 2, 3, 4, 5, 6, 7 or 8 nucleotides in length). In some embodiments, the oligonucleotide has an overhang comprising two (2) nucleotides on the 3' end of the antisense strand. In some embodiments, an overhang is a 3'-overhang comprising a length of between 1 and 6 nucleotides, optionally 1 to 5, 1 to 4, 1 to 3, 1 to 2, 2 to 6, 2 to 5, 2 to 4, 2 to 3, 3 to 6, 3 to 5, 3 to 4, 4 to 6, 4 to 5, 5 to 6 nucleotides, or 1, 2, 3, 4, 5 or 6 nucleotides.

In some embodiments, two (2) terminal nucleotides on the 3' end of an antisense strand are modified. In some embodiments, the two (2) terminal nucleotides on the 3' end of the antisense strand are complementary with the target mRNA (e.g., XDH mRNA). In some embodiments, the two (2) terminal nucleotides on the 3' end of the antisense strand are not complementary with the target mRNA. In some embodiments, the two (2) terminal nucleotides on the 3' end of the antisense strand of an oligonucleotide herein are unpaired. In some embodiments, the two (2) terminal nucleotides on the 3' end of the antisense strand of an oligonucleotide herein comprise an unpaired GG. In some embodiments, the two (2) terminal nucleotides on the 3' end of an antisense strand of an oligonucleotide herein are not complementary to the target mRNA. In some embodiments, two (2) terminal nucleotides on each 3' end of an oligonucleotide are GG. In some embodiments, one or both of the two (2) terminal GG nucleotides on each 3' end of an oligonucleotide herein is not complementary with the target mRNA.

In some embodiments, there is one or more (e.g., 1, 2, 3, 4 or 5) mismatch(s) between a sense and antisense strand comprising an oligonucleotide herein (e.g., an RNAi oligonucleotide). If there is more than one mismatch between a sense and antisense strand, they may be positioned consecutively (e.g., 2, 3 or more in a row), or interspersed throughout the region of complementarity. In some embodiments, the 3' end of the sense strand comprises one or more mismatches. In some embodiments, two (2) mismatches are incorporated at the 3' end of the sense strand. In some embodiments, base mismatches, or destabilization of segments at the 3' end of the sense strand of an oligonucleotide herein improves or increases the potency of the oligonucleotide.

Antisense Strands

In some embodiments, an antisense strand of an oligonucleotide herein (e.g., an RNAi oligonucleotide) is referred to as a "guide strand". For example, an antisense strand that engages with RNA-induced silencing complex (RISC) and binds to an Argonaute protein such as Ago2, or engages with or binds to one or more similar factors, and directs silencing of a target gene, as the antisense strand is referred to as a guide strand. In some embodiments, a sense strand comprising a region of complementary to a guide strand is referred to herein as a "passenger strand."

In some embodiments, an oligonucleotide herein (e.g., an RNAi oligonucleotide) comprises an antisense strand of up to about 50 nucleotides in length (e.g., up to 50, up to 40, up to 35, up to 30, up to 27, up to 25, up to 21, up to 19, up to 17 or up to 12 nucleotides in length). In some embodiments, an oligonucleotide comprises an antisense strand of at least about 12 nucleotides in length (e.g., at least 12, at least 15, at least 19, at least 21, at least 22, at least 25, at least 27, at least 30, at least 35 or at least 38 nucleotides in length). In some embodiments, an oligonucleotide comprises an antisense strand in a range of about 12 to about 40 (e.g., 12 to 40, 12 to 36, 12 to 32, 12 to 28, 15 to 40, 15 to 36, 15 to 32, 15 to 28, 17 to 22, 17 to 25, 19 to 27, 19 to 30, 20 to 40, 22 to 40, 25 to 40 or 32 to 40) nucleotides in length. In some embodiments, an oligonucleotide comprises antisense strand of 15 to 30 nucleotides in length. In some embodiments, an antisense strand of any one of the oligonucleotides disclosed herein is of 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length. In some embodiments, an oligonucleotide comprises an antisense strand of 22 nucleotides in length.

In some embodiments, an oligonucleotide herein comprises an antisense strand comprising at least about 12 (e.g., at least 12, at least 13, at least 14, at least 15, at least 16, at least 17, at least 18, at least 19, at least 20, at least 21, at least 22 or at least 23) contiguous nucleotides of a sequence as set forth in any one of SEQ ID NOs: 2, 6, 10, 14, 18, 22, and 26. In some embodiments, an oligonucleotide disclosed herein for targeting XDH comprises an antisense strand comprising or consisting of a sequence as set forth SEQ ID NO: 22. In some embodiments, an oligonucleotide herein comprises an antisense strand comprising at least about 12 (e.g., at least 12, at least 13, at least 14, at least 15, at least 16, at least 17, at least 18, at least 19, at least 20, at least 21, at least 22 or at least 23) contiguous nucleotides of a sequence as set forth in SEQ ID NO: 22.

Sense Strands

In some embodiments, an oligonucleotide disclosed herein for targeting XDH mRNA and inhibiting XDH expression comprises a sense strand sequence as set forth in any one of SEQ ID NOs: 1, 5, 9, 13, 17, 21, and 25. In some embodiments, an oligonucleotide herein has a sense strand comprised of least about 12 (e.g., at least 13, at least 14, at least 15, at least 16, at least 17, at least 18, at least 19, at least 20, at least 21, at least 22 or at least 23) contiguous nucleotides of a sequence as set forth in any one of SEQ ID NOs: 1, 5, 9, 13, 17, 21, and 25. In some embodiments, an oligonucleotide disclosed herein for targeting XDH mRNA and inhibiting XDH expression comprises a sense strand sequence as set forth in SEQ ID NO: 21. In some embodiments, an oligonucleotide herein has a sense strand that comprise at least about 12 (e.g., at least 13, at least 14, at least 15, at least 16, at least 17, at least 18, at least 19, at least 20, at least 21, at least 22 or at least 23) contiguous nucleotides of a sequence as set forth in SEQ ID NO: 21.

In some embodiments, an oligonucleotide provided herein (e.g., an RNAi oligonucleotide) comprises a sense strand (or passenger strand) of up to about 50 nucleotides in length (e.g., up to 50, up to 40, up to 36, up to 30, up to 27, up to 25, up to 21, up to 19, up to 17 or up to 12 nucleotides in length). In some embodiments, an oligonucleotide herein comprises a sense strand of at least about 12 nucleotides in length (e.g., at least 12, at least 15, at least 19, at least 21, at least 25, at least 27, at least 30, at least 36 or at least 38 nucleotides in length). In some embodiments, an oligonucleotide herein comprises a sense strand in a range of about 12 to about 50 (e.g., 12 to 50, 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40 or 32 to 40) nucleotides in length. In some embodiments, an oligonucleotide herein comprises a sense strand of 15 to 50 nucleotides in length. In some embodiments, an oligonucleotide herein comprises a sense strand of 18 to 36 nucleotides in length. In some embodiments, an oligonucleotide herein comprises a sense strand of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, an oligonucleotide herein comprises a sense strand of 36 nucleotides in length.

In some embodiments, an oligonucleotide provided herein (e.g., an RNAi oligonucleotide) comprises a sense strand comprising a stem-loop structure at the 3' end of the sense strand. In some embodiments, the stem-loop is formed by intrastrand base pairing. In some embodiments, a sense strand comprises a stem-loop structure at its 5' end. In some embodiments, the stem of the stem-loop comprises a duplex of 6 nucleotides in length. In some embodiments, the stem of the stem-loop comprises a duplex of 6 nucleotides in length.

In some embodiments, a stem-loop provides the oligonucleotide protection against degradation (e.g., enzymatic degradation), facilitates or improves targeting and/or delivery to a target cell, tissue, or organ (e.g., the liver), or both. For example, in some embodiments, the loop of a stem-loop is comprised of nucleotides comprising one or more modifications that facilitate, improve, or increase targeting to a target mRNA (e.g., an XDH mRNA), inhibition of target gene expression (e.g., XDH expression), and/or delivery, uptake, and/or penetrance into a target cell, tissue, or organ (e.g., the liver), or a combination thereof. In some embodiments, the stem-loop itself or modification(s) to the stem-loop do not affect or do not substantially affect the inherent gene expression inhibition activity of the oligonucleotide, but facilitates, improves, or increases stability (e.g., provides protection against degradation) and/or delivery, uptake, and/or penetrance of the oligonucleotide to a target cell, tissue, or organ (e.g., the liver). In certain embodiments, an oligonucleotide herein comprises a sense strand comprising (e.g., at its 3' end) a stem-loop set forth as: S1-L-S2, in which Si is complementary to S2, and in which L forms a single-stranded loop of linked nucleotides between S1 and S2 of up to about 10 nucleotides in length (e.g., 3, 4, 5, 6, 7, 8, 9 or 10 nucleotides in length). In some embodiments, the loop (L) is 4 nucleotides in length (referred to herein as a "tetraloop".

In some embodiments, the tetraloop comprises the sequence 5'-GAAA-3'. In some embodiments, the stem loop comprises the sequence 5'-GCAGCCGAAAGGCUGC-3' (SEQ ID NO: 29). In some embodiments, a loop (L) of a stem-loop having the structure S1-L-S2 as described above is a tetraloop (tetraL) as describe in U.S. Pat. No. 10,131,912, incorporated herein by reference. In some embodiments, the tetraloop comprises ribonucleotides, deoxyribonucleotides, modified nucleotides, ligands (e.g., delivery ligands), and combinations thereof.

Duplex Length

In some embodiments, a duplex formed between a sense and antisense strand is at least 12 (e.g., at least 15, at least 16, at least 17, at least 18, at least 19, at least 20, or at least 21) nucleotides in length. In some embodiments, a duplex formed between a sense and antisense strand is in the range of 12-30 nucleotides in length (e.g., 12 to 30, 12 to 27, 12 to 22, 15 to 25, 18 to 30, 18 to 22, 18 to 25, 18 to 27, 18 to 30, 19 to 30 or 21 to 30 nucleotides in length). In some embodiments, a duplex formed between a sense and antisense strand is 12, 13, 14, 15, 16, 17, 18, 19, 20, 21, 22, 23, 24, 25, 26, 27, 28, 29 or 30 nucleotides in length. In some embodiments, a duplex formed between a sense and antisense strand is 12 nucleotides in length. In some embodiments, a duplex formed between a sense and antisense strand is 13 nucleotides in length. In some embodiments, a duplex formed between a sense and antisense strand is 14 nucleotides in length. In some embodiments, a duplex formed between a sense and antisense strand is 15 nucleotides in length. In some embodiments, a duplex formed between a sense and antisense strand is 16 nucleotides in length. In some embodiments, a duplex formed between a sense and antisense strand is 17 nucleotides in length. In some embodiments, a duplex formed between a sense and antisense strand is 18 nucleotides in length. In some embodiments, a duplex formed between a sense and antisense strand is 19 nucleotides in length. In some embodiments, a duplex formed between a sense and antisense strand is 20 nucleotides in length. In some embodiments, a duplex formed between a sense and antisense strand is 21 nucleotides in length. In some embodiments, a duplex formed between a sense and antisense strand is 22 nucleotides in length. In some embodiments, a duplex formed between a sense and antisense strand is 23 nucleotides in length. In some embodiments, a duplex formed between a sense and antisense strand is 24 nucleotides in length. In some embodiments, a duplex formed between a sense and antisense strand is 25 nucleotides in length. In some embodiments, a duplex formed between a sense and antisense strand is 26 nucleotides in length. In some embodiments, a duplex formed between a sense and antisense strand is 27 nucleotides in length. In some embodiments, a duplex formed between a sense and antisense strand is 28 nucleotides in length. In some embodiments, a duplex formed between a sense and antisense strand is 29 nucleotides in length. In some embodiments, a duplex formed between a sense and antisense strand is 30 nucleotides in length. In some embodiments, a duplex formed between a sense and antisense strand does not span the entire length of the sense strand and/or antisense strand. In some embodiments, a duplex between a sense and antisense strand spans the entire length of either the sense or antisense strands. In some embodiments, a duplex between a sense and antisense strand spans the entire length of both the sense strand and the antisense strand.

Oligonucleotide Termini

In some embodiments, an oligonucleotide herein comprises sense and antisense strands that are separate strands which form an asymmetric duplex region having an overhang at the 3' terminus of the antisense strand. In some embodiments, the one or more nucleotides comprising the overhang are unpaired nucleotides.

In some embodiments, an oligonucleotide herein comprises a sense strand and an antisense strand, wherein the antisense strand comprises a 3'-overhang comprising one or more nucleotides.

In some embodiments, the 3'-overhang is about one (1) to three (3) nucleotides in length (e.g., about 1, 2, or 3 nucleotides in length). In some embodiments, the 3'-overhang is (1) nucleotide in length. In some embodiments, the 3'-overhang is two (2) nucleotides in length. In some embodiments, the 3'-overhang is three (3) nucleotides in length.

In some embodiments, one or more (e.g., 2, 3, 4, 5, or more) nucleotides comprising the 3' terminus or 5' terminus of a sense and/or antisense strand are modified. For example, in some embodiments, one or two terminal nucleotides of the 3' terminus of the antisense strand are modified. In some embodiments, the last nucleotide at the 3' terminus of an antisense strand is modified, such that it comprises 2' modification, or it comprises, a 2'-O-methoxyethyl. In some embodiments, the last one or two terminal nucleotides at the 3' terminus of an antisense strand are complementary with the target. In some embodiments, the last one or two nucleotides at the 3' terminus of the antisense strand are not complementary with the target.

In some embodiments, an oligonucleotide disclosed herein (e.g., an RNAi oligonucleotide) comprises a sense strand and an antisense strand, wherein the 3' terminus of the sense strand comprises a stem-loop described herein and the 3' terminus of the antisense strand comprises a 3'-overhang described herein. In some embodiments, an oligonucleotide herein (e.g., an RNAi oligonucleotide) comprises a sense strand and an antisense strand that form a nicked tetraloop structure described herein, wherein the 3' terminus of the sense strand comprises a stem-loop, wherein the loop is a tetraloop described herein, and wherein the 3' terminus of the antisense strand comprises a 3'-overhang described herein. In some embodiments, the 3'-overhang is two (2) nucleotides in length. In some embodiments, the two (2) nucleotides comprising the 3'-overhang both comprise guanine (G) nucleobases. Typically, one or both of the nucleotides comprising the 3'-overhang of the antisense strand are not complementary with the target mRNA. An exemplary nicked tetraloop structure is provided in FIG. 3. In some embodiments, an oligonucleotide described herein comprises the nicked tetraloop structure shown in FIG. 3.

Oligonucleotide Modifications

In some embodiments, an oligonucleotide described herein (e.g., an RNAi oligonucleotide) comprises a modification. Oligonucleotides (e.g., RNAi oligonucleotides) may be modified in various ways to improve or control specificity, stability, delivery, bioavailability, resistance from nuclease degradation, immunogenicity, base-pairing properties, RNA distribution and cellular uptake and other features relevant to therapeutic or research use.

In some embodiments, the modification is a modified sugar. In some embodiments, the modification is a 5'-terminal phosphate group. In some embodiments, the modification is a modified internucleotide linkage. In some embodiments, the modification is a modified base. In some embodiments, an oligonucleotide described herein can comprise any one of the modifications described herein or any combination thereof. For example, in some embodiments, an oligonucleotide described herein comprises at least one modified sugar, a 5'-terminal phosphate group, at least one modified internucleotide linkage, and at least one modified base.

The number of modifications on an oligonucleotide (e.g., an RNAi oligonucleotide) and the position of those nucleotide modifications may influence the properties of an oligonucleotide. For example, oligonucleotides may be delivered in vivo by conjugating them to or encompassing them in a lipid nanoparticle (LNP) or similar carrier. However, when an oligonucleotide is not protected by an LNP or similar carrier, it may be advantageous for at least some of the nucleotides to be modified. Accordingly, in some embodiments, all or substantially all the nucleotides of an oligonucleotide are modified. In some embodiments, more than half of the nucleotides are modified. In some embodiments, less than half of the nucleotides are modified. In some embodiments, the sugar moiety of all nucleotides comprising the oligonucleotide is modified at the 2' position. The modifications may be reversible or irreversible. In some embodiments, an oligonucleotide as disclosed herein has a number and type of modified nucleotides sufficient to cause the desired characteristics (e.g., protection from enzymatic degradation, capacity to target a desired cell after in vivo administration, and/or thermodynamic stability).

Sugar Modifications

In some embodiments, an oligonucleotide described herein (e.g., an RNAi oligonucleotide) comprises a modified sugar. In some embodiments, a modified sugar (also referred herein to a sugar analog) includes a modified deoxyribose or ribose moiety in which, for example, one or more modifications occur at the 2', 3', 4' and/or 5' carbon position of the sugar. In some embodiments, a modified sugar may also include non-natural alternative carbon structures such as those present in locked nucleic acids ("LNA"; see, e.g., Koshkin et al. (1998) Tetrahedon 54:3607-30), unlocked nucleic acids ("UNA"; see, e.g., Snead et al. (2013) Mol. Ther-Nucl. Acids 2:e103) and bridged nucleic acids ("BNA"; see, e.g., Imanishi & Obika (2002) Chem Commun. (Camb) 21:1653-59).

In some embodiments, a nucleotide modification in a sugar comprises a 2'-modification. In some embodiments, a 2'-modification may be 2'-O-propargyl, 2'-O-propylamin, 2'-amino, 2'-ethyl, 2'-fluoro (2'-F), 2'-aminoethyl (EA), 2'-O-methyl (2'-OMe), 2'-O-methoxyethyl (2'-MOE), 2'-O-[2-(methylamino)-2-oxoethyl](2'-O-NMA) or 2'-deoxy-2'-fluoro-β-d-arabinonucleic acid (2'-FANA). In some embodiments, the modification is 2'-F, 2'-OMe or 2'-MOE. In some embodiments, a modification in a sugar comprises a modification of the sugar ring, which may comprise modification of one or more carbons of the sugar ring. For example, a modification of a sugar of a nucleotide may comprise a 2'-oxygen of a sugar is linked to a 1'-carbon or 4'-carbon of the sugar, or a 2'-oxygen is linked to the 1'-carbon or 4'-carbon via an ethylene or methylene bridge. In some embodiments, a modified nucleotide has an acyclic sugar that lacks a 2'-carbon to 3'-carbon bond. In some embodiments, a modified nucleotide has a thiol group, e.g., in the 4' position of the sugar.

In some embodiments, an oligonucleotide (e.g., an RNAi oligonucleotide) described herein comprises at least about 1 modified nucleotide (e.g., at least 1, at least 5, at least 10, at least 15, at least 20, at least 25, at least 30, at least 35, at least 40, at least 45, at least 50, at least 55, at least 60, or more). In some embodiments, the sense strand of the oligonucleotide comprises at least about 1 modified nucleotide (e.g., at least 1, at least 5, at least 10, at least 15, at least 20, at least 25, at least 30, at least 35, or more). In some embodiments, the antisense strand of the oligonucleotide comprises at least about 1 modified nucleotide (e.g., at least 1, at least 5, at least 10, at least 15, at least 20, or more).

In some embodiments, all the nucleotides of the sense strand of the oligonucleotide are modified. In some embodiments, all the nucleotides of the antisense strand of the oligonucleotide are modified. In some embodiments, all the nucleotides of the oligonucleotide (i.e., both the sense strand and the antisense strand) are modified. In some embodiments, the modified nucleotide comprises a 2'-modification (e.g., a 2'-F or 2'-OMe, 2'-MOE, and 2'-deoxy-2'-fluoro-β-d-arabinonucleic acid).

In some embodiments, the disclosure provides oligonucleotides having different modification patterns. In some embodiments, an oligonucleotide herein comprises a sense strand having a modification pattern as set forth in the Examples and Sequence Listing and an antisense strand having a modification pattern as set forth in the Examples and Sequence Listing.

In some embodiments, an oligonucleotide disclosed herein (e.g., an RNAi oligonucleotide) comprises an antisense strand having nucleotides that are modified with 2'-F. In some embodiments, an oligonucleotide herein comprises an antisense strand comprising nucleotides that are modified with 2'-F and 2'-OMe. In some embodiments, an oligonucleotide disclosed herein comprises a sense strand having nucleotides that are modified with 2'-F. In some embodiments, an oligonucleotide disclosed herein comprises a sense strand comprises nucleotides that are modified with 2'-F and 2'-OMe.

In some embodiments, an oligonucleotide described herein comprises a sense strand with about 10-15%, 10%, 11%, 12%, 13%, 14% or 15% of the nucleotides of the sense strand comprising a 2'-fluoro modification. In some embodiments, about 11% of the nucleotides of the sense strand comprise a 2-fluoro modification. In some embodiments, an oligonucleotide described herein comprises an antisense strand with about 25-35%, 25%, 26%, 27%, 28%, 29%, 30%, 31%, 32%, 33%, 34% or 35% of the nucleotides of the antisense strand comprising a 2'-fluoro modification. In some embodiments, about 32% of the nucleotides of the antisense strand comprise a 2'-fluoro modification. In some embodiments, the oligonucleotide has about 15-25%, 15%, 16%, 17%, 18%, 19%, 20%, 21%, 22%, 23%, 24%, or 25% of its nucleotides comprising a 2'-fluoro modification. In some embodiments, about 19% of the nucleotides in the oligonucleotide comprise a 2'-fluoro modification.

In some embodiments, one or more of positions 8, 9, 10 or 11 of the sense strand is modified with a 2'-F group. In some embodiments, one or more of positions 2, 3, 4, 5, 7, 10 and 14 of the antisense strand is modified with a 2'-F group. In some embodiments, the sugar moiety at each of nucleotides at positions 1-7, 12-27 and 31-36 in the sense strand is modified with a 2'-OMe. In some embodiments, the sugar moiety at each of nucleotides at positions 1, 6, 8, 9, 11-13 and 15-22 in the antisense strand is modified with a 2'-OMe.

In some embodiments, an oligonucleotide provided herein comprises an antisense strand having the sugar moiety of each of the nucleotides at positions 2, 3, 4, 5, 7, 10, and 14 of the antisense strand modified with 2'-F and the sugar moiety of each of the remaining nucleotides of the antisense strand modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl](2'-O-NMA), and 2'-deoxy-2'-fluoro-β-d-arabinonucleic acid (2'-FANA).

In some embodiments, an oligonucleotide provided herein comprises a sense strand having the sugar moiety at positions 8-11 modified with 2'-F. In some embodiments, an oligonucleotide provided herein comprises a sense strand having the sugar moiety at positions 1-7, 12-27 and 31-36 modified with 2'OMe.

5'-Terminal Phosphate

In some embodiments, an oligonucleotide described herein (e.g., an RNAi oligonucleotide) comprises a sense strand and an antisense strand, wherein the antisense strand comprises a 5'-terminal phosphate. In some embodiments, 5'-terminal phosphate groups of an RNAi oligonucleotide enhance the interaction with Ago2. However, oligonucleotides comprising a 5'-phosphate group may be susceptible to degradation via phosphatases or other enzymes, which can limit their performance and/or bioavailability in vivo. In some embodiments, an oligonucleotide herein includes analogs of 5' phosphates that are resistant to such degradation. In some embodiments, the phosphate analog is oxymethyl phosphonate, vinyl phosphonate or malonyl phosphonate, or a combination thereof. In certain embodiments, the 5' terminus of an oligonucleotide strand is attached to chemical moiety that mimics the electrostatic and steric properties of a natural 5'-phosphate group ("phosphate mimic").

In some embodiments, an oligonucleotide herein (e.g., an RNAi oligonucleotide) has a phosphate analog at a 4'-carbon position of the sugar (referred to as a "4'-phosphate analog"). See, e.g., Intl. Patent Application Publication No. WO 2018/045317. In some embodiments, an oligonucleotide herein comprises a 4'-phosphate analog at a 5'-terminal nucleotide. In some embodiments, a phosphate analog is an oxymethyl phosphonate, in which the oxygen atom of the oxymethyl group is bound to the sugar moiety (e.g., at its 4'-carbon) or analog thereof. In other embodiments, a 4'-phosphate analog is a thiomethylphosphonate or an aminomethylphosphonate, in which the sulfur atom of the thiomethyl group or the nitrogen atom of the amino methyl group is bound to the 4'-carbon of the sugar moiety or analog thereof. In certain embodiments, a 4'-phosphate analog is an oxymethyl phosphonate. In some embodiments, an oxymethyl phosphonate is represented by the formula $-O-CH_2-PO(OH)_2$, $-O-CH_2-PO(OR)_2$, or —O—CH2-PO(OH)(R), in which R is independently selected from H, $CH_3$, an alkyl group, $CH_2CH_2CN$, $CH_2OCOC(CH_3)_3$, $CH_2OCH_2CH_2Si(CH_3)_3$ or a protecting group. In certain embodiments, the alkyl group is $CH_2CH_3$. More typically, R is independently selected from H, $CH_3$ or $CH_2CH_3$. In some embodiment, R is CH3. In some embodiments, the 4'-phosphate analog is 4'-oxymethyl phosphonate.

In some embodiments, an oligonucleotide provided herein comprises an antisense strand comprising a 4'-phosphate analog at the 5'-terminal nucleotide, wherein 5'-terminal nucleotide comprises the following structure (Chem 1):

Chem 1

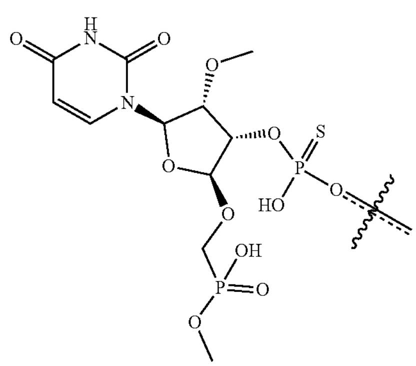

4'-O-monomethylphosphonate-2'-O-methyluridine phosphorothioate [MePhosphonate-4O-mUs].

Modified Internucleotide Linkage

In some embodiments, an oligonucleotide provided herein (e.g., a RNAi oligonucleotide) comprises a modified internucleotide linkage. In some embodiments, phosphate modifications or substitutions result in an oligonucleotide that comprises at least about 1 (e.g., at least 1, at least 2, at least 3 or at least 5) modified internucleotide linkage. In some embodiments, any one of the oligonucleotides disclosed herein comprises about 1 to about 10 (e.g., 1 to 10, 2 to 8, 4 to 6, 3 to 10, 5 to 10, 1 to 5, 1 to 3 or 1 to 2) modified internucleotide linkages. In some embodiments, any one of the oligonucleotides disclosed herein comprises 1, 2, 3, 4, 5, 6, 7, 8, 9 or 10 modified internucleotide linkages.

A modified internucleotide linkage may be a phosphorodithioate linkage, a phosphorothioate linkage, a phosphotriester linkage, a thionoalkylphosphonate linkage, a thionalkylphosphotriester linkage, a phosphoramidite linkage, a phosphonate linkage or a boranophosphate linkage. In some embodiments, at least one modified internucleotide linkage of any one of the oligonucleotides as disclosed herein is a phosphorothioate linkage.

In some embodiments, an oligonucleotide provided herein (e.g., a RNAi oligonucleotide) has a phosphorothioate linkage between one or more of positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand. In some embodiments, the oligonucleotide described herein has a phosphorothioate linkage between each of positions 1 and 2 of the sense strand, positions 1 and 2 of the antisense strand, positions 2 and 3 of the antisense strand, positions 20 and 21 of the antisense strand, and positions 21 and 22 of the antisense strand.

Targeting Ligands

In some embodiments, it is desirable to target an oligonucleotide provided herein (e.g., an RNAi oligonucleotide) to one or more cells or cell type, tissues, organs, or anatomical regions or compartments. Such a strategy may help to avoid undesirable effects to the organism treated and/or to avoid undue loss of the oligonucleotide to cells, tissues, organs, or anatomical regions or compartments that would not benefit from the oligonucleotide or its effects (e.g., inhibition or reduction of XDH expression). Accordingly, in some embodiments, oligonucleotides disclosed herein (e.g., RNAi oligonucleotides) are modified to facilitate targeting and/or delivery to particular cells or cell types, tissues, organs, or anatomical regions or compartments (e.g., to facilitate delivery of the oligonucleotide to the liver). In some embodiments, an oligonucleotide comprises at least one nucleotide (e.g., 1, 2, 3, 4, 5, 6 or more nucleotides) conjugated to one or more targeting ligand(s).

In some embodiments, the targeting ligand comprises a carbohydrate, amino sugar, cholesterol, peptide, polypeptide, protein, or part of a protein (e.g., an antibody or antibody fragment), or lipid. In certain embodiments, the targeting ligand is a carbohydrate comprising at least one GalNAc moiety.

In some embodiments, 1 or more (e.g., 1, 2, 3, 4, 5 or 6) nucleotides of an oligonucleotide provided herein (e.g., an RNAi oligonucleotide) are each conjugated to a separate targeting ligand (e.g., a GalNAc moiety). In some embodiments, 2 to 4 nucleotides of an oligonucleotide are each conjugated to a separate targeting ligand. In some embodiments, targeting ligands are conjugated to 2 to 4 nucleotides at either end of the sense strand. For example, an oligonucleotide may comprise a stem-loop at 3' terminus of the sense strand and 1, 2, 3 or 4 nucleotides of the loop of the stem may be individually conjugated to a targeting ligand. In some embodiments, an oligonucleotide provided by the disclosure (e.g., a RNAi oligonucleotide) comprises a stem-loop at the 3' terminus of the sense strand, wherein the loop of the stem-loop comprises a tetraloop, and wherein 3 nucleotides of the tetraloop are individually conjugated to a targeting ligand.

In some embodiments, the nucleotide at the 5'terminus of the sense strand comprises a targeting ligand and the 3' terminus of the sense strand comprises a stem-loop, wherein 1, 2, 3 or 4 nucleotides of the loop of the stem are individually conjugated to a targeting ligand, wherein the targeting ligands at the 5' and 3' termini are different. In some embodiments, the nucleotide at the 5'terminus of the sense strand comprises a targeting ligand and the 3' terminus of the sense strand comprises a stem-loop, wherein the loop of the stem-loop comprises a tetraloop, and wherein 3 nucleotides of the tetraloop are individually conjugated to a targeting ligand, wherein the targeting ligands at the 5' and 3' termini are different.

GalNAc Ligands

GalNAc is a high affinity carbohydrate ligand for the asialoglycoprotein receptor (ASGPR), which is primarily expressed on the surface of hepatocyte cells and has a major role in binding, internalizing and subsequent clearing circulating glycoproteins that contain terminal galactose or GalNAc residues (asialoglycoproteins). Conjugation (either indirect or direct) of GalNAc moieties to oligonucleotides of the instant disclosure can be used to target these oligonucleotides to the ASGPR expressed on cells. In some embodiments, an oligonucleotide of the instant disclosure (e.g., an RNAi oligonucleotide) is conjugated to at least one or more GalNAc moieties, wherein the GalNAc moieties target the oligonucleotide to an ASGPR expressed on human liver cells (e.g., human hepatocytes). In some embodiments, the GalNAc moiety target the oligonucleotide to the liver.

In some embodiments, an oligonucleotide of the instant disclosure (e.g., an RNAi oligonucleotide) is conjugated directly or indirectly to a monovalent GalNAc moiety. In some embodiments, the oligonucleotide is conjugated directly or indirectly to more than one monovalent GalNAc (i.e., is conjugated to 2, 3 or 4 monovalent GalNAc moieties and is typically conjugated to 3 or 4 monovalent GalNAc moieties). In some embodiments, an oligonucleotide is conjugated to one or more bivalent GalNAc, trivalent GalNAc or tetravalent GalNAc moieties. In some embodiments, a bivalent, trivalent or tetravalent GalNAc moiety is conjugated to an oligonucleotide via a branched linker. In some embodiments, a monovalent GalNAc moiety is conjugated to a first nucleotide and a bivalent, trivalent, or tetravalent GalNAc moiety is conjugated to a second nucleotide via a branched linker.

In some embodiments, one (1) or more (e.g., 1, 2, 3, 4, 5 or 6) nucleotides of an oligonucleotide described herein (e.g., an RNAi oligonucleotide) are each conjugated to a GalNAc moiety. In some embodiments, two (2) to four (4) nucleotides of a tetraloop are each conjugated to a separate GalNAc moiety. In some embodiments, targeting ligands are conjugated to two (2) to four (4) nucleotides at either ends of the sense or antisense strand (e.g., ligands are conjugated to a two (2) to four (4) nucleotide overhang or extension on the 5' or 3' terminus of the sense or antisense strand) such that the GalNAc moieties resemble bristles of a toothbrush and the oligonucleotide resembles a toothbrush. In some embodiments, GalNAc moieties are conjugated to a nucleotide of the sense strand. For example, three (3) or four (4) GalNAc moieties can be conjugated to nucleotides in the tetraloop of the sense strand where each GalNAc moiety is conjugated to one (1) nucleotide.

In some embodiments, an oligonucleotide described herein (e.g., an RNAi oligonucleotide) comprises a tetraloop, wherein the tetraloop (tetraL) is any combination of adenine (A) and guanine (G) nucleotides. In some embodiments, the tetraloop (tetraL) comprises a monovalent GalNAc moiety attached to any one or more guanine (G) nucleotides of the tetraloop via any linker described herein, as depicted below in Chem 2 (X=heteroatom):

Chem 2

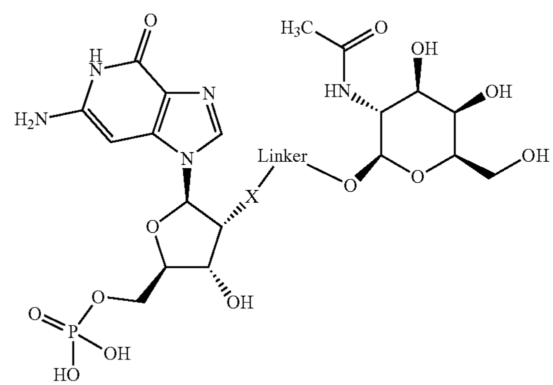

In some embodiments, the tetraloop (tetraL) has a monovalent GalNAc attached to any one or more adenine nucleotides of the tetraloop via any linker described herein, as depicted below in Chem 3 (X=heteroatom):

Chem 3

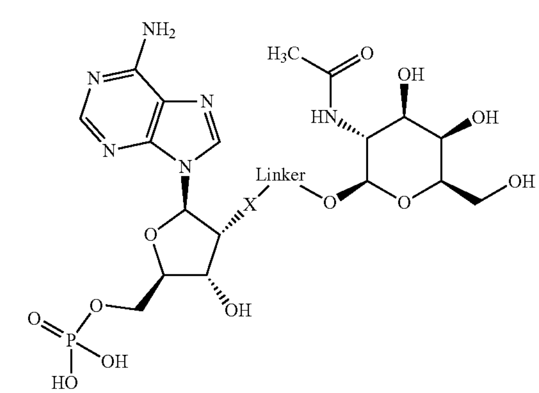

In some embodiments, an oligonucleotide herein (e.g., an RNAi oligonucleotide) comprises a monovalent GalNAc moiety attached to a guanine (G) nucleotide referred to as [ademG-GalNAc] or 2'-aminodiethoxymethanol-Guanine-GalNAc, as depicted below in Chem 4:

Chem 4

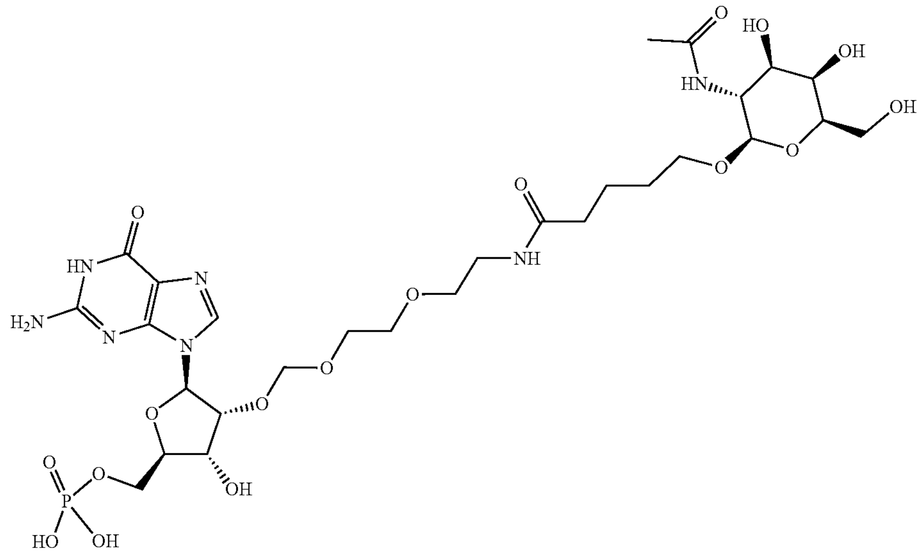

In some embodiments, an oligonucleotide herein comprises a monovalent GalNAc moiety attached to an adenine nucleotide, referred to as [ademA-GalNAc] or 2'-aminodiethoxymethanol-Adenine-GalNAc, as depicted below in Chem 5:

Chem 5

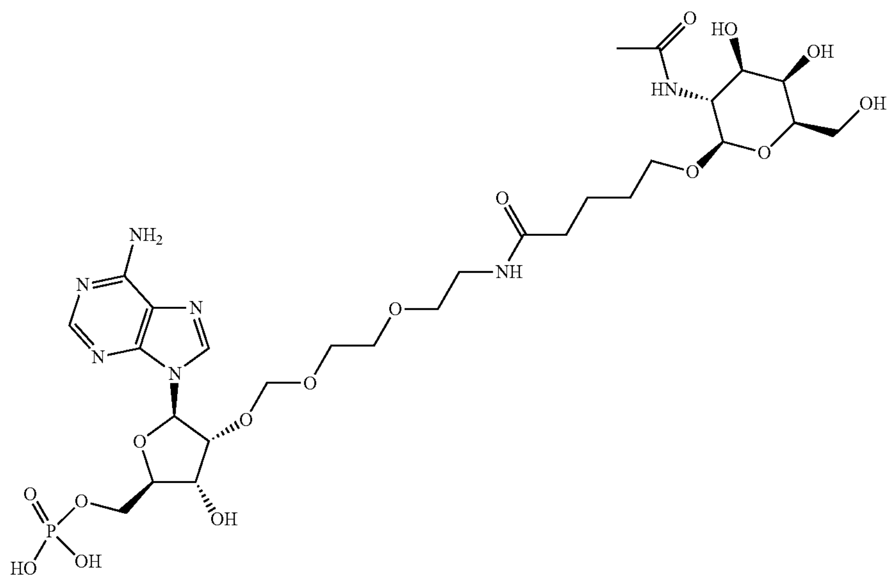

An example of such conjugation is shown below for a loop comprising from 5' to 3' the nucleotide sequence GAAA (L=linker, X=heteroatom). Such a loop may be present, for example, at positions 27-30 of a sense strand provided herein. In the chemical formula,

is used to describe an attachment point to the oligonucleotide strand (Chem 6).

Chem 6

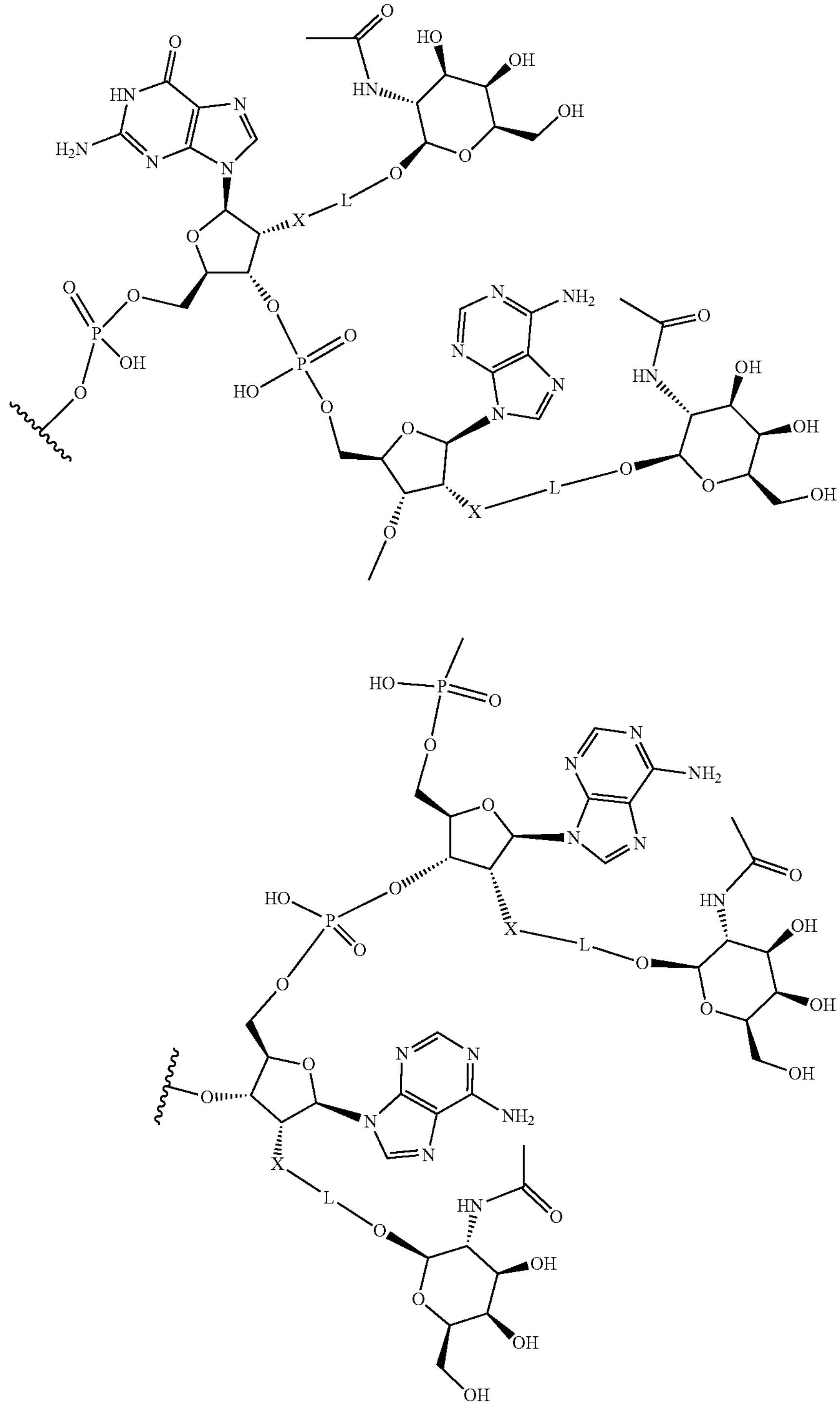

Appropriate methods or chemistry (e.g., click chemistry) can be used to link a targeting ligand to a nucleotide. In some embodiments, a targeting ligand is conjugated to a nucleotide comprising an oligonucleotide herein (e.g., an RNAi oligonucleotide) using a click linker. In some embodiments, an acetal-based linker is used to conjugate a targeting ligand to a nucleotide of any one of the oligonucleotides described herein. Acetal-based linkers are disclosed, for example, in Intl. Patent Application Publication No. WO2016/100401. In some embodiments, the linker is a labile linker. However, in other embodiments, the linker is stable. An example is shown below for a loop comprising from 5' to 3' the nucleotides GAAA, in which GalNAc moieties are attached to nucleotides of the loop using an acetal linker (Chem 7 and Chem 8). Such a loop may be present, for example, at positions 27-30 of the any one of the sense strands. In the chemical formula,

is an attachment point to the oligonucleotide strand.
Chem 7
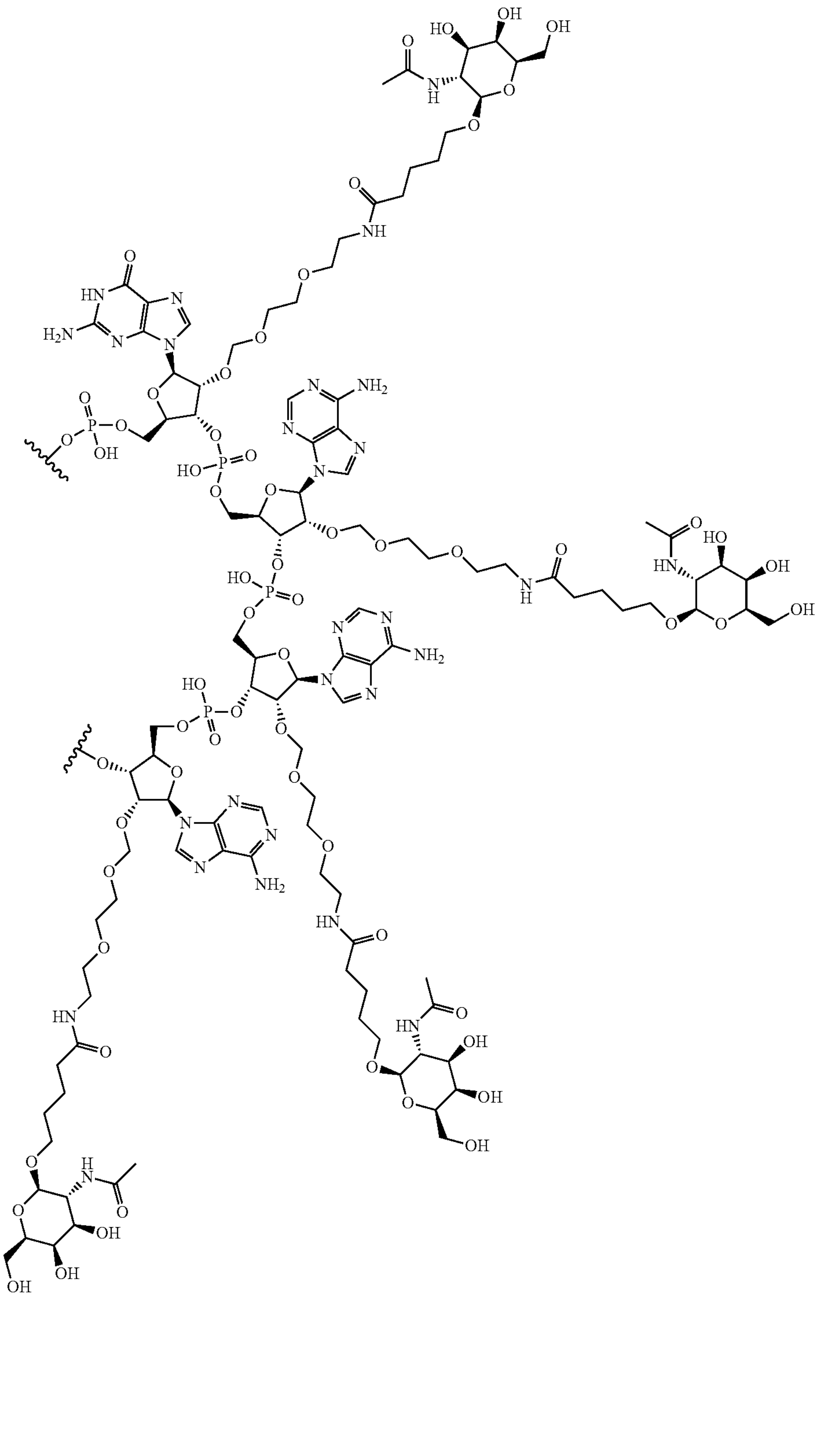
or -continued Chem 8

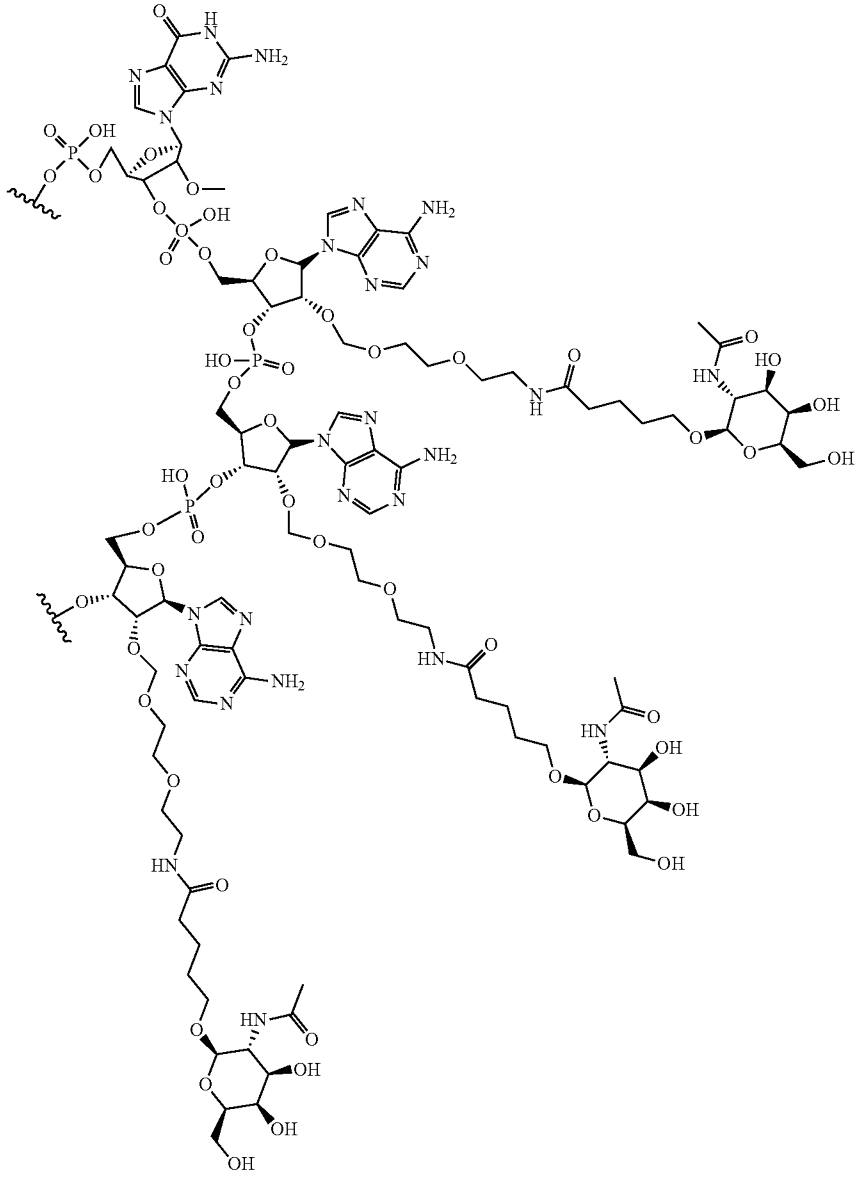

As mentioned, various appropriate methods or chemistry synthetic techniques (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in Intl. Patent Application Publication No. WO 2016/100401. In some embodiments, the linker is a labile linker. However, in other embodiments, the linker is a stable linker.

Lipid Targeting Ligands

In some embodiments, the disclosure provides an oligonucleotide one or more lipids conjugated to the oligonucleotide.

In some embodiments, the oligonucleotide comprises a sense strand of 36 nucleotides with positions numbered 1-36 from 5' to 3'. In some embodiments, the oligonucleotide comprises a lipid conjugated to position 1 of a 36-nucleotide sense strand. In some embodiments, the oligonucleotide comprises a lipid conjugated to the 5' terminal nucleotide of the sense strand.

In some embodiments, the oligonucleotide comprises a lipid conjugated to the 5' terminal nucleotide of a 36-nucleotide sense strand.

In some embodiments, the oligonucleotide comprises a C8-C30 hydrocarbon chain conjugated to position 1 of a 36-nucleotide sense strand. In some embodiments, the oligonucleotide comprises a C22 hydrocarbon chain conjugated to position 1 of a 36-nucleotide sense strand.

In some embodiments, the oligonucleotide comprises a lipid conjugated to the 5' terminal nucleotide of the sense strand. In some embodiments, the oligonucleotide comprises a C8-C30 hydrocarbon chain conjugated to the 5'terminal nucleotide of the sense strand. In some embodiments, the oligonucleotide comprises a C22 hydrocarbon chain conjugated to the 5' terminal nucleotide of the sense strand.

In some embodiments, the oligonucleotide comprises a hydrocarbon chain conjugated to the 2' carbon of the ribose ring of the 5' terminal nucleotide of the sense strand. In some embodiments, the oligonucleotide comprises a C8-C30 hydrocarbon chain conjugated to the 2' carbon of the ribose ring of the 5' terminal nucleotide of the sense strand. In some embodiments, the oligonucleotide comprises a C22 hydrocarbon chain conjugated to the 2' carbon of the ribose ring of the 5' terminal nucleotide of the sense strand.

In some embodiments, the oligonucleotide comprises a lipid conjugated to the 5' terminal nucleotide of the sense strand via a linker. In some embodiments, the oligonucleotide comprises a C8-C30 hydrocarbon chain conjugated to the 5'terminal nucleotide of the sense strand via a linker. In some embodiments, the oligonucleotide comprises a C22 hydrocarbon chain conjugated to the 5' terminal nucleotide of the sense strand via a linker.

In some embodiments, the oligonucleotide comprises a hydrocarbon chain conjugated to the 2' carbon of the ribose ring of the 5' terminal nucleotide of the sense strand via a linker. In some embodiments, the oligonucleotide comprises a C8-C30 hydrocarbon chain conjugated to the 2' carbon of the ribose ring of the 5' terminal nucleotide of the sense strand via a linker. In some embodiments, the oligonucleotide comprises a C22 hydrocarbon chain conjugated to the 2' carbon of the ribose ring of the 5' terminal nucleotide of the sense strand via a linker. In some embodiments, the C22 hydrocarbon chain is represented by

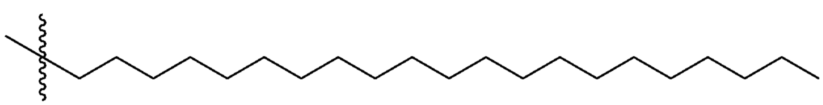

.

Exemplary Oligonucleotides for Reducing XDH Expression

In some embodiments, an oligonucleotide provided herein (e.g., an RNAi oligonucleotide) comprises a sense strand having a sequence of any one of SEQ ID NOs: 1, 5, 9, 13, 17, 21, and 25 and an antisense strand comprising a complementary sequence selected from SEQ ID NOs: 2, 6, 10, 14, 18, 22, and 26.

In some embodiments, an oligonucleotide provided herein (e.g., an RNAi oligonucleotide) comprises a sense strand having a sequence of any one of SEQ ID NOs: 3, 7, 11, 15, 19, 23, and 27 and an antisense strand comprising a complementary sequence selected from SEQ ID NOs: 4, 8, 12, 16, 20, 24, and 28.

In some embodiments, an oligonucleotide provided herein (e.g., and RNAi oligonucleotide) for reducing XDH expression comprises:

a sense strand comprising a C22 hydrocarbon chain conjugated nucleotide at position 1, a 2'-F modified nucleotide at positions 8-11, a 2'-OMe modified nucleotide at positions 2-7, 12-27, and 31-36, a GalNAc-conjugated nucleotide at position 28, 29 and 30, and a phosphorothioate linkage between positions 1 and 2;

an antisense strand comprising a 2'-F modified nucleotide at positions 2, 3, 4, 5, 7, 10 and 14, a 2'-OMe at positions 1, 6, 8, 9, 11-13, and 15-22, a phosphorothioate linkage between positions 1 and 2, positions 2 and 3, positions 3 and 4, positions 20 and 21, and positions 21 and 22, and a 5'-terminal nucleotide at position 1 comprising a 4'-phosphate analog, optionally wherein the 5'-terminal nucleotide comprises 4'-O-monomethylphosphonate-2'-O-methyluridine [MePhosphonate-4O-mU]; wherein positions 1-20 of the antisense strand form a duplex region with positions 1-20 of the sense strand, wherein positions 21-36 of the sense strand form a stem-loop, wherein positions 27-30 form the loop of the stem-loop, optionally wherein positions 27-30 comprise a tetraloop, wherein positions 21 and 22 of the antisense strand comprise an overhang, and wherein the sense strand and antisense strands comprise nucleotide sequences selected from the group consisting of:

(a) the sense strand comprises a sequence as set forth in SEQ ID NO: 1 and the antisense strand comprises a sequence as set forth in SEQ ID NO: 2;

(b) the sense strand comprises a sequence as set forth in SEQ ID NO: 5 and the antisense strand comprises a sequence as set forth in SEQ ID NO: 6;

(c) the sense strand comprises a sequence as set forth in SEQ ID NO: 9 and the antisense strand comprises a sequence as set forth in SEQ ID NO: 10;

(d) the sense strand comprises a sequence as set forth in SEQ ID NO: 13 and the antisense strand comprises a sequence as set forth in SEQ ID NO: 14;

(e) the sense strand comprises a sequence as set forth in SEQ ID NO: 17 and the antisense strand comprises a sequence as set forth in SEQ ID NO: 18;

(f) the sense strand comprises a sequence as set forth in SEQ ID NO: 21 and the antisense strand comprises a sequence as set forth in SEQ ID NO: 22; and (g) the sense strand comprises a sequence as set forth in SEQ ID NO: 25 and the antisense strand comprises a sequence as set forth in SEQ ID NO: 26.

In some embodiments, the XDH-targeting oligonucleotides (e.g., an RNAi oligonucleotide) for reducing XDH expression comprise:

a sense strand comprising a C22 hydrocarbon chain conjugated nucleotide at position 1, a 2'-F modified nucleotide at positions 8-11, a 2'-OMe modified nucleotide at positions 2-7, 12-27, and 31-36, a GalNAc-conjugated nucleotide at position 28, 29 and 30; and a phosphorothioate linkage between positions 1 and 2;

an antisense strand comprising a 2'-F modified nucleotide at positions 2, 3, 4, 5, 7, 10 and 14, a 2'-OMe at positions 1, 6, 8, 9, 11-13, and 15-22, a phosphorothioate linkage between positions 1 and 2, positions 2 and 3, positions 3 and 4, positions 20 and 21, and positions 21 and 22, and a 5'-terminal nucleotide at position 1 comprising a 4'-phosphate analog, optionally wherein the 5'-terminal nucleotide comprises 4'-O-monomethylphosphonate-2'-O-methyluridine [MePhosphonate-4O-mU]; wherein positions 1-20 of the antisense strand form a duplex region with positions 1-20 of the sense strand, wherein positions 21-36 of the sense strand form a stem-loop, wherein positions 27-30 form the loop of the stem-loop, optionally wherein positions 27-30 comprise a tetraloop, wherein positions 21 and 22 of the antisense strand comprise an overhang, and wherein the sense strand comprises a sequence as set forth in SEQ ID NO: 21 and the antisense strand comprises a sequence as set forth in SEQ ID NO: 22.

In some embodiments, an XDH-targeting oligonucleotide for reducing XDH expression provided by the disclosure comprises a sense strand comprising the nucleotide sequence as set forth in SEQ ID NO: 21 and an antisense strand comprising the nucleotide sequence as set forth in SEQ ID NO: 22.

In some embodiments, the disclosure provides an oligonucleotide (e.g., an RNAi oligonucleotide) for reducing XDH expression, wherein the oligonucleotide comprises a sense strand and an antisense strand according to:

```
Sense Strand:
5'-[ademX-C22]-S-mX-mX-mX-mX-mX-mX-fX-fX-fX-fX-
mX-mX-mX-mX-mX-mX-mX-mX-mX-mX-mX-mX-mX-mX-mX-mX-
[ademX-GalNAc]-[ademX-GalNAc]-[ademX-GalNAc]-
mX-mX-mX-mX-mX-mX-3';
```

hybridized to:

```
Antisense Strand:
5'-[MePhosphonate-4O-mX]-S-fX-S-fX-S-fX-fX-mX-
fX-mX-mX-fX-mX-mX-mX-fX-mX-mX-mX-mX-mX-mX-S-
mX-S-mX-3';
```

wherein ademX-C22=C22 hydrocarbon chain conjugated to a nucleotide; mX=2'-O-methyl modified nucleotide, fX=2'-fluoro modified nucleotide, —S-=phosphorothioate linkage, -=phosphodiester linkage, [MePhosphonate-4O-mX]=4'-O-monomethylphosphonate-2'-O-methyluridine, and ademX-GalNAc=GalNAc attached to a nucleotide.

In some embodiments, the disclosure provides an RNAi oligonucleotide for reducing XDH expression, the oligonucleotide comprising a sense strand and an antisense strand, wherein the sense strand comprises the sequence and all of the modifications of 5' [ademCs-C22][mA][mG][mA][mA][mC][mA][fU][fG][fG][fA][mU][mC][mU][mA][mU][mU][mA][mA][mA][mG][mC][mA][mG][mC][mC][mG][ademA-GalNAc][ademA-GalNAc][ademA-GalNAc][mG][mG][mC][mU][mG][mC]3' (SEQ ID NO: 23) and wherein the antisense strand comprises the sequence and all of the modifications of 5' [MePhosphonate-4O-mUs] [fUs][fUs][fA][fA][mU][fA][mG][mA][fU][mC][mC][mA][fU][mG][mU][mU][mC][mU][mGs][mGs][mG]-3' (SEQ ID NO: 24), wherein mC, mA, mG, mU=2'-OMe ribonucleosides; fA, fC, fG, fU=2'F ribonucleosides; s=phosphorothioate; ademC5-C22=C22 hydrocarbon chain modified cytosine nucleotide; and ademA-GalNAc=GalNAc modified adenine nucleotide.

In some embodiments, the disclosure provides an oligonucleotide (e.g., an RNAi oligonucleotide) for reducing XDH expression, wherein the oligonucleotide comprises a sense strand and an antisense strand comprising nucleotide sequences selected from the group consisting of:

(a) the sense strand comprises a sequence as set forth in SEQ ID NO: 3 and the antisense strand comprises a sequence as set forth in SEQ ID NO: 4;
(b) the sense strand comprises a sequence as set forth in SEQ ID NO: 7 and the antisense strand comprises a sequence as set forth in SEQ ID NO: 8;
(c) the sense strand comprises a sequence as set forth in SEQ ID NO: 11 and the antisense strand comprises a sequence as set forth in SEQ ID NO: 12;
(d) the sense strand comprises a sequence as set forth in SEQ ID NO: 15 and the antisense strand comprises a sequence as set forth in SEQ ID NO: 16;
(e) the sense strand comprises a sequence as set forth in SEQ ID NO: 19 and the antisense strand comprises a sequence as set forth in SEQ ID NO: 20;
(f) the sense strand comprises a sequence as set forth in SEQ ID NO: 23 and the antisense strand comprises a sequence as set forth in SEQ ID NO: 24; and
(g) the sense strand comprises a sequence as set forth in SEQ ID NO: 27 and the antisense strand comprises a sequence as set forth in SEQ ID NO: 28.

In some embodiments, an XDH-targeting oligonucleotide for reducing XDH expression provided by the disclosure comprises a sense strand comprising the nucleotide sequence as set forth in SEQ ID NO: 23 and an antisense strand comprising the nucleotide sequence as set forth in SEQ ID NO: 24.

Formulations

Various formulations (e.g., pharmaceutical formulations) have been developed for oligonucleotide use. For example, oligonucleotides (e.g., RNAi oligonucleotides) can be delivered to a subject or a cellular environment using a formulation that minimizes degradation, facilitates delivery and/or uptake, or provides another beneficial property to the oligonucleotides in the formulation. In some embodiments, provided herein are compositions comprising oligonucleotides (e.g., RNAi oligonucleotides) reduce the expression of XDH. Such compositions can be suitably formulated such that when administered to a subject, either into the immediate environment of a target cell or systemically, a sufficient portion of the oligonucleotides enter the cell to reduce XDH expression. Any variety of suitable oligonucleotide formulations can be used to deliver oligonucleotides for the reduction of XDH as disclosed herein. In some embodiments, an oligonucleotide is formulated in buffer solutions such as phosphate buffered saline solutions, liposomes, micellar structures, and capsids. Any of the oligonucleotides described herein may be provided not only as nucleic acids, but also in the form of a pharmaceutically acceptable salt.

Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Accordingly, in some embodiments, a formulation comprises a lipid nanoparticle. In some embodiments, an excipient comprises a liposome, a lipid, a lipid complex, a microsphere, a microparticle, a nanosphere or a nanoparticle, or may be otherwise formulated for administration to the cells, tissues, organs, or body of a subject in need thereof (see, e.g., Remington: THE SCIENCE AND PRACTICE OF PHARMACY, 22nd edition, Pharmaceutical Press, 2013).

In some embodiments, the formulations herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol or polyvinylpyrrolidone) or a collapse temperature modifier (e.g., dextran, Ficoll™ or gelatin).

In some embodiments, a pharmaceutical composition is formulated to be compatible with its intended route of administration. Examples of routes of administration include parenteral (e.g., intravenous, intramuscular, intraperitoneal, intradermal, subcutaneous), oral (e.g., inhalation), transdermal (e.g., topical), transmucosal and rectal administration.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and liquid polyethylene glycol, and the like), and suitable mixtures thereof. In many cases, it will be preferable to include isotonic agents, for example, sugars, polyalcohols such as mannitol, sorbitol, sodium chloride in the composition. Sterile injectable solutions can be prepared by incorporating the oligonucleotides in a required amount in a selected solvent with one or a combination of ingredients enumerated above, as required, followed by filtered sterilization.

In some embodiments, a composition may contain at least about 0.1% of the therapeutic agent (e.g., a RNAi oligonucleotide for reducing XDH expression) or more, although the percentage of the active ingredient(s) may be between about 1% to about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Methods of Use

Reducing XDH Expression

In some embodiments, the disclosure provides methods for contacting or delivering to a cell or population of cells an effective amount of oligonucleotides provided herein (e.g., RNAi oligonucleotides) to reduce XDH expression. In some embodiments, a reduction of XDH expression is determined by measuring a reduction in the amount or level of XDH mRNA, XDH protein, or XDH activity in a cell. The methods include those described herein and known to one of ordinary skill in the art.

Methods provided herein are useful in any appropriate cell type. In some embodiments, a cell is any cell that expresses XDH mRNA (e.g., hepatocytes). In some embodiments, the cell is a primary cell obtained from a subject. In some embodiments, the primary cell has undergone a limited number of passages such that the cell substantially maintains its natural phenotypic properties. In some embodiments, a cell to which the oligonucleotide is delivered is ex vivo or in vitro (i.e., can be delivered to a cell in culture or to an organism in which the cell resides).

In some embodiments, the oligonucleotides herein (e.g., RNAi oligonucleotides) are delivered to a cell or population of cells using a nucleic acid delivery method known in the art including, but not limited to, injection of a solution containing the oligonucleotides, bombardment by particles covered by the oligonucleotides, exposing the cell or population of cells to a solution containing the oligonucleotides, or electroporation of cell membranes in the presence of the oligonucleotides. Other methods known in the art for delivering oligonucleotides to cells may be used, such as lipid-mediated carrier transport, chemical-mediated transport, and cationic liposome transfection such as calcium phosphate, and others.

In some embodiments, reduction of XDH expression is determined by an assay or technique that evaluates one or more molecules, properties, or characteristics of a cell or population of cells associated with XDH expression, or by an assay or technique that evaluates molecules that are directly indicative of XDH expression in a cell or population of cells (e.g., XDH mRNA or XDH protein). In some embodiments, the extent to which an oligonucleotide provided herein reduces XDH expression is evaluated by comparing XDH expression in a cell or population of cells contacted with the oligonucleotide to an appropriate control (e.g., an appropriate cell or population of cells not contacted with the oligonucleotide or contacted with a control oligonucleotide). In some embodiments, a control amount or level of XDH expression in a control cell or population of cells is predetermined, such that the control amount or level need not be measured in every instance the assay or technique is performed. The predetermined level or value can take a variety of forms. In some embodiments, a predetermined level or value can be single cut-off value, such as a median or mean.

In some embodiments, contacting or delivering an oligonucleotide described herein (e.g., an RNAi oligonucleotide) to a cell or a population of cells results in a reduction in XDH expression in a cell or population of cells not contacted with the oligonucleotide or contacted with a control oligonucleotide. In some embodiments, the reduction in XDH expression is about 1% or lower, about 5% or lower, about 10% or lower, about 15% or lower, about 20% or lower, about 25% or lower, about 30% or lower, about 35% or lower, about 40% or lower, about 45% or lower, about 50% or lower, about 55% or lower, about 60% or lower, about 70% or lower, about 80% or lower, or about 90% or lower relative to a control amount or level of XDH expression. In some embodiments, the control amount or level of XDH expression is an amount or level of XDH mRNA and/or XDH protein in a cell or population of cells that has not been contacted with an oligonucleotide herein. In some embodiments, XDH mRNA expression is measured using methods known in the art. In some embodiments, XDH mRNA expression is measured by qPCR. In some embodiments, XDH protein expression is measured using methods known in the art. In some embodiments XDH protein expression is measured by ELISA. In some embodiments, XDH protein expression is measured by western blot. In some embodiments, the effect of delivery of an oligonucleotide herein to a cell or population of cells according to a method herein is assessed after any finite period or amount of time (e.g., minutes, hours, days, weeks, months). For example, in some embodiments, XDH expression is determined in a cell or population of cells at least about 4 hours, about 8 hours, about 12 hours, about 18 hours, about 24 hours; or at least about 1 day, about 2 days, about 3 days, about 4 days, about 5 days, about 6 days, about 7 days, about 8 days, about 9 days, about 10 days, about 11 days, about 12 days, about 13 days, about 14 days, about 21 days, about 28 days, about 35 days, about 42 days, about 49 days, about 56 days, about 63 days, about 70 days, about 77 days, or about 84 days or more after contacting or delivering the oligonucleotide to the cell or population of cells. In some embodiments, XDH expression is determined in a cell or population of cells at least about 1 month, about 2 months, about 3 months, about 4 months, about 5 months, or about 6 months or more after contacting or delivering the oligonucleotide to the cell or population of cells.

In some embodiments, an oligonucleotide provided herein (e.g., an RNAi oligonucleotide) is delivered in the form of a transgene that is engineered to express in a cell the oligonucleotide or strands comprising the oligonucleotide (e.g., its sense and antisense strands). In some embodiments, an oligonucleotide herein is delivered using a transgene engineered to express any oligonucleotide disclosed herein. Transgenes may be delivered using viral vectors (e.g., adenovirus, retrovirus, vaccinia virus, poxvirus, adeno-associated virus, or herpes simplex virus) or non-viral vectors (e.g., plasmids or synthetic mRNAs). In some embodiments, transgenes can be injected directly to a subject.

Treatment Methods

The disclosure provides oligonucleotides (e.g., RNAi oligonucleotides) for use as a medicament, in particular for use in a method for the treatment of diseases, disorders, and conditions associated with expression of XDH. The disclosure also provides oligonucleotides for use, or adaptable for use, to treat a subject (e.g., a human having a disease, disorder or condition associated with XDH expression) that would benefit from reducing XDH expression. In some respects, the disclosure provides oligonucleotides for use, or adapted for use, to treat a subject having a disease, disorder or condition associated with expression of XDH. The disclosure also provides oligonucleotides for use, or adaptable for use, in the manufacture of a medicament or pharmaceutical composition for treating a disease, disorder or condition associated with XDH expression. In some embodiments, the oligonucleotides for use, or adaptable for use, target XDH mRNA and reduce XDH expression (e.g., via the RNAi pathway). In some embodiments, the oligonucleotides for use, or adaptable for use, target XDH mRNA and reduce the amount or level of XDH mRNA, XDH protein and/or XDH activity.

In addition, in some embodiments of the methods herein, a subject having a disease, disorder, or condition associated with XDH expression or is predisposed to the same is selected for treatment with an oligonucleotide provided herein (e.g., an RNAi oligonucleotide). In some embodiments, the method comprises selecting an individual having a marker (e.g., a biomarker) for a disease, disorder, or condition associated with XDH expression or predisposed to the same, such as, but not limited to, XDH mRNA, XDH protein, or a combination thereof. Likewise, and as detailed below, some embodiments of the methods provided by the disclosure include steps such as measuring or obtaining a baseline value for a marker of XDH expression (e.g., XDH mRNA), and then comparing such obtained value to one or more other baseline values or values obtained after the subject is administered the oligonucleotide to assess the effectiveness of treatment.

The disclosure also provides methods of treating a subject having, suspected of having, or at risk of developing a disease, disorder or condition associated with XDH expression with an oligonucleotide provided herein. In some aspects, the disclosure provides methods of treating or attenuating the onset or progression of a disease, disorder or condition associated with XDH expression using the oligonucleotides herein. In other aspects, the disclosure provides methods to achieve one or more therapeutic benefits in a subject having a disease, disorder, or condition associated with XDH expression using the oligonucleotides provided herein. In some embodiments of the methods herein, the subject is treated by administering a therapeutically effective amount of any one or more of the oligonucleotides provided herein. In some embodiments, treatment comprises reducing XDH expression. In some embodiments, the subject is treated therapeutically. In some embodiments, the subject is treated prophylactically.

In some embodiments of the methods herein, one or more oligonucleotides herein (e.g., RNAi oligonucleotides), or a pharmaceutical composition comprising one or more oligonucleotides, is administered to a subject having a disease, disorder or condition associated with XDH expression such that XDH expression is reduced in the subject, thereby treating the subject. In some embodiments, an amount or level of XDH mRNA is reduced in the subject. In some embodiments, an amount or level of XDH protein is reduced in the subject. In some embodiments, an amount or level of XDH activity is reduced in the subject.

In some embodiments of the methods herein, an oligonucleotide provided herein (e.g., an RNAi oligonucleotide), or a pharmaceutical composition comprising the oligonucleotide, is administered to a subject having a disease, disorder or condition associated with XDH such that XDH expression is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to XDH expression prior to administration of one or more oligonucleotides or pharmaceutical composition. In some embodiments, XDH expression is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to XDH expression in a subject (e.g., a reference or control subject) not receiving the oligonucleotide or oligonucleotides or pharmaceutical composition or receiving a control oligonucleotide or oligonucleotides, pharmaceutical composition or treatment.

In some embodiments of the methods herein, an oligonucleotide or oligonucleotides herein (e.g., RNAi oligonucleotides), or a pharmaceutical composition comprising the oligonucleotide or oligonucleotides, is administered to a subject having a disease, disorder or condition associated with XDH expression such that an amount or level of XDH mRNA is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of XDH mRNA prior to administration of the oligonucleotide or pharmaceutical composition. In some embodiments, an amount or level of XDH mRNA is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of XDH mRNA in a subject (e.g., a reference or control subject) not receiving the oligonucleotide or oligonucleotides or pharmaceutical composition or receiving a control oligonucleotide or oligonucleotides, pharmaceutical composition or treatment.

In some embodiments of the methods herein, an oligonucleotide or oligonucleotides herein, or a pharmaceutical composition comprising the oligonucleotide or oligonucleotides, is administered to a subject having a disease, disorder or condition associated with XDH expression such that an amount or level of XDH protein is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of XDH protein prior to administration of the oligonucleotide or pharmaceutical composition. In some embodiments, an amount or level of XDH protein is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of XDH protein in a subject (e.g., a reference or control subject) not receiving the oligonucleotide or oligonucleotides or pharmaceutical composition or receiving a control oligonucleotide, oligonucleotides or pharmaceutical composition or treatment.

In some embodiments of the methods herein, an oligonucleotide or oligonucleotides (e.g., RNAi oligonucleotides) herein, or a pharmaceutical composition comprising the oligonucleotide or oligonucleotides, is administered to a subject having a disease, disorder or condition associated with XDH such that an amount or level of XDH gene activity/expression is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of XDH activity prior to administration of the oligonucleotide or pharmaceutical composition. In some embodiments, an amount or level of XDH activity is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of XDH activity in a subject (e.g., a reference or control subject) not receiving the oligonucleotide or pharmaceutical composition or receiving a control oligonucleotide, pharmaceutical composition or treatment.

Suitable methods for determining XDH expression, the amount or level of XDH mRNA, XDH protein, XDH activity, or a biomarker related to or affected by modulation of XDH expression (e.g., a plasma biomarker), in the subject, or in a sample from the subject, are known in the art. Further, the Examples set forth herein illustrate methods for determining XDH expression.

In some embodiments, XDH expression, the amount or level of XDH mRNA, XDH protein, XDH activity, or a biomarker related to or affected by modulation of XDH expression, or any combination thereof, is reduced in a cell (e.g., a hepatocyte), a population or a group of cells (e.g., an organoid), an organ (e.g., liver), blood or a fraction thereof (e.g., plasma), a tissue (e.g., liver tissue), a sample (e.g., a liver biopsy sample), or any other appropriate biological material obtained or isolated from the subject. In some embodiments, XDH expression, the amount or level of XDH mRNA, XDH protein, XDH activity, or a biomarker related to or affected by modulation of XDH expression, or any combination thereof, is reduced in more than one type of cell (e.g., a hepatocyte and one or more other type(s) of cell), more than one groups of cells, more than one organ (e.g., liver and one or more other organ(s)), more than one fraction of blood (e.g., plasma and one or more other blood fraction (s)), more than one type of tissue (e.g., liver tissue and one or more other type(s) of tissue), or more than one type of sample (e.g., a liver biopsy sample and one or more other type(s) of biopsy sample).

Because of their high specificity, the oligonucleotides provided herein (e.g., RNAi oligonucleotides) specifically target mRNA of target genes (e.g., XDH mRNA) of cells and tissue(s), or organs(s) (e.g., in the liver). In preventing disease, the target gene may be one which is required for initiation or maintenance of the disease or which has been identified as being associated with a higher risk of contracting the disease. In treating disease, the oligonucleotide can be brought into contact with the cells, tissue(s), or organ(s) (e.g., liver) exhibiting or responsible for mediating the disease. For example, an oligonucleotide (e.g., an RNAi oligonucleotide) substantially identical to all or part of a wild-type (i.e., native) or mutated gene associated with a disorder or condition associated with XDH expression may be brought into contact with or introduced into a cell or tissue type of interest such as a hepatocyte or other liver cell.

Examples of a disease, disorder or condition associated with XDH expression include, but are not limited to hyperuricemia and gout.

In some embodiments, the target gene may be a target gene from any mammal, such as a human target. Any target gene may be silenced according to the method described herein.

Methods described herein typically involve administering to a subject an effective amount of an oligonucleotide herein (e.g., a RNAi oligonucleotide), that is, an amount that produces or generates a desirable therapeutic result. A therapeutically acceptable amount may be an amount that therapeutically treats a disease or disorder. The appropriate dosage for any one subject will depend on certain factors, including the subject's size, body surface area, age, the composition to be administered, the active ingredient(s) in the composition, time and route of administration, general health, and other drugs being administered concurrently.

In some embodiments, a subject is administered any one of the compositions herein (e.g., a composition comprising an RNAi oligonucleotide described herein) either enterally (e.g., orally, by gastric feeding tube, by duodenal feeding tube, via gastrostomy or rectally), parenterally (e.g., subcutaneous injection, intravenous injection or infusion, intraarterial injection or infusion, intraosseous infusion, intramuscular injection, intracerebral injection, intracerebroventricular injection, intrathecal), topically (e.g., epicutaneous, inhalational, via eye drops, or through a mucous membrane), or by direct injection into a target organ (e.g., the liver of a subject). Typically, oligonucleotides herein are administered intravenously or subcutaneously.

In some embodiments, an oligonucleotide herein (e.g., an RNAi oligonucleotide), or a pharmaceutical composition comprising the oligonucleotide, is administered alone or in combination. In some embodiments, the oligonucleotides herein are administered in combination concurrently, sequentially (in any order), or intermittently. For example, two oligonucleotides may be co-administered concurrently. Alternatively, one oligonucleotide may be administered and followed any amount of time later (e.g., one hour, one day, one week or one month) by the administration of a second oligonucleotide.

In some embodiments, the subject to be treated is a human or non-human primate or other mammalian subject. Other exemplary subjects include domesticated animals such as dogs and cats; livestock such as horses, cattle, pigs, sheep, goats, and chickens; and animals such as mice, rats, guinea pigs, and hamsters.

Kits

In some embodiments, the disclosure provides a kit comprising an oligonucleotide herein (e.g., an RNAi oligonucleotide), and instructions for use. In some embodiments, the kit comprises an oligonucleotide herein, and a package insert containing instructions for use of the kit and/or any component thereof. In some embodiments, the kit comprises, in a suitable container, an oligonucleotide herein, one or more controls, and various buffers, reagents, enzymes and other standard ingredients well known in the art. In some embodiments, the container comprises at least one vial, well, test tube, flask, bottle, syringe, or other container means, into which the oligonucleotide is placed, and in some instances, suitably aliquoted. In some embodiments where an additional component is provided, the kit contains additional containers into which this component is placed. The kits can also include a means for containing the oligonucleotide and any other reagent in close confinement for commercial sale. Such containers may include injection or blow-molded plastic containers into which the desired vials are retained. Containers and/or kits can include labeling with instructions for use and/or warnings.

In some embodiments, a kit comprises an oligonucleotide herein (e.g., an RNAi oligonucleotide), and a pharmaceutically acceptable carrier, or a pharmaceutical composition comprising the oligonucleotide and instructions for treating or delaying progression of a disease, disorder or condition associated with XDH expression in a subject in need thereof.

Definitions

As used herein, the term "antisense oligonucleotide" encompasses a nucleic acid-based molecule which has a sequence complementary to all or part of the target mRNA, in particular seed sequence thereby capable of forming a duplex with a mRNA. Thus, the term "antisense oligonucleotide", as used herein, may be referred to as "complementary nucleic acid-based inhibitor".

As used herein, "approximately" or "about," as applied to one or more values of interest, refers to a value that is similar to a stated reference value. In certain embodiments, "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1% or less in either direction (greater than or less than) of the stated reference value unless otherwise stated or otherwise evident from the context (except where such number would exceed 100% of a possible value).

As used herein, "administer," "administering," "administration" and the like refers to providing a substance (e.g., an oligonucleotide) to a subject in a manner that is pharmacologically useful (e.g., to treat a disease, disorder, or condition in the subject).

As used herein, "attenuate," "attenuating," "attenuation" and the like refers to reducing or effectively halting. As a non-limiting example, one or more of the treatments herein may reduce or effectively halt the onset or progression of hyperuricemia and/or gout. This attenuation may be exemplified by, for example, a decrease in one or more aspects (e.g., symptoms, tissue characteristics, and cellular, inflammatory, or immunological activity, etc.) of hyperuricemia and/or gout, no detectable progression (worsening) of one or more aspects of hyperuricemia and/or gout in a subject when they might otherwise be expected.

As used herein, "complementary" refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have regions of multiple nucleotides that are complementary with each other to form regions of complementarity, as described herein.

As used herein, "deoxyribonucleotide" refers to a nucleotide having a hydrogen in place of a hydroxyl at the 2' position of its pentose sugar when compared with a ribonucleotide. A modified deoxyribonucleotide is a deoxyribonucleotide having one or more modifications or substitutions of atoms other than at the 2' position, including modifications or substitutions in or of the sugar, phosphate group or base.

As used herein, "double-stranded oligonucleotide" or "ds oligonucleotide" refers to an oligonucleotide that is substantially in a duplex form. In some embodiments, the complementary base-pairing of duplex region(s) of a double-stranded oligonucleotide is formed between antiparallel sequences of nucleotides of covalently separate nucleic acid strands. In some embodiments, complementary base-pairing of duplex region(s) of a double-stranded oligonucleotide is formed between antiparallel sequences of nucleotides of nucleic acid strands that are covalently linked. In some embodiments, complementary base-pairing of duplex region(s) of a double-stranded oligonucleotide is formed from single nucleic acid strand that is folded (e.g., via a hairpin) to provide complementary antiparallel sequences of nucleotides that base pair together. In some embodiments, a double-stranded oligonucleotide comprises two covalently separate nucleic acid strands that are fully duplexed with one another. However, in some embodiments, a double-stranded oligonucleotide comprises two covalently separate nucleic acid strands that are partially duplexed (e.g., having overhangs at one or both ends). In some embodiments, a double-stranded oligonucleotide comprises antiparallel sequence of nucleotides that are partially complementary, and thus, may have one or more mismatches, which may include internal mismatches or end mismatches.

As used herein, "duplex," in reference to nucleic acids (e.g., oligonucleotides), refers to a structure formed through complementary base pairing of two antiparallel sequences of nucleotides.

As used herein, "excipient" refers to a non-therapeutic agent that may be included in a composition, for example, to provide or contribute to a desired consistency or stabilizing effect.

As used herein, "hepatocyte" or "hepatocytes" refers to cells of the parenchymal tissues of the liver. These cells make up about 70%-85% of the liver's mass and manufacture serum albumin, FBN and the prothrombin group of clotting factors (except for Factors 3 and 4). Markers for hepatocyte lineage cells include, but are not limited to, transthyretin (Ttr), glutamine synthetase (Glul), hepatocyte nuclear factor 1a (Hnf1a) and hepatocyte nuclear factor 4a (Hnf4a). Markers for mature hepatocytes may include, but are not limited to, cytochrome P450 (Cyp3a11), fumarylacetoacetate hydrolase (Fah), glucose 6-phosphate (G6p), albumin (Alb) and OC2-2F8. See, e.g., Huch et al. (2013) Nature 494:247-50.

As used herein, "hyperuricemia" refers to a medical condition characterized by elevated levels of uric acid in the blood. In certain instances, this condition arises due to increased uric acid production and/or reduced renal excretion of uric acid. Hyperuricemia may lead to the formation of urate crystals, which can lead to various health issues including gout and renal disorders.

As used herein, "gout" refers to a form of inflammatory arthritis caused by the deposition of monosodium urate crystals in joints, tissues, or other bodily fluids. In certain instances, this condition is related to an inherited abnormality in the body's ability to process uric acid. In some aspects, gout is associated with hyperuricemia and characterized by sudden and severe pain, redness, warmth, and swelling in affected joints. Gout can lead to chronic arthropathy and is typically managed through medications aimed at reducing uric acid levels and controlling inflammation.

As used herein, the term "XDH" refers to Xanthine dehydrogenase. XDH is a protein which belongs to the group of molybdenum-containing hydroxylases involved in the oxidative metabolism of purines. "XDH" may also refer to the gene which encodes the protein.

As used herein, "labile linker" refers to a linker that can be cleaved (e.g., by acidic pH). A "fairly stable linker" refers to a linker that cannot be cleaved.

As used herein, "modified internucleotide linkage" refers to an internucleotide linkage having one or more chemical modifications when compared with a reference internucleotide linkage comprising a phosphodiester bond. In some embodiments, a modified nucleotide is a non-naturally occurring linkage. Typically, a modified internucleotide linkage confers one or more desirable properties to a nucleic acid in which the modified internucleotide linkage is present. For example, a modified internucleotide linkage may improve thermal stability, resistance to degradation, nuclease resistance, solubility, bioavailability, bioactivity, reduced immunogenicity, etc.

As used herein, "modified nucleotide" refers to a nucleotide having one or more chemical modifications when compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide and thymidine deoxyribonucleotide. In some embodiments, a modified nucleotide is a non-naturally occurring nucleotide. In some embodiments, a modified nucleotide has one or more chemical modification in its sugar, nucleobase and/or phosphate group. In some embodiments, a modified nucleotide has one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc.

As used herein, "nicked tetraloop structure" refers to a structure of a RNAi oligonucleotide that is characterized by separate sense (passenger) and antisense (guide) strands, in which the sense strand has a region of complementarity with the antisense strand, and in which at least one of the strands, generally the sense strand, has a tetraloop configured to stabilize an adjacent stem region formed within the at least one strand.

As used herein, "oligonucleotide" refers to a short nucleic acid (e.g., less than about 100 nucleotides in length). An oligonucleotide may be single-stranded (ss) or double-stranded (ds). An oligonucleotide may comprise deoxyribonucleosides, ribonucleosides, or a combination of both. In some embodiments, a double-stranded oligonucleotide comprising ribonucleosides is referred to as "dsRNA". An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (DsiRNA), antisense oligonucleotide, short siRNA or ss siRNA.

As used herein, "overhang" refers to terminal non-base pairing nucleotide(s) resulting from one strand or region extending beyond the terminus of a complementary strand with which the one strand or region forms a duplex. In some embodiments, an overhang comprises one or more unpaired nucleotides extending from a duplex region at the 5' terminus or 3' terminus of an oligonucleotide. In certain embodiments, the overhang is a 3' or 5' overhang on the antisense strand or sense strand of an oligonucleotide.

As used herein, "phosphate analog" refers to a chemical moiety that mimics the electrostatic and/or steric properties of a phosphate group. In some embodiments, the phosphate analog mimics the electrostatic and/or steric properties of a phosphate group in biologic systems. In some embodiments, a phosphate analog is positioned at the 5' terminal nucleotide of an oligonucleotide in place of a 5'-phosphate, which is often susceptible to enzymatic removal. In some embodiments, a 5' phosphate analog contains a phosphatase-resistant linkage. Examples of phosphate analogs include, but are not limited to, 5' phosphonates, such as 5' methylene phosphonate (5'-MP) and 5'-(E)-vinylphosphonate (5'-VP). In some embodiments, an oligonucleotide has a phosphate analog at a 4'-carbon position of the sugar (referred to as a "4'-phosphate analog") at a 5'-terminal nucleotide. An example of a 4'-phosphate analog is oxymethyl phosphonate, in which the oxygen atom of the oxymethyl group is bound to the sugar moiety (e.g., at its 4'-carbon) or analog thereof. See, e.g., US Patent Publication No. 2019-0177729. Other modifications have been developed for the 5' end of oligonucleotides (see, e.g., Intl. Patent Application No. WO 2011/133871; U.S. Pat. No. 8,927,513; and Prakash et al. (2015) NUCLEIC ACIDS RES. 43:2993-3011).

As used herein, "reduced expression" of a gene (e.g., XDH) refers to a decrease in the amount or level of RNA transcript (e.g., XDH mRNA) or protein encoded by the gene and/or a decrease in the amount or level of activity of the gene in a cell, a population of cells, a sample, or a subject, when compared to an appropriate reference (e.g., a reference cell, population of cells, sample or subject). For example, the act of contacting a cell with an oligonucleotide herein (e.g., an oligonucleotide comprising an antisense strand having a nucleotide sequence that is complementary to a nucleotide sequence comprising XDH mRNA) may result in a decrease in the amount or level of XDH mRNA, protein and/or activity (e.g., via degradation of XDH mRNA by the RNAi pathway) when compared to a cell that is not treated with the oligonucleotide. Similarly, and as used herein, "reducing expression" refers to an act that results in reduced expression of a gene (e.g., XDH).

As used herein, "reduction of XDH expression" refers to a decrease in the amount or level of XDH mRNA, XDH protein and/or XDH activity in a cell, a population of cells, a sample or a subject when compared to an appropriate reference (e.g., a reference cell, population of cells, sample, or subject).

As used herein, "region of complementarity" refers to a sequence of nucleotides of a nucleic acid (e.g., an oligonucleotide) that is sufficiently complementary to an antiparallel sequence of nucleotides to permit hybridization between the two sequences of nucleotides under appropriate hybridization conditions (e.g., in a phosphate buffer, in a cell, etc.). In some embodiments, an oligonucleotide herein comprises a targeting sequence having a region of complementary to a mRNA target sequence.

As used herein, "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

As used herein, "RNAi oligonucleotide" refers to a double-stranded oligonucleotide having a sense strand (passenger) and antisense strand (guide), in which the antisense strand or part of the antisense strand is used by the Argonaute 2 (Ago2) endonuclease in the cleavage of a target mRNA (e.g., XDH mRNA).

As used herein, "strand" refers to a single, contiguous sequence of nucleotides linked together through internucleotide linkages (e.g., phosphodiester linkages or phosphorothioate linkages). In some embodiments, a strand has two free ends (e.g., a 5' end and a 3' end).

As used herein, "subject" means any mammal, including mice, rabbits, non-human primates (NHP), and humans. In one embodiment, the subject is a human or NHP. Moreover, "individual" or "patient" may be used interchangeably with "subject."

As used herein, "synthetic" refers to a nucleic acid or other molecule that is artificially synthesized (e.g., using a machine (e.g., a solid-state nucleic acid synthesizer)) or that is otherwise not derived from a natural source (e.g., a cell or organism) that normally produces the molecule.

As used herein, "targeting ligand" refers to a molecule (e.g., a carbohydrate, amino sugar, cholesterol, polypeptide, or lipid) that selectively binds to a cognate molecule (e.g., a receptor) of a tissue or cell of interest and that is conjugatable to another substance for purposes of targeting the other substance to the tissue or cell of interest. For example, in some embodiments, a targeting ligand may be conjugated to an oligonucleotide for purposes of targeting the oligonucleotide to a specific tissue or cell of interest. In some embodiments, a targeting ligand selectively binds to a cell surface receptor. Accordingly, in some embodiments, a targeting ligand when conjugated to an oligonucleotide facilitates delivery of the oligonucleotide into a particular cell through selective binding to a receptor expressed on the surface of the cell and endosomal internalization by the cell of the complex comprising the oligonucleotide, targeting ligand and receptor. In some embodiments, a targeting ligand is conjugated to an oligonucleotide via a linker that is cleaved following or during cellular internalization such that the oligonucleotide is released from the targeting ligand in the cell.

As used herein, "target sequence" refers to a contiguous portion of the nucleotide sequence of an mRNA molecule formed during the transcription of an XDH gene (e.g., the sequence set forth in NM_000379.4) including mRNA that is a product of RNA processing of a primary transcription product. In some embodiments, the target portion of the sequence will be at least long enough to serve as a substrate for RNAi-directed cleavage at or near that portion of the nucleotide sequence of an mRNA molecule formed during the transcription of an XDH gene. In some embodiments, the target sequence is within the protein coding region of the XDH gene. In some embodiments, the target sequence is within the 3' UTR of the XDH gene.

As used herein, "targeting sequence" refers to a nucleotide sequence that is fully or partially complementary to a target sequence.

As used herein, "loop", or "tetraloop" refers to an unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cell), the two antiparallel regions, which flank the unpaired region, hybridize to form a duplex (referred to as a "stem"). A loop that increases stability of an adjacent duplex formed by hybridization of flanking sequences of nucleotides. The increase in stability is detectable as an increase in melting temperature ($T_m$) of an adjacent stem duplex that is higher than the $T_m$ of the adjacent stem duplex expected, on average, from a set of loops of comparable length consisting of randomly selected sequences of nucleotides. For example, a loop (e.g. a tetraloop) can confer a $T_m$ of at least about 50° C., at least about 55° C., at least about 56° C., at least about 58° C., at least about 60° C., at least about 65° C. or at least about 75° C. in 10 mM $Na_2HPO_4$ to a hairpin comprising a duplex of at least 2 base pairs (bp) in length. In some embodiments, a tetraloop can confer a Tm of at least about 50° C., at least about 55° C., at least about 56° C., at least about 58° C., at least about 60° C., at least about 65° C. or at least about 75° C. in 10 mM $NaH_2PO_4$ to a hairpin comprising a duplex of at least 2 base pairs (bp) in length. In some embodiments, a loop may stabilize a bp in an adjacent stem duplex by stacking interactions. In addition, interactions among the nucleotides in a loop include, but are not limited to, non-Watson-Crick base pairing, stacking interactions, hydrogen bonding and contact interactions (Cheong et al. (1990) Nature 346:680-82; Heus & Pardi (1991) Science 253:191-94). In some embodiments, a loop comprises or consists of 3 to 6 nucleotides and is typically 4 to 5 nucleotides. In certain embodiments, a tetraloop comprises or consists of 3, 4, 5 or 6 nucleotides, which may or may not be modified (e.g., which may or may not be conjugated to a targeting moiety). In one embodiment, a loop consisting of 4 nucleotides is a tetraloop. Any nucleotide may be used in the loop and standard IUPAC-IUB symbols for such nucleotides may be used as described in Cornish-Bowden (1985) Nucleic Acids Res. 13:3021-30. For example, the letter "N" may be used to mean that any base may be in that position, the letter "R" may be used to show that A (adenine) or G (guanine) may be in that position, and "B" may be used to show that C (cytosine), G (guanine), or T (thymine) may be in that position. Examples of tetraloops include the UNCG family of tetraloops (e.g., UUCG), the GNRA family of tetraloops (e.g., GAAA), and the CUUG tetraloop (Woese et al. (1990) Proc. Natl. Acad. Sci. Usa 87:8467-71; Antao et al. (1991) Nucleic Acids Res. 19:5901-05). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, and the d(TNCG) family of tetraloops (e.g., d(TTCG)). See, e.g., Nakano et al. (2002) Biochem. 41:14281-92; Shinji et al. (2000) Nippon Kagakkai Koen Yokoshu 78:731. In some embodiments, the tetraloop is contained within a nicked tetraloop structure.

As used herein, "treat" or "treating" refers to the act of providing care to a subject in need thereof, for example, by administering a therapeutic agent (e.g., an oligonucleotide herein) to the subject, for purposes of improving the health and/or well-being of the subject with respect to an existing condition (e.g., a disease, disorder) or to prevent or decrease the likelihood of the occurrence of a condition. In some embodiments, treatment involves reducing the frequency or severity of at least one sign, symptom or contributing factor of a condition (e.g., disease, disorder) experienced by a subject.

EXAMPLES

Example 1: Reduction of Serum Urate with Murine XDH Targeting RNAi Oligonucleotides Hyperuricemia occurs when there is an excess of urate, or uric acid, in the blood. Accumulation of urate crystals can cause diseases such as gout. Urate is a product of purine metabolism. The gene for uricase (UOX) in higher primates, including humans, does not produce a functional protein and thus they rely on renal/gastrointestinal elimination of urate rather than the more readily excretable allantoin. Xanthine oxidase (XO) and xanthine dehydrogenase (XDH) are interconvertible forms of the same enzyme, known as xanthine oxidoreductase, and primarily degrade purines and convert hypoxanthine to xanthine and xanthine to uric acid. Accordingly, RNAi oligonucleotides targeting XDH were developed to reduce conversion to uric acid.

As mice retained the Uox gene, to establish a model of hyperuricemia the Uox gene was silenced in obese mice (ob/ob UOX KD) via a UOX targeting RNAi oligonucleotide. This mouse model provided robust urate elevation without nephrotoxicity (data not shown) and was utilized to evaluate RNAi oligonucleotides targeting murine Xdh. Specifically, three RNAi oligonucleotides were developed, each having an antisense strand of 22 nucleotides and a sense strand of 36 nucleotides with a tetraloop. The sequences are shown in FIG. 1A and comprise a sense strand and antisense strand having of the sequences of SEQ ID NOs: 30 and 31, respectively, SEQ ID Nos: 32 and 33, respectively, and SEQ ID Nos: 34 and 35, respectively. The impact of different conjugation approaches were evaluated: (i) conjugation of a C22 hydrocarbon chain to a nucleotide of the tetraloop; (ii) conjugation of three GalNAc molecules on individual nucleotides of the tetraloop; and (iii) conjugation of a C22 hydrocarbon chain to the 5' nucleotide of the sense strand, and conjugation of three GalNAc molecules on individual nucleotides of the tetraloop (referred to as "dual C22/GalNAc conjugate").

To investigate the efficacy of differently conjugated XDH RNAi oligonucleotides, C57bl/6J wild type (WT) mice (n=6) and ob/ob mice (n=7-8) were subcutaneously administered 50 mg/kg UOX RNAi oligonucleotide alone or in combination with a single 30 mg/kg dose of the XDH RNAi oligonucleotides of FIG. 1A on Day 0. On Day 14 ob/ob UOX KD mice were administered a second dose of UOX RNAi oligonucleotide (15 mg/kg). PBS-treated mice were used as controls.

Figure 1B:
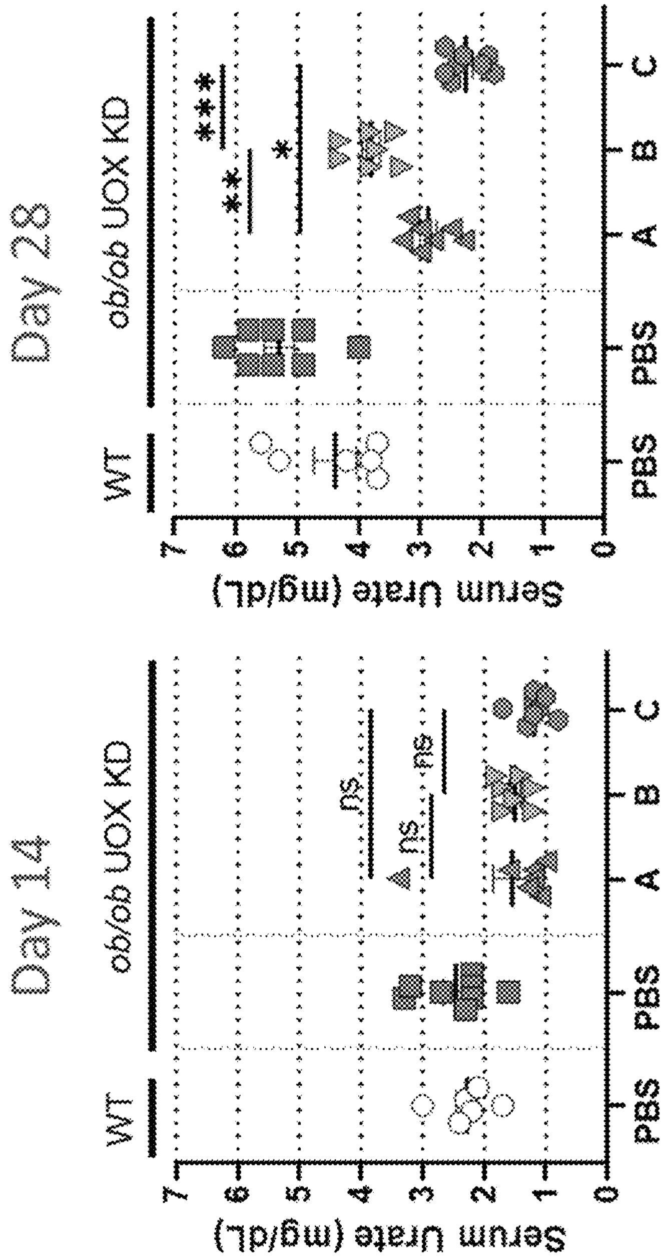
FIG. 1B provides graphs showing serum urate acid concentration (mg/dL) measured in the livers of wild-type (WT) mice or an obese mouse model of hyperuricemia based on Uox knockdown ("ob/ob UOX KD"). Livers were collected and evaluated for serum urate acid concentration 14 or 28 days after subcutaneous administration of 30 mg/kg of the RNAi oligonucleotides of FIG. 1A.

Serum urate levels were measured at Days 14 and 28. Results are provided in FIG. 1B. On Day 14, the average serum urate levels between single or dual-conjugated XDH RNAi oligonucleotides showed no significant differences. However, at Day 28, significant differences in reduction of serum urate levels were observed between conjugated XDH RNAi oligonucleotides. Specifically, the dual C22/GalNAc-conjugate demonstrated improved efficacy in reducing serum urate levels relative to the single-conjugated XDH RNAi oligonucleotides.

Example 2: Development of RNAi Oligonucleotides Targeting Human XDH

Based on the finding in Example 1 that RNAi oligonucleotides targeting murine XDH could reduce serum urate levels in the ob/ob UOX KD hyperuricemia model, RNAi oligonucleotides targeting human XDH were developed. Specifically, to develop RNAi oligonucleotides targeting human XDH, a computer-based algorithm was used to computationally identify XDH mRNA target sequences predicted to silence XDH expression by the RNAi pathway. The algorithm provided RNAi oligonucleotide guide (antisense) strand sequences each having a region of complementarity to a suitable XDH target sequence of human XDH mRNA (e.g., the sequence set forth in NM_000379.4). Some of the guide strand sequences identified by the algorithm were also complementary to the corresponding XDH target sequence of monkey XDH mRNA (the sequences set forth in XM_005576183.4 and XM_005576184.4).

RNAi oligonucleotides (formatted as DsiRNA oligonucleotides) were generated for evaluation in vitro. Each DsiRNA was generated with the same modification pattern shown below (X—any nucleotide; m—2'-O-methyl modified nucleotide; r—ribosyl modified nucleotide):

```
Sense Strand:
rXmXrXmXrXrXrXrXrXrXrXrXmXrXmXrXrXrXrXrXrXXX

Antisense Strand:
mXmXmXmXrXrXrXrXrXrXmXrXmXrXrXrXrXrXrXrXrXmXrXm
XmXmX
```

Each DsiRNA included a unique guide strand having a region of complementarity to an XDH target sequence identified by the algorithm. The ability of each of the modified DsiRNA to reduce XDH mRNA was measured using in vitro cell-based assays. Briefly, primary human hepatocytes expressing endogenous human XDH gene were transfected with the DsiRNAs at 1 nM in separate wells of a multi-well cell-culture plate. Cells were maintained for 24 hours following transfection with the modified DsiRNA, and then the amount of remaining XDH mRNA from the transfected cells was determined using TAQMAN®-based qPCR assays. XDH was assayed for % remaining RNA (data not shown).

Sequences were selected for evaluation in mice based on the in vitro screen to prepare double-stranded RNAi oligonucleotides comprising a nicked tetraloop GalNAc-conjugated structure having a 36-mer passenger strand and a 22-mer guide strand were generated. The nucleotide sequences comprising the passenger strand and guide strand of the XDH oligonucleotides have a distinct pattern of modified nucleotides and phosphorothioate linkages. The modification pattern is represented below:

```
Sense Strand:
[mXs][mX][mX][mX][mX][mX][mX][fX][fX][fX][fX]
[mX][mX][mX][mX][mX][mX][mX][mX][mX][mX][mX][mX]
[mX][mX][mX][mX][ademA-GalNAc][ademA-
GalNAc][ademA-GalNAc][mX][mX][mX][mX][mX][mX]
```

Hybridized to:

```
Antisense Strand:
[MePhosphonate-4O-mXs][fXs][fXs][fX][fX][mX][fX]
[mX][mX][fX][mX][mX][mX][fX][mX][mX][mX][mX][mX]
[mXs][mXs][mX]
(Modification key: Table 1).
```

TABLE 1

| Modification Key | |
|---|---|
| Symbol | Modification/linkage |
| [MePhosphonate-4O-mX] | 4'-O-monomethylphosphonate-2'-O-methyl modified nucleotide |
| [ademA-GalNAc] | GalNAc attached to an adenine nucleotide |
| [ademXs-C22] | C22 hydrocarbon chain conjugated a nucleotide with a phosphorothioate linkage to the neighboring nucleotide |
| [mXs] | 2'-O-methyl modified nucleotide with a phosphorothioate linkage to the neighboring nucleotide |
| [fXs] | 2'-fluoro modified nucleotide with a phosphorothioate linkage to the neighboring nucleotide |
| [mX] | 2'-O-methyl modified nucleotide |
| [fX] | 2'-fluoro modified nucleotide |

The GalNAc-conjugated XDH targeting RNAi oligonucleotides were used to evaluate inhibition efficacy in mice. Specifically, 6-8-week-old female CD-1 mice (n=5) were subcutaneously administered GalNAc-conjugated XDH oligonucleotides at a dose of 0.5 mg/kg or 1.0 mg/kg formulated in PBS. A control group of mice (n=5) were administered only PBS. Three days later (72 hours), the mice were hydrodynamically injected (HDI) with either a DNA plasmid (pCMV6-KHK-C, Cat #: RC223488, OriGene) encoding the full human XDH gene (NM_000379.4) (25 μg)) under control of a ubiquitous cytomegalovirus (CMV) promoter sequence. One day after introduction of the DNA plasmid, liver samples from HDI mice were collected.

Figure 2:
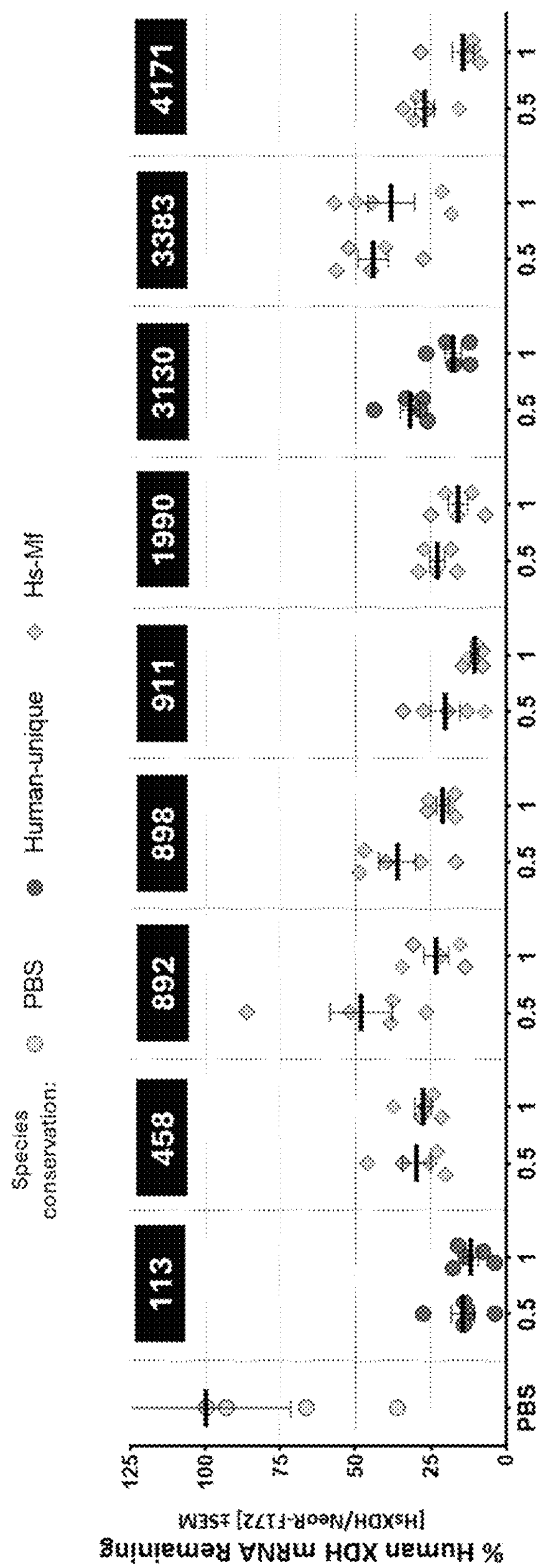
FIG. 2 provides a graph depicting the dose response of GalNAc-conjugated RNAi oligonucleotides targeting human XDH. The percent (%) of human XDH mRNA remaining in livers of mice exogenously expressing human XDH (HDI model) after treatment with GalNAc-conjugated XDH RNAi oligonucleotides at two different doses (0.5 mg/kg or 1 mg/kg) was measured. The levels of human XDH mRNA were determined from livers collected 4 days after injection with plasmid encoding human XDH. Hs/Mf=human/monkey common sequence.

Total RNA isolated from mouse livers were used to assess relative XDH mRNA expressions by qRT-PCR. The values were normalized for transfection efficiency using the NeoR gene included on the DNA plasmid. The results confirmed that GalNAc-conjugated XDH targeting RNAi oligonucleotides demonstrated successful knockdown of human XDH (FIG. 2). Based on these results, the following XDH targeting RNAi oligonucleotides were evaluated for further study: XDH-113; XDH-892; XDH-898; XDH-911; XDH-1990; XDH-4171; and XDH-4176.

Example 3: Evaluation of RNAi Oligonucleotides Targeting Human XDH in Non-Human Primates Based on the discovery in Example 1 that dual C22/GalNAc-conjugated RNAi oligonucleotides provided improved efficacy over single conjugated RNAi oligonucleotides, the RNAi oligonucleotides targeting human XDH identified in Example 2 were further evaluated in the dual C22/GalNAc-conjugate format in non-human primates (NHPs).

Figure 3:
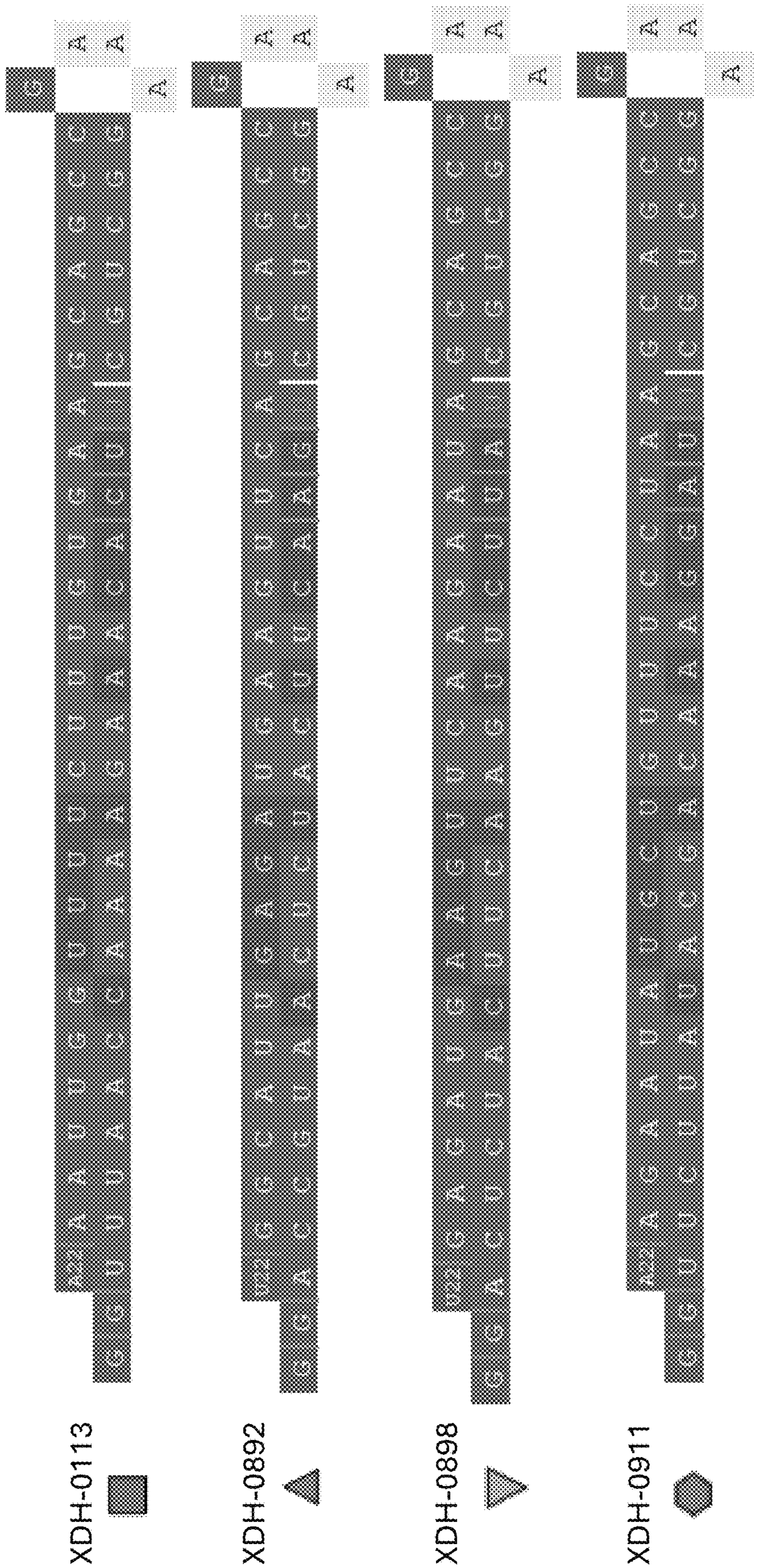
FIG. 3 provides schematics of dual C22/GalNAc-conjugated RNAi oligonucleotides evaluated in cynomolgus monkeys. The XDH-0113 RNAi oligonucleotide molecule comprises a modified sense strand and modified antisense strand having of the sequences of SEQ ID NOs: 3 and 4, respectively. The XDH-0892 RNAi oligonucleotide molecule comprises a modified sense strand and modified antisense strand having of the sequences of SEQ ID NOs: 7 and 8, respectively. The XDH-0898 RNAi oligonucleotide molecule comprises a modified sense strand and modified antisense strand having of the sequences of SEQ ID NOs: 11 and 12, respectively. The XDH-0911 RNAi oligonucleotide molecule comprises a modified sense strand and modified antisense strand having of the sequences of SEQ ID NOs: 15 and 16, respectively. The XDH-1990 RNAi oligonucleotide molecule comprises a modified sense strand and modified antisense strand having of the sequences of SEQ ID NOs: 19 and 20, respectively. The XDH-4171 RNAi oligonucleotide molecule comprises a modified sense strand and modified antisense strand having of the sequences of SEQ ID NOs: 23 and 24, respectively. The XDH-4176 RNAi oligonucleotide molecule comprises a modified sense strand and modified antisense strand having of the sequences of SEQ ID NOs: 27 and 28, respectively.
Figure 3:
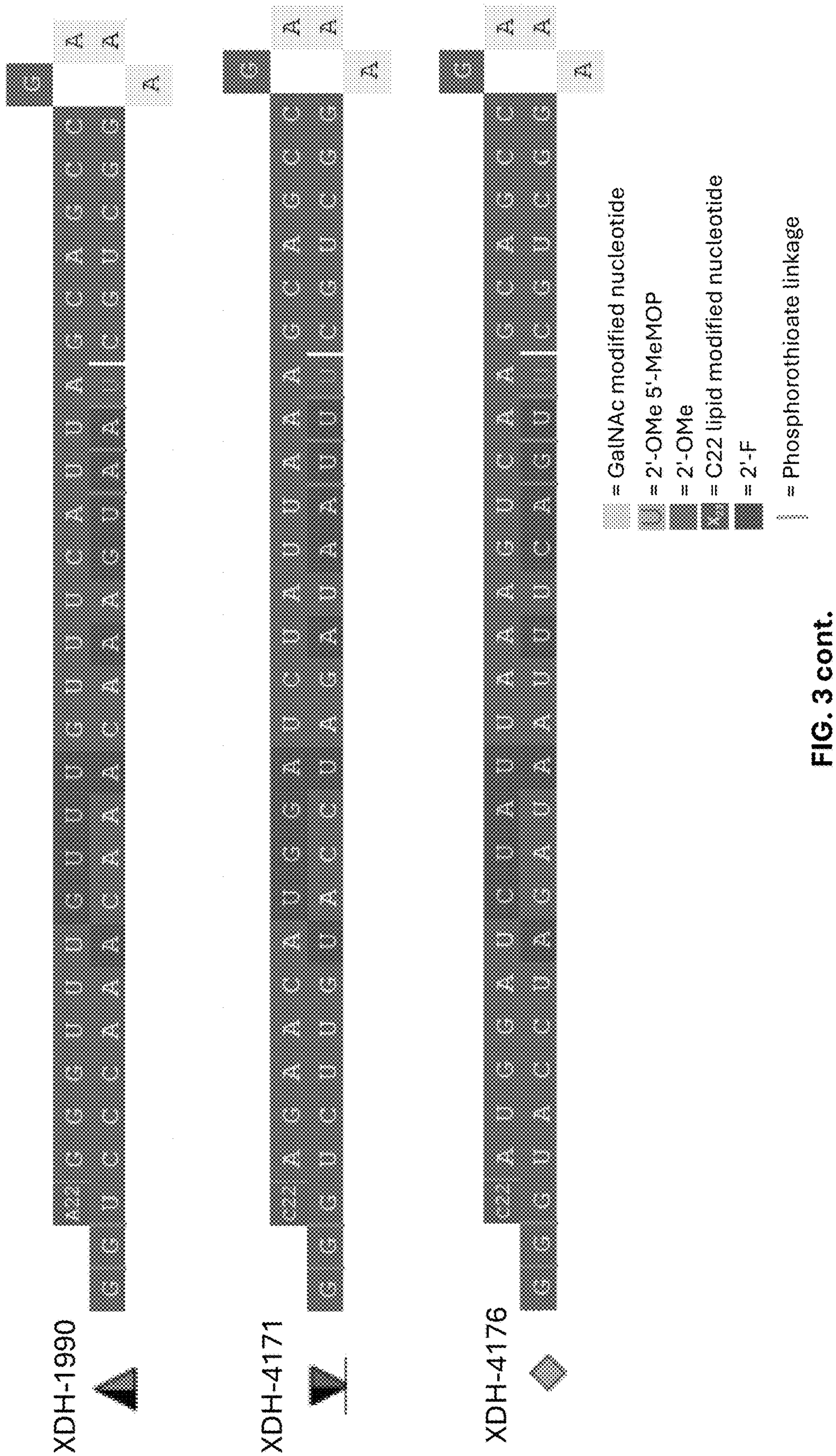

Specifically, the dual C22/GalNAc conjugated RNAi oligonucleotides provided in Table 2 and FIG. 3 were evaluated. The modification pattern evaluated is provided below (modification key in Table 1):

```
Sense strand:
[ademXs-C22][mX][mX][mX][mX][mX][mX][fX][fX]
[fX][fX][mX][mX][mX][mX][mX][mX][mX][mX][mX]
[mX][mX][X][mX][mX][mX][mX][ademA-
GalNAc][ademA-GalNAc][ademA-GalNAc][mX][mX]
[mX][mX][mX][mX]

Antisense strand:
[MePhosphonate-4O-mXs][fXs][fXs][fX][fX][mX]
[fX][mX][mX][fX][mX][mX][mX][fX][mX][mX][mX]
[mX][mX][mXs][mXs][mX]
```

TABLE 2

| RNAi Oligonucleotides for NHP Study | | | | |
|---|---|---|---|---|
| Name | Sense Strand Unmodified SEQ ID NO | Antisense Strand Unmodified SEQ ID NO | Sense Strand Modified SEQ ID NO | Antisense Strand Modified SEQ ID NO |
| XDH-0113 | 1 | 2 | 3 | 4 |
| XDH-0892 | 5 | 6 | 7 | 8 |
| XDH-0898 | 9 | 10 | 11 | 12 |
| XDH-0911 | 13 | 14 | 15 | 16 |
| XDH-1990 | 17 | 18 | 19 | 20 |
| XDH-4171 | 21 | 22 | 23 | 24 |
| XDH-4176 | 25 | 26 | 27 | 28 |

Figure 4:
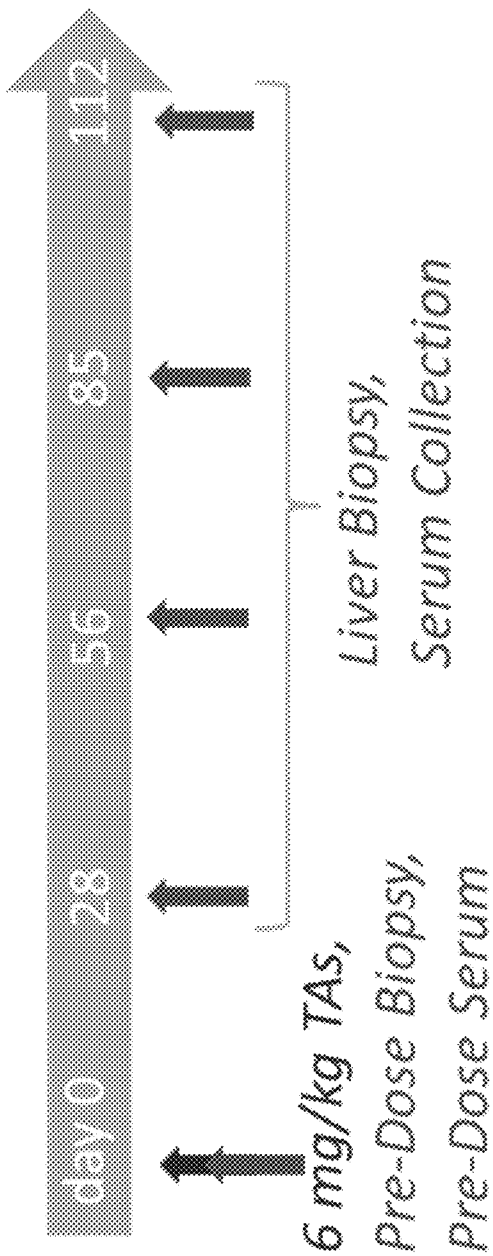
FIG. 4 provides a schematic of a non-human primate (NHP; Cynomolgus monkey) study design. The dual C22/GalNAc-conjugated XDH RNAi oligonucleotides of FIG. 3 were subcutaneously administered to the NHPs at 6 mg/kg on day 0. Liver and serum samples were collected at days 0, 28, 56, 85 and 112.
Figure 5A:
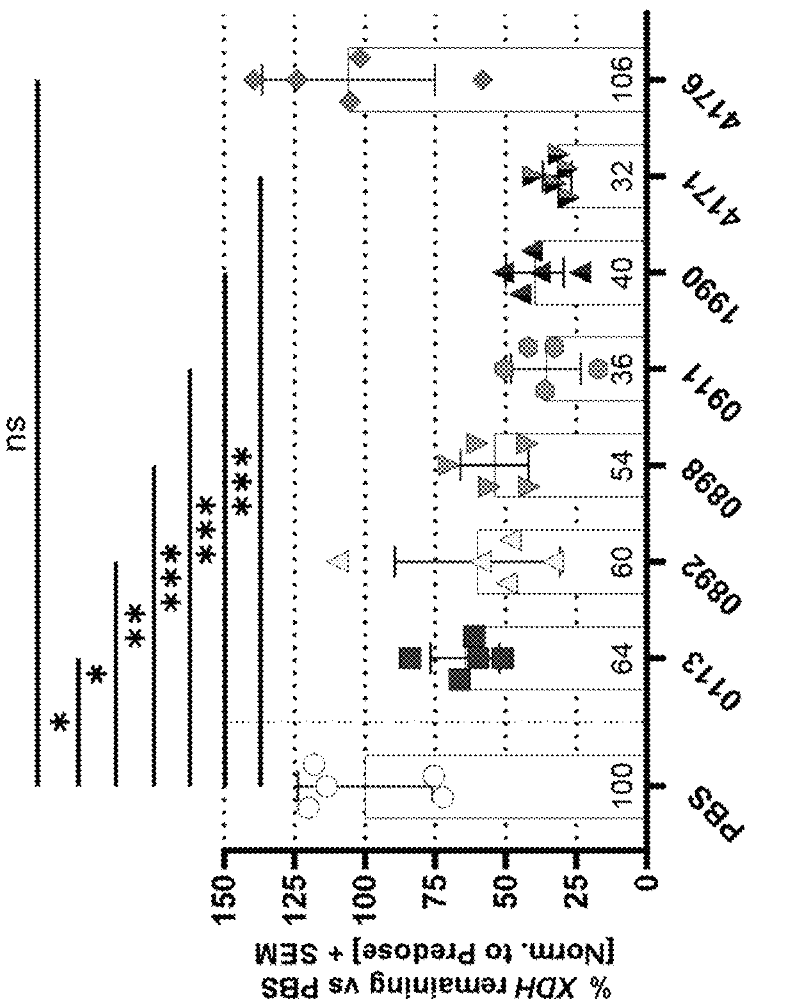
FIGS. 5A-5B show the amount of XDH mRNA (FIG. 5A) and xanthine oxidase (XO) protein (FIG. 5B) remaining in the liver of NHPs 28 days after administration of dual C22/GalNAc-conjugated XDH RNAi oligonucleotides based on the study design of FIG. 4. The percent (%) of XDH mRNA remaining in liver of NHPs 28 days after administration of the dual C22/GalNAc-conjugated XDH RNAi oligonucleotides is shown in FIG. 5A. The amount of XO protein remaining in liver of NHPs 28 days after administration of the dual C22/GalNAc-conjugated XDH RNAi oligonucleotides is shown in FIG. 5B.
Figure 5B:
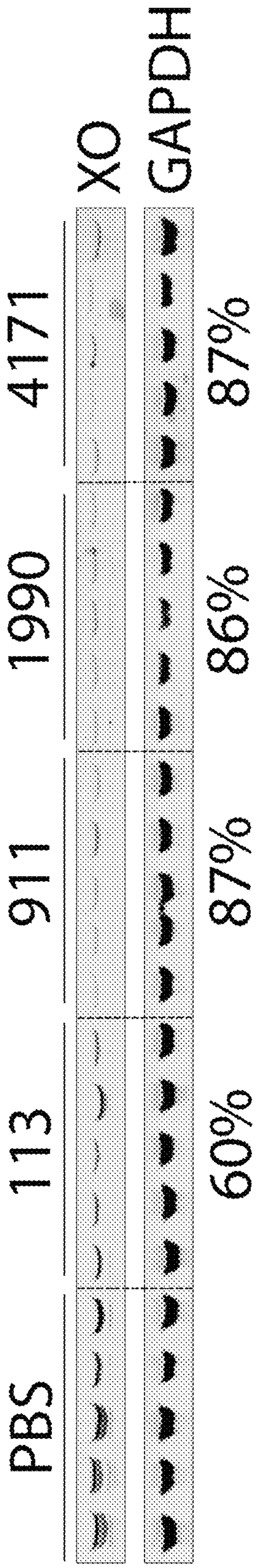
Figure 6A:
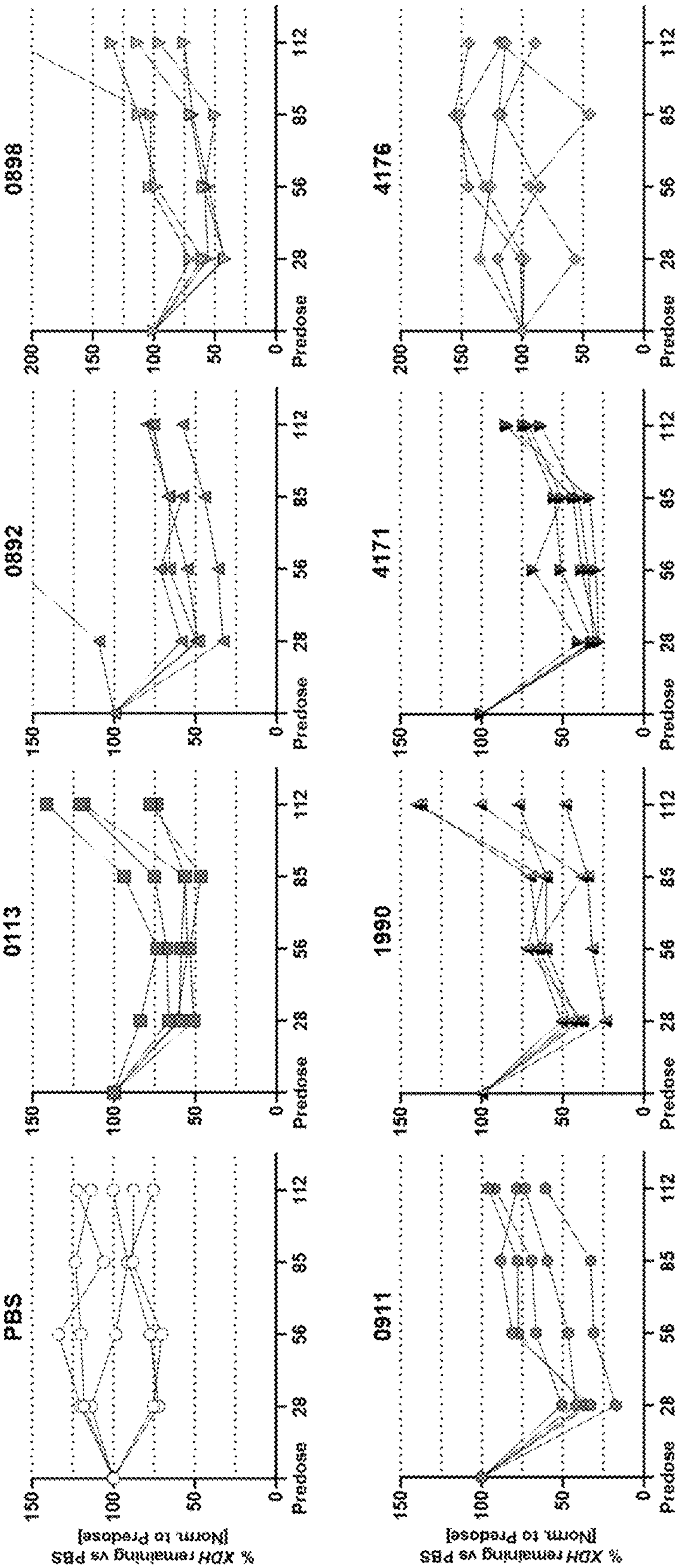
FIGS. 6A-6B provide line graphs showing the amount of XDH mRNA (FIG. 6A) and XO protein (FIG. 6B) remaining in the liver of NHPs administered the dual C22/GalNAc-conjugated XDH RNAi oligonucleotides throughout the study provided in FIG. 4.
Figure 6B:
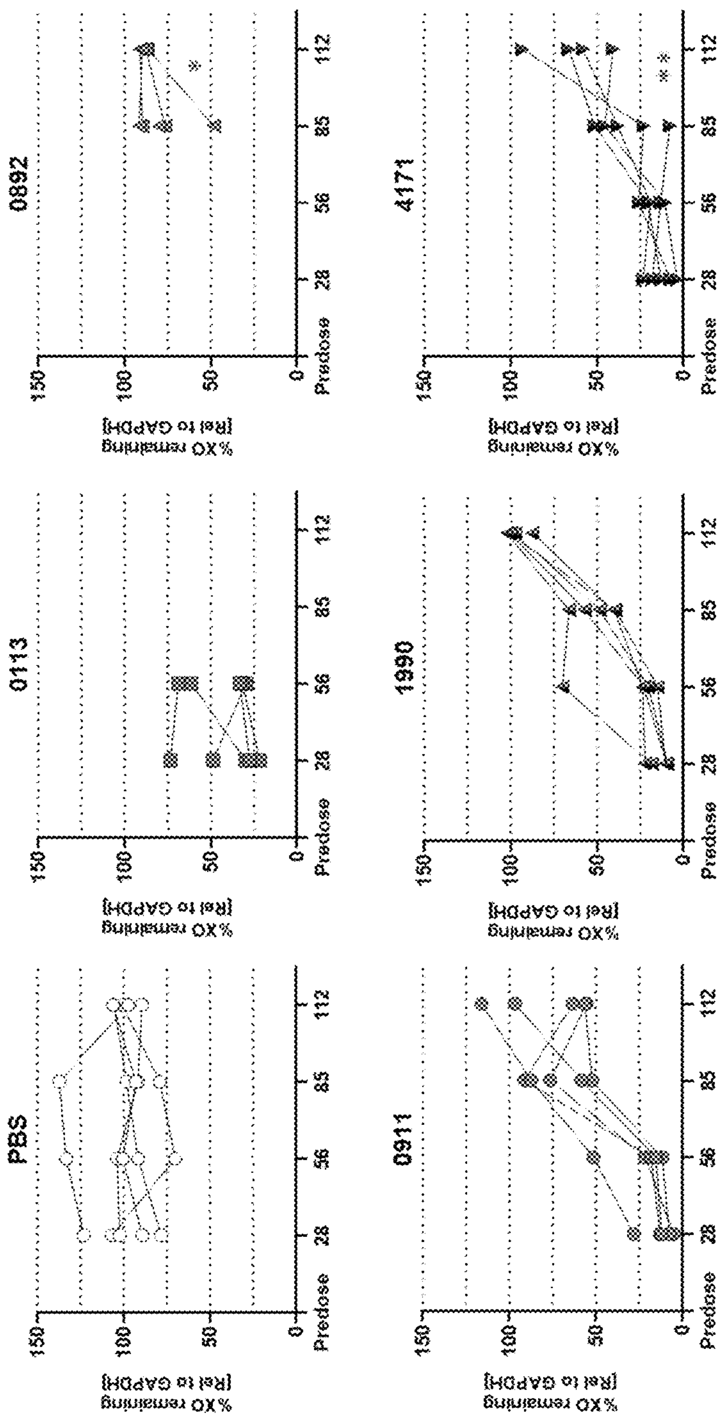

*Macaca fascicularis* NHPs (n=5 per group) of mixed weight (3-8 kg) and mixed sex (male, female) were subcutaneously administered a dual C22/GalNAc-conjugated XDH RNAi oligonucleotide as set forth in Table 2 at a single dose of 6 mg/kg formulated in PBS. A control group of NHPs (n=5) were administered only PBS. Serum and liver samples from non-terminal biopsies were collected at days 0 (pre-dose), 28, 56, 84, and 112 as illustrated in FIG. 4. Total RNA derived from liver samples was subjected to qRT-PCR analysis to determine XDH mRNA levels. The values were normalized to XDH mRNA of pre-dosed samples (day 0). At day 28, all treatment groups, with the exception of XDH-4176, displayed a significant reduction of XDH mRNA levels in non-human primate liver samples. The XDH-4171-treated group exhibited the highest level of XDH silencing (FIG. 5A). Similarly, the dual C22/GalNAc conjugated XDH RNAi oligonucleotides, from the top 4 best-performing groups with respect to mRNA silencing, reduced expression of XO in the liver at Day 28 (FIG. 5B). Protein and mRNA levels were also evaluated at Day 112 (FIGS. 6A and 6B, respectively). These data show XDH-4171 maintained silencing of XDH mRNA and XO protein in the liver of NHPs through Day 112, demonstrating the ability of XDH-4171 to sustain silencing in mammals.

| SEQUENCE LISTING | | | |
|---|---|---|---|
| Construct | Description | Sequence | SEQ ID NO |
| XDH-0113 | 36 mer Unmodified Sense strand | AAAUUGGUUUUCUUUGUGAAGCAGCCGAAAGG CUGC | 1 |
| XDH-0113 | 22 mer Unmodified | UUCACAAAGAAAACCAAUUUGG | 2 |

-continued

SEQUENCE LISTING

| Construct | Description | Sequence | SEQ ID NO |
|---|---|---|---|
| | Antisense strand | | |
| XDH-0113 | 36 mer Modified Sense strand | [ademAs-C22][mA][mA][mU][mU][mG][mG][fU][fU][fU][fU][mC][mU][mU][mU][mG][mU][mG][mA][mA][mG][mC][mA][mG][mC][mC][mG][ademA-GalNAc][ademA-GalNAc][ademA-GalNAc][mG][mG][mC][mU][mG][mC] | 3 |
| XDH-0113 | 22 mer Modified Antisense strand | [MePhosphonate-4O-mUs][fUs][fCs][fA][fC][mA][fA][mA][mG][fA][mA][mA][mA][fC][mC][mA][mA][mU][mU][mUs][mGs][mG] | 4 |
| XDH-0892 | 36 mer Unmodified Sense strand | UGGCAUUGAGAUGAAGUUCAGCAGCCGAAAGGCUGC | 5 |
| XDH-0892 | 22 mer Unmodified Antisense strand | UGAACUUCAUCUCAAUGCCAGG | 6 |
| XDH-0892 | 36 mer Modified Sense strand | [ademUs-C22][mG][mG][mC][mA][mU][mU][fG][fA][fG][fA][mU][mG][mA][mA][mG][mU][mU][mC][mA][mG][mC][mA][mG][mC][mC][mG][ademA-GalNAc][ademA-GalNAc][ademA-GalNAc][mG][mG][mC][mU][mG][mC] | 7 |
| XDH-0892 | 22 mer Modified Antisense strand | [MePhosphonate-4O-mUs][fGs][fAs][fA][fC][mU][fU][mC][mA][fU][mC][mU][mC][fA][mA][mU][mG][mC][mC][mAs][mGs][mG] | 8 |
| XDH-0898 | 36 mer Unmodified Sense strand | UGAGAUGAAGUUCAAGAAUAGCAGCCGAAAGGCUGC | 9 |
| XDH-0898 | 22 mer Unmodified Antisense strand | UAUUCUUGAACUUCAUCUCAGG | 10 |
| XDH-0898 | 36 mer Modified Sense strand | [ademUs-C22][mG][mA][mG][mA][mU][mG][fA][fA][fG][fU][mU][mC][mA][mA][mG][mA][mA][mU][mA][mG][mC][mA][mG][mC][mC][mG][ademA-GalNAc][ademA-GalNAc][ademA-GalNAc][mG][mG][mC][mU][mG][mC] | 11 |
| XDH-0898 | 22 mer Modified Antisense strand | [MePhosphonate-4O-mUs][fAs][fUs][fU][fC][mU][fU][mG][mA][fA][mC][mU][mU][fC][mA][mU][mC][mU][mC][mAs][mGs][mG] | 12 |
| XDH-0911 | 36 mer Unmodified Sense strand | AAGAAUAUGCUGUUUCCUAAGCAGCCGAAAGGCUGC | 13 |
| XDH-0911 | 22 mer Unmodified Antisense strand | UUAGGAAACAGCAUAUUCUUGG | 14 |
| XDH-0911 | 36 mer Modified Sense strand | [ademAs-C22][mA][mG][mA][mA][mU][mA][fU][fG][fC][fU][mG][mU][mU][mU][mC][mC][mU][mA][mA][mG][mC][mA][mG][mC][mC][mG][ademA-GalNAc][ademA-GalNAc][ademA-GalNAc][mG][mG][mC][mU][mG][mC] | 15 |
| XDH-0911 | 22 mer Modified Antisense strand | [MePhosphonate-4O-mUs][fUs][fAs][fG][fG][mA][fA][mA][mC][fA][mG][mC][mA][fU][mA][mU][mU][mC][mU][mUs][mGs][mG] | 16 |

-continued

| SEQUENCE LISTING | | | |
|---|---|---|---|
| Construct | Description | Sequence | SEQ ID NO |
| XDH-1990 | 36 mer Unmodified Sense strand | AGGGUUUGUUUGUUUCAUUAGCAGCCGAAAGG CUGC | 17 |
| XDH-1990 | 22 mer Unmodified Antisense strand | UAAUGAAACAAACAAACCCUGG | 18 |
| XDH-1990 | 36 mer Modified Sense strand | [ademAs-C22][mG][mG][mG][mU][mU][mU][fG] [fU][fU][fU][mG][mU][mU][mU][mC][mA][mU][mU] [mA][mG][mC][mA][mG][mC][mC][mG][ademA-GalNAc][ademA-GalNAc][ademA-GalNAc][mG][mG][mC] [mU][mG][mC] | 19 |
| XDH-1990 | 22 mer Modified Antisense strand | [MePhosphonate-4O-mUs][fAs][fAs][fU][fG][mA][fA] [mA][mC][fA][mA][mA][mC][fA][mA][mA][mC][mC] [mC][mUs][mGs][mG] | 20 |
| XDH-4171 | 36 mer Unmodified Sense strand | CAGAACAUGGAUCUAUUAAAGCAGCCGAAAGGC UGC | 21 |
| XDH-4171 | 22 mer Unmodified Antisense strand | UUUAAUAGAUCCAUGUUCUGGG | 22 |
| XDH-4171 | 36 mer Modified Sense strand | [ademCs-C22][mA][mG][mA][mA][mC][mA][fU][fG] [fG][fA][mU][mC][mU][mA][mU][mU][mA][mA][mA] [mG][mC][mA][mG][mC][mC][mG][ademA-GalNAc] [ademA-GalNAc][ademA-GalNAc][mG][mG][mC] [mU][mG][mC] | 23 |
| XDH-4171 | 22 mer Modified Antisense strand | [MePhosphonate-4O-mUs][fUs][fUs][fA][fA][mU][fA] [mG][mA][fU][mC][mC][mA][fU][mG][mU][mU][mC] [mU][mGs][mGs][mG] | 24 |
| XDH-4176 | 36 mer Unmodified Sense strand | CAUGGAUCUAUUAAAGUCAAGCAGCCGAAAGGC UGC | 25 |
| XDH-4176 | 22 mer Unmodified Antisense strand | UUGACUUUAAUAGAUCCAUGGG | 26 |
| XDH-4176 | 36 mer Modified Sense strand | [ademCs-C22][mA][mU][mG][mG][mA][mU][fC][fU] [fA][fU][mU][mA][mA][mA][mG][mU][mC][mA][mA] [mG][mC][mA][mG][mC][mC][mG][ademA-GalNAc] [ademA-GalNAc][ademA-GalNAc][mG][mG][mC] [mU][mG][mC] | 27 |
| XDH-4176 | 22 mer Modified Antisense strand | [MePhosphonate-4O-mUs][fUs][fGs][fA][fC][mU][fU] [mU][mA][fA][mU][mA][mG][fA][mU][mC][mC][mA] [mU][mGs][mGs][mG] | 28 |
| Stem loop | 16 mer Unmodified Sense strand | GCAGCCGAAAGGCUGC | 29 |
| XDH-A | 36 mer Modified Sense strand | [mAs][mG][mA][mU][mA][mG][mG][fC][fA][fU][fU] [mG][mA][mA][mA][mU][mG][mA][mA][mA][mG][mC] [mA][mG][mC][mC][mG][ademAs-C22][mA][mA][mG][mG][mC][mU][mG][mC] | 30 |
| XDH-A | 22 mer Modified | [MePhosphonate-4O-mUs][fUs][fUs][fC][fA][mU][fU][mU][mC][fA][mA] | 31 |

-continued

SEQUENCE LISTING

| Construct | Description | Sequence | SEQ ID NO |
|---|---|---|---|
| | Antisense strand | [mU][mG][fC][mC][mU][mA][mU][mC][mUs][mGs][mG] | |
| XDH-B | 36 mer Modified Sense strand | mG][mA][mA][mA][mU][mG][mA][mA][mA][mG][mC][mA][mG][mC][mC][mG][ademA-GalNAc][ademA-GalNAc][ademA-GalNAc][mG][mG][mC][mU][mG][mC] | 32 |
| XDH-B | 22 mer Modified Antisense strand | [MePhosphonate-4O-mUs][fUs][fU][fC][fA][mU][fU][mU][mC][fA][mA][mU][mG][fC][mC][mU][mA][mU][mC][mUs][mGs][mG] | 33 |
| XDH-C | 36 mer Modified Sense strand | [ademAs-C22][mG][mA][mU][mA][mG][mG][fC][fA][fU][fU][mG][mA][mA][mA][mU][mG][mA][mA][mA][mG][mC][mA][mG][mC][mC][mG][ademA-GalNAc][ademA-GalNAc][ademA-GalNAc][mG][mG][mC][mU][mG][mC] | 34 |
| XDH-C | 22 mer Modified Antisense strand | [MePhosphonate-4O-mUs][fUs][fUs][fC][fA][mU][fU][mU][mC][fA][mA][mU][mG][fC][mC][mU][mA][mU][mC][mUs][mGs][mG] | 35 |

The invention claimed is:

1. An siRNA comprising a first RNA oligonucleotide and a second RNA oligonucleotide, wherein the first RNA oligonucleotide consists of the sequence set forth in SEQ ID: 23, and the second RNA oligonucleotide consists of the sequence set forth in SEQ ID: 24.

2. A pharmaceutical composition comprising the siRNA according to claim 1 and a pharmaceutically acceptable carrier, delivery agent or excipient.

3. A method of treating gout in a subject in need thereof, the method comprising administering to the subject the siRNA of claim 1.

4. A method for reducing xanthine dehydrogenase (XDH) expression in a subject in need thereof, the method comprising administering to the subject the siRNA of claim 1.

5. A method for reducing XDH expression in a cell, the method comprising contacting the cell with the siRNA of claim 1.

* * * * *

SEQUENCE LISTING

```
Sequence total quantity: 35
SEQ ID NO: 1            moltype = RNA  length = 36
FEATURE                 Location/Qualifiers
source                  1..36
                        mol_type = other RNA
                        organism = synthetic construct
SEQUENCE: 1
aaattggttt tctttgtgaa gcagccgaaa ggctgc                        36

SEQ ID NO: 2            moltype = RNA  length = 22
FEATURE                 Location/Qualifiers
source                  1..22
                        mol_type = other RNA
                        organism = synthetic construct
SEQUENCE: 2
ttcacaaaga aaaccaattt gg                                       22

SEQ ID NO: 3            moltype = RNA  length = 36
FEATURE                 Location/Qualifiers
modified_base           1
                        mod_base = OTHER
                        note = C22 hydrocarbon chain, phosphorothioate linkage
modified_base           2
                        mod_base = OTHER
                        note = 2'-O-methyl modified nucleotide
modified_base           3
                        mod_base = OTHER
                        note = 2'-O-methyl modified nucleotide
modified_base           4
                        mod_base = OTHER
                        note = 2'-O-methyl modified nucleotide
modified_base           5
                        mod_base = OTHER
                        note = 2'-O-methyl modified nucleotide
modified_base           6
                        mod_base = OTHER
                        note = 2'-O-methyl modified nucleotide
modified_base           7
                        mod_base = OTHER
                        note = 2'-O-methyl modified nucleotide
modified_base           8
                        mod_base = OTHER
```

-continued

```
                     note = 2'-fluoro modified nucleotide with a
                      phosphorothioate linkage
modified_base        9
                     mod_base = OTHER
                     note = 2'-fluoro modified nucleotide
modified_base        10
                     mod_base = OTHER
                     note = 2'-fluoro modified nucleotide
modified_base        11
                     mod_base = OTHER
                     note = 2'-fluoro modified nucleotide
modified_base        12
                     mod_base = OTHER
                     note = 2'-O-methyl modified nucleotide
modified_base        13
                     mod_base = OTHER
                     note = 2'-O-methyl modified nucleotide
modified_base        14
                     mod_base = OTHER
                     note = 2'-O-methyl modified nucleotide
modified_base        15
                     mod_base = OTHER
                     note = 2'-O-methyl modified nucleotide
modified_base        16
                     mod_base = OTHER
                     note = 2'-O-methyl modified nucleotide
modified_base        17
                     mod_base = OTHER
                     note = 2'-O-methyl modified nucleotide
modified_base        18
                     mod_base = OTHER
                     note = 2'-O-methyl modified nucleotide
modified_base        19
                     mod_base = OTHER
                     note = 2'-O-methyl modified nucleotide
modified_base        20
                     mod_base = OTHER
                     note = 2'-O-methyl modified nucleotide
modified_base        21
                     mod_base = OTHER
                     note = 2'-O-methyl modified nucleotide
modified_base        22
                     mod_base = OTHER
                     note = 2'-O-methyl modified nucleotide
modified_base        23
                     mod_base = OTHER
                     note = 2'-O-methyl modified nucleotide
modified_base        24
                     mod_base = OTHER
                     note = 2'-O-methyl modified nucleotide
modified_base        25
                     mod_base = OTHER
                     note = 2'-O-methyl modified nucleotide
modified_base        26
                     mod_base = OTHER
                     note = 2'-O-methyl modified nucleotide
modified_base        27
                     mod_base = OTHER
                     note = 2'-O-methyl modified nucleotide
modified_base        28
                     mod_base = OTHER
                     note = GalNAc (N-acetylgalactosamine) modification attached
                      to an adenine nucleotide
modified_base        29
                     mod_base = OTHER
                     note = GalNAc (N-acetylgalactosamine) modification attached
                      to an adenine nucleotide
modified_base        30
                     mod_base = OTHER
                     note = GalNAc (N-acetylgalactosamine) modification attached
                      to an adenine nucleotide
modified_base        31
                     mod_base = OTHER
                     note = 2'-O-methyl modified nucleotide
modified_base        32
                     mod_base = OTHER
                     note = 2'-O-methyl modified nucleotide
modified_base        33
                     mod_base = OTHER
```

-continued

```
                         note = 2'-O-methyl modified nucleotide
modified_base            34
                         mod_base = OTHER
                         note = 2'-O-methyl modified nucleotide
modified_base            35
                         mod_base = OTHER
                         note = 2'-O-methyl modified nucleotide
modified_base            36
                         mod_base = OTHER
                         note = 2'-O-methyl modified nucleotide
source                   1..36
                         mol_type = other RNA
                         organism = synthetic construct
SEQUENCE: 3
aaattggttt tctttgtgaa gcagccgaaa ggctgc                              36

SEQ ID NO: 4             moltype = RNA  length = 22
FEATURE                  Location/Qualifiers
modified_base            1
                         mod_base = OTHER
                         note = 4'-O-monomethylphosphonate-2'-O-methyl modified
                          nucleotide
modified_base            2
                         mod_base = OTHER
                         note = 2'-fluoro modified nucleotide with a
                          phosphorothioate linkage
modified_base            3
                         mod_base = OTHER
                         note = 2'-fluoro modified nucleotide with a
                          phosphorothioate linkage
modified_base            4
                         mod_base = OTHER
                         note = 2'-fluoro modified nucleotide
modified_base            5
                         mod_base = OTHER
                         note = 2'-fluoro modified nucleotide
modified_base            6
                         mod_base = OTHER
                         note = 2'-O-methyl modified nucleotide
modified_base            7
                         mod_base = OTHER
                         note = 2'-fluoro modified nucleotide
modified_base            8
                         mod_base = OTHER
                         note = 2'-O-methyl modified nucleotide
modified_base            9
                         mod_base = OTHER
                         note = 2'-O-methyl modified nucleotide
modified_base            10
                         mod_base = OTHER
                         note = 2'-fluoro modified nucleotide
modified_base            11
                         mod_base = OTHER
                         note = 2'-O-methyl modified nucleotide
modified_base            12
                         mod_base = OTHER
                         note = 2'-O-methyl modified nucleotide
modified_base            13
                         mod_base = OTHER
                         note = 2'-O-methyl modified nucleotide
modified_base            14
                         mod_base = OTHER
                         note = 2'-fluoro modified nucleotide
modified_base            15
                         mod_base = OTHER
                         note = 2'-O-methyl modified nucleotide
modified_base            16
                         mod_base = OTHER
                         note = 2'-O-methyl modified nucleotide
modified_base            17
                         mod_base = OTHER
                         note = 2'-O-methyl modified nucleotide
modified_base            18
                         mod_base = OTHER
                         note = 2'-O-methyl modified nucleotide
modified_base            19
                         mod_base = OTHER
                         note = 2'-O-methyl modified nucleotide
modified_base            20
```

-continued

```
                         mod_base = OTHER
                         note = 2'-O-methyl modified nucleotide, phosphorothioate
                          linkage
modified_base            21
                         mod_base = OTHER
                         note = 2'-O-methyl modified nucleotide, phosphorothioate
                          linkage
modified_base            22
                         mod_base = OTHER
                         note = 2'-O-methyl modified nucleotide
source                   1..22
                         mol_type = other RNA
                         organism = synthetic construct
SEQUENCE: 4
ttcacaaaga aaaccaattt gg                                          22

SEQ ID NO: 5             moltype = RNA  length = 36
FEATURE                  Location/Qualifiers
source                   1..36
                         mol_type = other RNA
                         organism = synthetic construct
SEQUENCE: 5
tggcattgag atgaagttca gcagccgaaa ggctgc                           36

SEQ ID NO: 6             moltype = RNA  length = 22
FEATURE                  Location/Qualifiers
source                   1..22
                         mol_type = other RNA
                         organism = synthetic construct
SEQUENCE: 6
tgaacttcat ctcaatgcca gg                                          22

SEQ ID NO: 7             moltype = RNA  length = 36
FEATURE                  Location/Qualifiers
modified_base            1
                         mod_base = OTHER
                         note = C22 hydrocarbon chain, phosphorothioate linkage
modified_base            2
                         mod_base = OTHER
                         note = 2'-O-methyl modified nucleotide
modified_base            3
                         mod_base = OTHER
                         note = 2'-O-methyl modified nucleotide
modified_base            4
                         mod_base = OTHER
                         note = 2'-O-methyl modified nucleotide
modified_base            5
                         mod_base = OTHER
                         note = 2'-O-methyl modified nucleotide
modified_base            6
                         mod_base = OTHER
                         note = 2'-O-methyl modified nucleotide
modified_base            7
                         mod_base = OTHER
                         note = 2'-O-methyl modified nucleotide
modified_base            8
                         mod_base = OTHER
                         note = 2'-fluoro modified nucleotide
modified_base            9
                         mod_base = OTHER
                         note = 2'-fluoro modified nucleotide
modified_base            10
                         mod_base = OTHER
                         note = 2'-fluoro modified nucleotide
modified_base            11
                         mod_base = OTHER
                         note = 2'-fluoro modified nucleotide
modified_base            12
                         mod_base = OTHER
                         note = 2'-O-methyl modified nucleotide
modified_base            13
                         mod_base = OTHER
                         note = 2'-O-methyl modified nucleotide
modified_base            14
                         mod_base = OTHER
                         note = 2'-O-methyl modified nucleotide
modified_base            15
                         mod_base = OTHER
                         note = 2'-O-methyl modified nucleotide
```

```
modified_base          16
                       mod_base = OTHER
                       note = 2'-O-methyl modified nucleotide
modified_base          17
                       mod_base = OTHER
                       note = 2'-O-methyl modified nucleotide
modified_base          18
                       mod_base = OTHER
                       note = 2'-O-methyl modified nucleotide
modified_base          19
                       mod_base = OTHER
                       note = 2'-O-methyl modified nucleotide
modified_base          20
                       mod_base = OTHER
                       note = 2'-O-methyl modified nucleotide
modified_base          21
                       mod_base = OTHER
                       note = 2'-O-methyl modified nucleotide
modified_base          22
                       mod_base = OTHER
                       note = 2'-O-methyl modified nucleotide
modified_base          23
                       mod_base = OTHER
                       note = 2'-O-methyl modified nucleotide
modified_base          24
                       mod_base = OTHER
                       note = 2'-O-methyl modified nucleotide
modified_base          25
                       mod_base = OTHER
                       note = 2'-O-methyl modified nucleotide
modified_base          26
                       mod_base = OTHER
                       note = 2'-O-methyl modified nucleotide
modified_base          27
                       mod_base = OTHER
                       note = 2'-O-methyl modified nucleotide
modified_base          28
                       mod_base = OTHER
                       note = GalNAc (N-acetylgalactosamine) modification attached
                        to an adenine nucleotide
modified_base          29
                       mod_base = OTHER
                       note = GalNAc (N-acetylgalactosamine) modification attached
                        to an adenine nucleotide
modified_base          30
                       mod_base = OTHER
                       note = GalNAc (N-acetylgalactosamine) modification attached
                        to an adenine nucleotide
modified_base          31
                       mod_base = OTHER
                       note = 2'-O-methyl modified nucleotide
modified_base          32
                       mod_base = OTHER
                       note = 2'-O-methyl modified nucleotide
modified_base          33
                       mod_base = OTHER
                       note = 2'-O-methyl modified nucleotide
modified_base          34
                       mod_base = OTHER
                       note = 2'-O-methyl modified nucleotide
modified_base          35
                       mod_base = OTHER
                       note = 2'-O-methyl modified nucleotide
modified_base          36
                       mod_base = OTHER
                       note = 2'-O-methyl modified nucleotide
source                 1..36
                       mol_type = other RNA
                       organism = synthetic construct
SEQUENCE: 7
tggcattgag atgaagttca gcagccgaaa ggctgc                          36

SEQ ID NO: 8           moltype = RNA  length = 22
FEATURE                Location/Qualifiers
modified_base          1
                       mod_base = OTHER
                       note = 4'-O-monomethylphosphonate-2'-O-methyl modified
                        nucleotide
modified_base          2
```

-continued

```
                         mod_base = OTHER
                         note = 2'-fluoro modified nucleotide with a
                          phosphorothioate linkage
modified_base            3
                         mod_base = OTHER
                         note = 2'-fluoro modified nucleotide with a
                          phosphorothioate linkage
modified_base            4
                         mod_base = OTHER
                         note = 2'-fluoro modified nucleotide
modified_base            5
                         mod_base = OTHER
                         note = 2'-fluoro modified nucleotide
modified_base            6
                         mod_base = OTHER
                         note = 2'-O-methyl modified nucleotide
modified_base            7
                         mod_base = OTHER
                         note = 2'-fluoro modified nucleotide
modified_base            8
                         mod_base = OTHER
                         note = 2'-O-methyl modified nucleotide
modified_base            9
                         mod_base = OTHER
                         note = 2'-O-methyl modified nucleotide
modified_base            10
                         mod_base = OTHER
                         note = 2'-fluoro modified nucleotide
modified_base            11
                         mod_base = OTHER
                         note = 2'-O-methyl modified nucleotide
modified_base            12
                         mod_base = OTHER
                         note = 2'-O-methyl modified nucleotide
modified_base            13
                         mod_base = OTHER
                         note = 2'-O-methyl modified nucleotide
modified_base            14
                         mod_base = OTHER
                         note = 2'-fluoro modified nucleotide
modified_base            15
                         mod_base = OTHER
                         note = 2'-O-methyl modified nucleotide
modified_base            16
                         mod_base = OTHER
                         note = 2'-O-methyl modified nucleotide
modified_base            17
                         mod_base = OTHER
                         note = 2'-O-methyl modified nucleotide
modified_base            18
                         mod_base = OTHER
                         note = 2'-O-methyl modified nucleotide
modified_base            19
                         mod_base = OTHER
                         note = 2'-O-methyl modified nucleotide
modified_base            20
                         mod_base = OTHER
                         note = 2'-O-methyl modified nucleotide, phosphorothioate
                          linkage
modified_base            21
                         mod_base = OTHER
                         note = 2'-O-methyl modified nucleotide, phosphorothioate
                          linkage
modified_base            22
                         mod_base = OTHER
                         note = 2'-O-methyl modified nucleotide
source                   1..22
                         mol_type = other RNA
                         organism = synthetic construct
SEQUENCE: 8
tgaacttcat ctcaatgcca gg                                          22

SEQ ID NO: 9             moltype = RNA  length = 36
FEATURE                  Location/Qualifiers
source                   1..36
                         mol_type = other RNA
                         organism = synthetic construct
SEQUENCE: 9
tgagatgaag ttcaagaata gcagccgaaa ggctgc                           36
```

-continued

```
SEQ ID NO: 10           moltype = RNA  length = 22
FEATURE                 Location/Qualifiers
source                  1..22
                        mol_type = other RNA
                        organism = synthetic construct
SEQUENCE: 10
tattcttgaa cttcatctca gg                                          22

SEQ ID NO: 11           moltype = RNA  length = 36
FEATURE                 Location/Qualifiers
modified_base           1
                        mod_base = OTHER
                        note = C22 hydrocarbon chain, phosphorothioate linkage
modified_base           2
                        mod_base = OTHER
                        note = 2'-O-methyl modified nucleotide
modified_base           3
                        mod_base = OTHER
                        note = 2'-O-methyl modified nucleotide
modified_base           4
                        mod_base = OTHER
                        note = 2'-O-methyl modified nucleotide
modified_base           5
                        mod_base = OTHER
                        note = 2'-O-methyl modified nucleotide
modified_base           6
                        mod_base = OTHER
                        note = 2'-O-methyl modified nucleotide
modified_base           7
                        mod_base = OTHER
                        note = 2'-O-methyl modified nucleotide
modified_base           8
                        mod_base = OTHER
                        note = 2'-fluoro modified nucleotide
modified_base           9
                        mod_base = OTHER
                        note = 2'-fluoro modified nucleotide
modified_base           10
                        mod_base = OTHER
                        note = 2'-fluoro modified nucleotide
modified_base           11
                        mod_base = OTHER
                        note = 2'-fluoro modified nucleotide
modified_base           12
                        mod_base = OTHER
                        note = 2'-O-methyl modified nucleotide
modified_base           13
                        mod_base = OTHER
                        note = 2'-O-methyl modified nucleotide
modified_base           14
                        mod_base = OTHER
                        note = 2'-O-methyl modified nucleotide
modified_base           15
                        mod_base = OTHER
                        note = 2'-O-methyl modified nucleotide
modified_base           16
                        mod_base = OTHER
                        note = 2'-O-methyl modified nucleotide
modified_base           17
                        mod_base = OTHER
                        note = 2'-O-methyl modified nucleotide
modified_base           18
                        mod_base = OTHER
                        note = 2'-O-methyl modified nucleotide
modified_base           19
                        mod_base = OTHER
                        note = 2'-O-methyl modified nucleotide
modified_base           20
                        mod_base = OTHER
                        note = 2'-O-methyl modified nucleotide
modified_base           21
                        mod_base = OTHER
                        note = 2'-O-methyl modified nucleotide
modified_base           22
                        mod_base = OTHER
                        note = 2'-O-methyl modified nucleotide
modified_base           23
                        mod_base = OTHER
```

-continued

```
                         note = 2'-O-methyl modified nucleotide
modified_base            24
                         mod_base = OTHER
                         note = 2'-O-methyl modified nucleotide
modified_base            25
                         mod_base = OTHER
                         note = 2'-O-methyl modified nucleotide
modified_base            26
                         mod_base = OTHER
                         note = 2'-O-methyl modified nucleotide
modified_base            27
                         mod_base = OTHER
                         note = 2'-O-methyl modified nucleotide
modified_base            28
                         mod_base = OTHER
                         note = GalNAc (N-acetylgalactosamine) modification attached
                          to an adenine nucleotide
modified_base            29
                         mod_base = OTHER
                         note = GalNAc (N-acetylgalactosamine) modification attached
                          to an adenine nucleotide
modified_base            30
                         mod_base = OTHER
                         note = GalNAc (N-acetylgalactosamine) modification attached
                          to an adenine nucleotide
modified_base            31
                         mod_base = OTHER
                         note = 2'-O-methyl modified nucleotide
modified_base            32
                         mod_base = OTHER
                         note = 2'-O-methyl modified nucleotide
modified_base            33
                         mod_base = OTHER
                         note = 2'-O-methyl modified nucleotide
modified_base            34
                         mod_base = OTHER
                         note = 2'-O-methyl modified nucleotide
modified_base            35
                         mod_base = OTHER
                         note = 2'-O-methyl modified nucleotide
modified_base            36
                         mod_base = OTHER
                         note = 2'-O-methyl modified nucleotide
source                   1..36
                         mol_type = other RNA
                         organism = synthetic construct
SEQUENCE: 11
tgagatgaag ttcaagaata gcagccgaaa ggctgc                             36

SEQ ID NO: 12            moltype = RNA  length = 22
FEATURE                  Location/Qualifiers
modified_base            1
                         mod_base = OTHER
                         note = 4'-O-monomethylphosphonate-2'-O-methyl modified
                          nucleotide
modified_base            2
                         mod_base = OTHER
                         note = 2'-fluoro modified nucleotide with a
                          phosphorothioate linkage
modified_base            3
                         mod_base = OTHER
                         note = 2'-fluoro modified nucleotide with a
                          phosphorothioate linkage
modified_base            4
                         mod_base = OTHER
                         note = 2'-fluoro modified nucleotide
modified_base            5
                         mod_base = OTHER
                         note = 2'-fluoro modified nucleotide
modified_base            6
                         mod_base = OTHER
                         note = 2'-O-methyl modified nucleotide
modified_base            7
                         mod_base = OTHER
                         note = 2'-fluoro modified nucleotide
modified_base            8
                         mod_base = OTHER
                         note = 2'-O-methyl modified nucleotide
modified_base            9
```

-continued

```
                         mod_base = OTHER
                         note = 2'-O-methyl modified nucleotide
modified_base            10
                         mod_base = OTHER
                         note = 2'-fluoro modified nucleotide
modified_base            11
                         mod_base = OTHER
                         note = 2'-O-methyl modified nucleotide
modified_base            12
                         mod_base = OTHER
                         note = 2'-O-methyl modified nucleotide
modified_base            13
                         mod_base = OTHER
                         note = 2'-O-methyl modified nucleotide
modified_base            14
                         mod_base = OTHER
                         note = 2'-fluoro modified nucleotide
modified_base            15
                         mod_base = OTHER
                         note = 2'-O-methyl modified nucleotide
modified_base            16
                         mod_base = OTHER
                         note = 2'-O-methyl modified nucleotide
modified_base            17
                         mod_base = OTHER
                         note = 2'-O-methyl modified nucleotide
modified_base            18
                         mod_base = OTHER
                         note = 2'-O-methyl modified nucleotide
modified_base            19
                         mod_base = OTHER
                         note = 2'-O-methyl modified nucleotide
modified_base            20
                         mod_base = OTHER
                         note = 2'-O-methyl modified nucleotide, phosphorothioate
                          linkage
modified_base            21
                         mod_base = OTHER
                         note = 2'-O-methyl modified nucleotide, phosphorothioate
                          linkage
modified_base            22
                         mod_base = OTHER
                         note = 2'-O-methyl modified nucleotide
source                   1..22
                         mol_type = other RNA
                         organism = synthetic construct
SEQUENCE: 12
tattcttgaa cttcatctca gg                                            22

SEQ ID NO: 13            moltype = RNA  length = 36
FEATURE                  Location/Qualifiers
source                   1..36
                         mol_type = other RNA
                         organism = synthetic construct
SEQUENCE: 13
aagaatatgc tgtttcctaa gcagccgaaa ggctgc                             36

SEQ ID NO: 14            moltype = RNA  length = 22
FEATURE                  Location/Qualifiers
source                   1..22
                         mol_type = other RNA
                         organism = synthetic construct
SEQUENCE: 14
ttaggaaaca gcatattctt gg                                            22

SEQ ID NO: 15            moltype = RNA  length = 36
FEATURE                  Location/Qualifiers
modified_base            1
                         mod_base = OTHER
                         note = C22 hydrocarbon chain, phosphorothioate linkage
modified_base            2
                         mod_base = OTHER
                         note = 2'-O-methyl modified nucleotide
modified_base            3
                         mod_base = OTHER
                         note = 2'-O-methyl modified nucleotide
modified_base            4
                         mod_base = OTHER
                         note = 2'-O-methyl modified nucleotide
```

-continued

```
modified_base          5
                       mod_base = OTHER
                       note = 2'-O-methyl modified nucleotide
modified_base          6
                       mod_base = OTHER
                       note = 2'-O-methyl modified nucleotide
modified_base          7
                       mod_base = OTHER
                       note = 2'-O-methyl modified nucleotide
modified_base          8
                       mod_base = OTHER
                       note = 2'-fluoro modified nucleotide
modified_base          9
                       mod_base = OTHER
                       note = 2'-fluoro modified nucleotide
modified_base          10
                       mod_base = OTHER
                       note = 2'-fluoro modified nucleotide
modified_base          11
                       mod_base = OTHER
                       note = 2'-fluoro modified nucleotide
modified_base          12
                       mod_base = OTHER
                       note = 2'-O-methyl modified nucleotide
modified_base          13
                       mod_base = OTHER
                       note = 2'-O-methyl modified nucleotide
modified_base          14
                       mod_base = OTHER
                       note = 2'-O-methyl modified nucleotide
modified_base          15
                       mod_base = OTHER
                       note = 2'-O-methyl modified nucleotide
modified_base          16
                       mod_base = OTHER
                       note = 2'-O-methyl modified nucleotide
modified_base          17
                       mod_base = OTHER
                       note = 2'-O-methyl modified nucleotide
modified_base          18
                       mod_base = OTHER
                       note = 2'-O-methyl modified nucleotide
modified_base          19
                       mod_base = OTHER
                       note = 2'-O-methyl modified nucleotide
modified_base          20
                       mod_base = OTHER
                       note = 2'-O-methyl modified nucleotide
modified_base          21
                       mod_base = OTHER
                       note = 2'-O-methyl modified nucleotide
modified_base          22
                       mod_base = OTHER
                       note = 2'-O-methyl modified nucleotide
modified_base          23
                       mod_base = OTHER
                       note = 2'-O-methyl modified nucleotide
modified_base          24
                       mod_base = OTHER
                       note = 2'-O-methyl modified nucleotide
modified_base          25
                       mod_base = OTHER
                       note = 2'-O-methyl modified nucleotide
modified_base          26
                       mod_base = OTHER
                       note = 2'-O-methyl modified nucleotide
modified_base          27
                       mod_base = OTHER
                       note = 2'-O-methyl modified nucleotide
modified_base          28
                       mod_base = OTHER
                       note = GalNAc (N-acetylgalactosamine) modification attached
                        to an adenine nucleotide
modified_base          29
                       mod_base = OTHER
                       note = GalNAc (N-acetylgalactosamine) modification attached
                        to an adenine nucleotide
modified_base          30
                       mod_base = OTHER
```

```
                        note = GalNAc (N-acetylgalactosamine) modification attached
                         to an adenine nucleotide
modified_base           31
                        mod_base = OTHER
                        note = 2'-O-methyl modified nucleotide
modified_base           32
                        mod_base = OTHER
                        note = 2'-O-methyl modified nucleotide
modified_base           33
                        mod_base = OTHER
                        note = 2'-O-methyl modified nucleotide
modified_base           34
                        mod_base = OTHER
                        note = 2'-O-methyl modified nucleotide
modified_base           35
                        mod_base = OTHER
                        note = 2'-O-methyl modified nucleotide
modified_base           36
                        mod_base = OTHER
                        note = 2'-O-methyl modified nucleotide
source                  1..36
                        mol_type = other RNA
                        organism = synthetic construct
SEQUENCE: 15
aagaatatgc tgtttcctaa gcagccgaaa ggctgc                            36

SEQ ID NO: 16           moltype = RNA  length = 22
FEATURE                 Location/Qualifiers
modified_base           1
                        mod_base = OTHER
                        note = 4'-O-monomethylphosphonate-2'-O-methyl modified
                         nucleotide
modified_base           2
                        mod_base = OTHER
                        note = 2'-fluoro modified nucleotide with a
                         phosphorothioate linkage
modified_base           3
                        mod_base = OTHER
                        note = 2'-fluoro modified nucleotide with a
                         phosphorothioate linkage
modified_base           4
                        mod_base = OTHER
                        note = 2'-fluoro modified nucleotide
modified_base           5
                        mod_base = OTHER
                        note = 2'-fluoro modified nucleotide
modified_base           6
                        mod_base = OTHER
                        note = 2'-O-methyl modified nucleotide
modified_base           7
                        mod_base = OTHER
                        note = 2'-fluoro modified nucleotide
modified_base           8
                        mod_base = OTHER
                        note = 2'-O-methyl modified nucleotide
modified_base           9
                        mod_base = OTHER
                        note = 2'-O-methyl modified nucleotide
modified_base           10
                        mod_base = OTHER
                        note = 2'-fluoro modified nucleotide
modified_base           11
                        mod_base = OTHER
                        note = 2'-O-methyl modified nucleotide
modified_base           12
                        mod_base = OTHER
                        note = 2'-O-methyl modified nucleotide
modified_base           13
                        mod_base = OTHER
                        note = 2'-O-methyl modified nucleotide
modified_base           14
                        mod_base = OTHER
                        note = 2'-fluoro modified nucleotide
modified_base           15
                        mod_base = OTHER
                        note = 2'-O-methyl modified nucleotide
modified_base           16
                        mod_base = OTHER
                        note = 2'-O-methyl modified nucleotide
```

-continued

```
modified_base          17
                       mod_base = OTHER
                       note = 2'-O-methyl modified nucleotide
modified_base          18
                       mod_base = OTHER
                       note = 2'-O-methyl modified nucleotide
modified_base          19
                       mod_base = OTHER
                       note = 2'-O-methyl modified nucleotide
modified_base          20
                       mod_base = OTHER
                       note = 2'-O-methyl modified nucleotide, phosphorothioate
                        linkage
modified_base          21
                       mod_base = OTHER
                       note = 2'-O-methyl modified nucleotide, phosphorothioate
                        linkage
modified_base          22
                       mod_base = OTHER
                       note = 2'-O-methyl modified nucleotide
source                 1..22
                       mol_type = other RNA
                       organism = synthetic construct
SEQUENCE: 16
ttaggaaaca gcatattctt gg                                           22

SEQ ID NO: 17          moltype = RNA  length = 36
FEATURE                Location/Qualifiers
source                 1..36
                       mol_type = other RNA
                       organism = synthetic construct
SEQUENCE: 17
agggtttgtt tgtttcatta gcagccgaaa ggctgc                            36

SEQ ID NO: 18          moltype = RNA  length = 22
FEATURE                Location/Qualifiers
source                 1..22
                       mol_type = other RNA
                       organism = synthetic construct
SEQUENCE: 18
taatgaaaca aacaaaccct gg                                           22

SEQ ID NO: 19          moltype = RNA  length = 36
FEATURE                Location/Qualifiers
modified_base          1
                       mod_base = OTHER
                       note = C22 hydrocarbon chain, phosphorothioate linkage
modified_base          2
                       mod_base = OTHER
                       note = 2'-O-methyl modified nucleotide
modified_base          3
                       mod_base = OTHER
                       note = 2'-O-methyl modified nucleotide
modified_base          4
                       mod_base = OTHER
                       note = 2'-O-methyl modified nucleotide
modified_base          5
                       mod_base = OTHER
                       note = 2'-O-methyl modified nucleotide
modified_base          6
                       mod_base = OTHER
                       note = 2'-O-methyl modified nucleotide
modified_base          7
                       mod_base = OTHER
                       note = 2'-O-methyl modified nucleotide
modified_base          8
                       mod_base = OTHER
                       note = 2'-fluoro modified nucleotide
modified_base          9
                       mod_base = OTHER
                       note = 2'-fluoro modified nucleotide
modified_base          10
                       mod_base = OTHER
                       note = 2'-fluoro modified nucleotide
modified_base          11
                       mod_base = OTHER
                       note = 2'-fluoro modified nucleotide
modified_base          12
                       mod_base = OTHER
```

-continued

```
                     note = 2'-O-methyl modified nucleotide
modified_base        13
                     mod_base = OTHER
                     note = 2'-O-methyl modified nucleotide
modified_base        14
                     mod_base = OTHER
                     note = 2'-O-methyl modified nucleotide
modified_base        15
                     mod_base = OTHER
                     note = 2'-O-methyl modified nucleotide
modified_base        16
                     mod_base = OTHER
                     note = 2'-O-methyl modified nucleotide
modified_base        17
                     mod_base = OTHER
                     note = 2'-O-methyl modified nucleotide
modified_base        18
                     mod_base = OTHER
                     note = 2'-O-methyl modified nucleotide
modified_base        19
                     mod_base = OTHER
                     note = 2'-O-methyl modified nucleotide
modified_base        20
                     mod_base = OTHER
                     note = 2'-O-methyl modified nucleotide
modified_base        21
                     mod_base = OTHER
                     note = 2'-O-methyl modified nucleotide
modified_base        22
                     mod_base = OTHER
                     note = 2'-O-methyl modified nucleotide
modified_base        23
                     mod_base = OTHER
                     note = 2'-O-methyl modified nucleotide
modified_base        24
                     mod_base = OTHER
                     note = 2'-O-methyl modified nucleotide
modified_base        25
                     mod_base = OTHER
                     note = 2'-O-methyl modified nucleotide
modified_base        26
                     mod_base = OTHER
                     note = 2'-O-methyl modified nucleotide
modified_base        27
                     mod_base = OTHER
                     note = 2'-O-methyl modified nucleotide
modified_base        28
                     mod_base = OTHER
                     note = GalNAc (N-acetylgalactosamine) modification attached
                      to an adenine nucleotide
modified_base        29
                     mod_base = OTHER
                     note = GalNAc (N-acetylgalactosamine) modification attached
                      to an adenine nucleotide
modified_base        30
                     mod_base = OTHER
                     note = GalNAc (N-acetylgalactosamine) modification attached
                      to an adenine nucleotide
modified_base        31
                     mod_base = OTHER
                     note = 2'-O-methyl modified nucleotide
modified_base        32
                     mod_base = OTHER
                     note = 2'-O-methyl modified nucleotide
modified_base        33
                     mod_base = OTHER
                     note = 2'-O-methyl modified nucleotide
modified_base        34
                     mod_base = OTHER
                     note = 2'-O-methyl modified nucleotide
modified_base        35
                     mod_base = OTHER
                     note = 2'-O-methyl modified nucleotide
modified_base        36
                     mod_base = OTHER
                     note = 2'-O-methyl modified nucleotide
source               1..36
                     mol_type = other RNA
                     organism = synthetic construct
```

-continued

```
SEQUENCE: 19
agggtttgtt tgtttcatta gcagccgaaa ggctgc                              36

SEQ ID NO: 20           moltype = RNA  length = 22
FEATURE                 Location/Qualifiers
modified_base           1
                        mod_base = OTHER
                        note = 4'-O-monomethylphosphonate-2'-O-methyl modified
                         nucleotide
modified_base           2
                        mod_base = OTHER
                        note = 2'-fluoro modified nucleotide with a
                         phosphorothioate linkage
modified_base           3
                        mod_base = OTHER
                        note = 2'-fluoro modified nucleotide with a
                         phosphorothioate linkage
modified_base           4
                        mod_base = OTHER
                        note = 2'-fluoro modified nucleotide
modified_base           5
                        mod_base = OTHER
                        note = 2'-fluoro modified nucleotide
modified_base           6
                        mod_base = OTHER
                        note = 2'-O-methyl modified nucleotide
modified_base           7
                        mod_base = OTHER
                        note = 2'-fluoro modified nucleotide
modified_base           8
                        mod_base = OTHER
                        note = 2'-O-methyl modified nucleotide
modified_base           9
                        mod_base = OTHER
                        note = 2'-O-methyl modified nucleotide
modified_base           10
                        mod_base = OTHER
                        note = 2'-fluoro modified nucleotide
modified_base           11
                        mod_base = OTHER
                        note = 2'-O-methyl modified nucleotide
modified_base           12
                        mod_base = OTHER
                        note = 2'-O-methyl modified nucleotide
modified_base           13
                        mod_base = OTHER
                        note = 2'-O-methyl modified nucleotide
modified_base           14
                        mod_base = OTHER
                        note = 2'-fluoro modified nucleotide
modified_base           15
                        mod_base = OTHER
                        note = 2'-O-methyl modified nucleotide
modified_base           16
                        mod_base = OTHER
                        note = 2'-O-methyl modified nucleotide
modified_base           17
                        mod_base = OTHER
                        note = 2'-O-methyl modified nucleotide
modified_base           18
                        mod_base = OTHER
                        note = 2'-O-methyl modified nucleotide
modified_base           19
                        mod_base = OTHER
                        note = 2'-O-methyl modified nucleotide
modified_base           20
                        mod_base = OTHER
                        note = 2'-O-methyl modified nucleotide, phosphorothioate
                         linkage
modified_base           21
                        mod_base = OTHER
                        note = 2'-O-methyl modified nucleotide, phosphorothioate
                         linkage
modified_base           22
                        mod_base = OTHER
                        note = 2'-O-methyl modified nucleotide
source                  1..22
                        mol_type = other RNA
                        organism = synthetic construct
```

```
SEQUENCE: 20
taatgaaaca aacaaaccct gg                                          22

SEQ ID NO: 21          moltype = RNA  length = 36
FEATURE                Location/Qualifiers
source                 1..36
                       mol_type = other RNA
                       organism = synthetic construct
SEQUENCE: 21
cagaacatgg atctattaaa gcagccgaaa ggctgc                           36

SEQ ID NO: 22          moltype = RNA  length = 22
FEATURE                Location/Qualifiers
source                 1..22
                       mol_type = other RNA
                       organism = synthetic construct
SEQUENCE: 22
tttaatagat ccatgttctg gg                                          22

SEQ ID NO: 23          moltype = RNA  length = 36
FEATURE                Location/Qualifiers
modified_base          1
                       mod_base = OTHER
                       note = C22 hydrocarbon chain, phosphorothioate linkage
modified_base          2
                       mod_base = OTHER
                       note = 2'-O-methyl modified nucleotide
modified_base          3
                       mod_base = OTHER
                       note = 2'-O-methyl modified nucleotide
modified_base          4
                       mod_base = OTHER
                       note = 2'-O-methyl modified nucleotide
modified_base          5
                       mod_base = OTHER
                       note = 2'-O-methyl modified nucleotide
modified_base          6
                       mod_base = OTHER
                       note = 2'-O-methyl modified nucleotide
modified_base          7
                       mod_base = OTHER
                       note = 2'-O-methyl modified nucleotide
modified_base          8
                       mod_base = OTHER
                       note = 2'-fluoro modified nucleotide
modified_base          9
                       mod_base = OTHER
                       note = 2'-fluoro modified nucleotide
modified_base          10
                       mod_base = OTHER
                       note = 2'-fluoro modified nucleotide
modified_base          11
                       mod_base = OTHER
                       note = 2'-fluoro modified nucleotide
modified_base          12
                       mod_base = OTHER
                       note = 2'-O-methyl modified nucleotide
modified_base          13
                       mod_base = OTHER
                       note = 2'-O-methyl modified nucleotide
modified_base          14
                       mod_base = OTHER
                       note = 2'-O-methyl modified nucleotide
modified_base          15
                       mod_base = OTHER
                       note = 2'-O-methyl modified nucleotide
modified_base          16
                       mod_base = OTHER
                       note = 2'-O-methyl modified nucleotide
modified_base          17
                       mod_base = OTHER
                       note = 2'-O-methyl modified nucleotide
modified_base          18
                       mod_base = OTHER
                       note = 2'-O-methyl modified nucleotide
modified_base          19
                       mod_base = OTHER
                       note = 2'-O-methyl modified nucleotide
modified_base          20
```

-continued

```
                        mod_base = OTHER
                        note = 2'-O-methyl modified nucleotide
modified_base           21
                        mod_base = OTHER
                        note = 2'-O-methyl modified nucleotide
modified_base           22
                        mod_base = OTHER
                        note = 2'-O-methyl modified nucleotide
modified_base           23
                        mod_base = OTHER
                        note = 2'-O-methyl modified nucleotide
modified_base           24
                        mod_base = OTHER
                        note = 2'-O-methyl modified nucleotide
modified_base           25
                        mod_base = OTHER
                        note = 2'-O-methyl modified nucleotide
modified_base           26
                        mod_base = OTHER
                        note = 2'-O-methyl modified nucleotide
modified_base           27
                        mod_base = OTHER
                        note = 2'-O-methyl modified nucleotide
modified_base           28
                        mod_base = OTHER
                        note = GalNAc (N-acetylgalactosamine) modification attached
                         to an adenine nucleotide
modified_base           29
                        mod_base = OTHER
                        note = GalNAc (N-acetylgalactosamine) modification attached
                         to an adenine nucleotide
modified_base           30
                        mod_base = OTHER
                        note = GalNAc (N-acetylgalactosamine) modification attached
                         to an adenine nucleotide
modified_base           31
                        mod_base = OTHER
                        note = 2'-O-methyl modified nucleotide
modified_base           32
                        mod_base = OTHER
                        note = 2'-O-methyl modified nucleotide
modified_base           33
                        mod_base = OTHER
                        note = 2'-O-methyl modified nucleotide
modified_base           34
                        mod_base = OTHER
                        note = 2'-O-methyl modified nucleotide
modified_base           35
                        mod_base = OTHER
                        note = 2'-O-methyl modified nucleotide
modified_base           36
                        mod_base = OTHER
                        note = 2'-O-methyl modified nucleotide
source                  1..36
                        mol_type = other RNA
                        organism = synthetic construct
SEQUENCE: 23
cagaacatgg atctattaaa gcagccgaaa ggctgc                          36

SEQ ID NO: 24           moltype = RNA  length = 22
FEATURE                 Location/Qualifiers
modified_base           1
                        mod_base = OTHER
                        note = 4'-O-monomethylphosphonate-2'-O-methyl modified
                         nucleotide
modified_base           2
                        mod_base = OTHER
                        note = 2'-fluoro modified nucleotide with a
                         phosphorothioate linkage
modified_base           3
                        mod_base = OTHER
                        note = 2'-fluoro modified nucleotide with a
                         phosphorothioate linkage
modified_base           4
                        mod_base = OTHER
                        note = 2'-fluoro modified nucleotide
modified_base           5
                        mod_base = OTHER
                        note = 2'-fluoro modified nucleotide
```

```
modified_base         6
                      mod_base = OTHER
                      note = 2'-O-methyl modified nucleotide
modified_base         7
                      mod_base = OTHER
                      note = 2'-fluoro modified nucleotide
modified_base         8
                      mod_base = OTHER
                      note = 2'-O-methyl modified nucleotide
modified_base         9
                      mod_base = OTHER
                      note = 2'-O-methyl modified nucleotide
modified_base         10
                      mod_base = OTHER
                      note = 2'-fluoro modified nucleotide
modified_base         11
                      mod_base = OTHER
                      note = 2'-O-methyl modified nucleotide
modified_base         12
                      mod_base = OTHER
                      note = 2'-O-methyl modified nucleotide
modified_base         13
                      mod_base = OTHER
                      note = 2'-O-methyl modified nucleotide
modified_base         14
                      mod_base = OTHER
                      note = 2'-fluoro modified nucleotide
modified_base         15
                      mod_base = OTHER
                      note = 2'-O-methyl modified nucleotide
modified_base         16
                      mod_base = OTHER
                      note = 2'-O-methyl modified nucleotide
modified_base         17
                      mod_base = OTHER
                      note = 2'-O-methyl modified nucleotide
modified_base         18
                      mod_base = OTHER
                      note = 2'-O-methyl modified nucleotide
modified_base         19
                      mod_base = OTHER
                      note = 2'-O-methyl modified nucleotide
modified_base         20
                      mod_base = OTHER
                      note = 2'-O-methyl modified nucleotide, phosphorothioate
                       linkage
modified_base         21
                      mod_base = OTHER
                      note = 2'-O-methyl modified nucleotide, phosphorothioate
                       linkage
modified_base         22
                      mod_base = OTHER
                      note = 2'-O-methyl modified nucleotide
source                1..22
                      mol_type = other RNA
                      organism = synthetic construct
SEQUENCE: 24
tttaatagat ccatgttctg gg                                          22

SEQ ID NO: 25         moltype = RNA  length = 36
FEATURE               Location/Qualifiers
source                1..36
                      mol_type = other RNA
                      organism = synthetic construct
SEQUENCE: 25
catggatcta ttaaagtcaa gcagccgaaa ggctgc                           36

SEQ ID NO: 26         moltype = RNA  length = 22
FEATURE               Location/Qualifiers
source                1..22
                      mol_type = other RNA
                      organism = synthetic construct
SEQUENCE: 26
ttgactttaa tagatccatg gg                                          22

SEQ ID NO: 27         moltype = RNA  length = 36
FEATURE               Location/Qualifiers
modified_base         1
                      mod_base = OTHER
```

-continued

```
                        note = C22 hydrocarbon chain, phosphorothioate linkage
modified_base           2
                        mod_base = OTHER
                        note = 2'-O-methyl modified nucleotide
modified_base           3
                        mod_base = OTHER
                        note = 2'-O-methyl modified nucleotide
modified_base           4
                        mod_base = OTHER
                        note = 2'-O-methyl modified nucleotide
modified_base           5
                        mod_base = OTHER
                        note = 2'-O-methyl modified nucleotide
modified_base           6
                        mod_base = OTHER
                        note = 2'-O-methyl modified nucleotide
modified_base           7
                        mod_base = OTHER
                        note = 2'-O-methyl modified nucleotide
modified_base           8
                        mod_base = OTHER
                        note = 2'-fluoro modified nucleotide
modified_base           9
                        mod_base = OTHER
                        note = 2'-fluoro modified nucleotide
modified_base           10
                        mod_base = OTHER
                        note = 2'-fluoro modified nucleotide
modified_base           11
                        mod_base = OTHER
                        note = 2'-fluoro modified nucleotide
modified_base           12
                        mod_base = OTHER
                        note = 2'-O-methyl modified nucleotide
modified_base           13
                        mod_base = OTHER
                        note = 2'-O-methyl modified nucleotide
modified_base           14
                        mod_base = OTHER
                        note = 2'-O-methyl modified nucleotide
modified_base           15
                        mod_base = OTHER
                        note = 2'-O-methyl modified nucleotide
modified_base           16
                        mod_base = OTHER
                        note = 2'-O-methyl modified nucleotide
modified_base           17
                        mod_base = OTHER
                        note = 2'-O-methyl modified nucleotide
modified_base           18
                        mod_base = OTHER
                        note = 2'-O-methyl modified nucleotide
modified_base           19
                        mod_base = OTHER
                        note = 2'-O-methyl modified nucleotide
modified_base           20
                        mod_base = OTHER
                        note = 2'-O-methyl modified nucleotide
modified_base           21
                        mod_base = OTHER
                        note = 2'-O-methyl modified nucleotide
modified_base           22
                        mod_base = OTHER
                        note = 2'-O-methyl modified nucleotide
modified_base           23
                        mod_base = OTHER
                        note = 2'-O-methyl modified nucleotide
modified_base           24
                        mod_base = OTHER
                        note = 2'-O-methyl modified nucleotide
modified_base           25
                        mod_base = OTHER
                        note = 2'-O-methyl modified nucleotide
modified_base           26
                        mod_base = OTHER
                        note = 2'-O-methyl modified nucleotide
modified_base           27
                        mod_base = OTHER
                        note = 2'-O-methyl modified nucleotide
```

-continued

```
modified_base          28
                       mod_base = OTHER
                       note = GalNAc (N-acetylgalactosamine) modification attached
                        to an adenine nucleotide
modified_base          29
                       mod_base = OTHER
                       note = GalNAc (N-acetylgalactosamine) modification attached
                        to an adenine nucleotide
modified_base          30
                       mod_base = OTHER
                       note = GalNAc (N-acetylgalactosamine) modification attached
                        to an adenine nucleotide
modified_base          31
                       mod_base = OTHER
                       note = 2'-O-methyl modified nucleotide
modified_base          32
                       mod_base = OTHER
                       note = 2'-O-methyl modified nucleotide
modified_base          33
                       mod_base = OTHER
                       note = 2'-O-methyl modified nucleotide
modified_base          34
                       mod_base = OTHER
                       note = 2'-O-methyl modified nucleotide
modified_base          35
                       mod_base = OTHER
                       note = 2'-O-methyl modified nucleotide
modified_base          36
                       mod_base = OTHER
                       note = 2'-O-methyl modified nucleotide
source                 1..36
                       mol_type = other RNA
                       organism = synthetic construct
SEQUENCE: 27
catggatcta ttaaagtcaa gcagccgaaa ggctgc                            36

SEQ ID NO: 28          moltype = RNA  length = 22
FEATURE                Location/Qualifiers
modified_base          1
                       mod_base = OTHER
                       note = 4'-O-monomethylphosphonate-2'-O-methyl modified
                        nucleotide
modified_base          2
                       mod_base = OTHER
                       note = 2'-fluoro modified nucleotide with a
                        phosphorothioate linkage
modified_base          3
                       mod_base = OTHER
                       note = 2'-fluoro modified nucleotide with a
                        phosphorothioate linkage
modified_base          4
                       mod_base = OTHER
                       note = 2'-fluoro modified nucleotide
modified_base          5
                       mod_base = OTHER
                       note = 2'-fluoro modified nucleotide
modified_base          6
                       mod_base = OTHER
                       note = 2'-O-methyl modified nucleotide
modified_base          7
                       mod_base = OTHER
                       note = 2'-fluoro modified nucleotide
modified_base          8
                       mod_base = OTHER
                       note = 2'-O-methyl modified nucleotide
modified_base          9
                       mod_base = OTHER
                       note = 2'-O-methyl modified nucleotide
modified_base          10
                       mod_base = OTHER
                       note = 2'-fluoro modified nucleotide
modified_base          11
                       mod_base = OTHER
                       note = 2'-O-methyl modified nucleotide
modified_base          12
                       mod_base = OTHER
                       note = 2'-O-methyl modified nucleotide
modified_base          13
                       mod_base = OTHER
```

-continued

```
                        note = 2'-O-methyl modified nucleotide
modified_base           14
                        mod_base = OTHER
                        note = 2'-fluoro modified nucleotide
modified_base           15
                        mod_base = OTHER
                        note = 2'-O-methyl modified nucleotide
modified_base           16
                        mod_base = OTHER
                        note = 2'-O-methyl modified nucleotide
modified_base           17
                        mod_base = OTHER
                        note = 2'-O-methyl modified nucleotide
modified_base           18
                        mod_base = OTHER
                        note = 2'-O-methyl modified nucleotide
modified_base           19
                        mod_base = OTHER
                        note = 2'-O-methyl modified nucleotide
modified_base           20
                        mod_base = OTHER
                        note = 2'-O-methyl modified nucleotide, phosphorothioate
                         linkage
modified_base           21
                        mod_base = OTHER
                        note = 2'-O-methyl modified nucleotide, phosphorothioate
                         linkage
modified_base           22
                        mod_base = OTHER
                        note = 2'-O-methyl modified nucleotide
source                  1..22
                        mol_type = other RNA
                        organism = synthetic construct
SEQUENCE: 28
ttgactttaa tagatccatg gg                                             22

SEQ ID NO: 29           moltype = RNA  length = 16
FEATURE                 Location/Qualifiers
source                  1..16
                        mol_type = other RNA
                        organism = synthetic construct
SEQUENCE: 29
gcagccgaaa ggctgc                                                    16

SEQ ID NO: 30           moltype = RNA  length = 36
FEATURE                 Location/Qualifiers
modified_base           1
                        mod_base = OTHER
                        note = 2'-O-methyl modified nucleotide, phosphorothioate
                         linkage
modified_base           2
                        mod_base = OTHER
                        note = 2'-O-methyl modified nucleotide
modified_base           3
                        mod_base = OTHER
                        note = 2'-O-methyl modified nucleotide
modified_base           4
                        mod_base = OTHER
                        note = 2'-O-methyl modified nucleotide
modified_base           5
                        mod_base = OTHER
                        note = 2'-O-methyl modified nucleotide
modified_base           6
                        mod_base = OTHER
                        note = 2'-O-methyl modified nucleotide
modified_base           7
                        mod_base = OTHER
                        note = 2'-O-methyl modified nucleotide
modified_base           8
                        mod_base = OTHER
                        note = 2'-fluoro modified nucleotide
modified_base           9
                        mod_base = OTHER
                        note = 2'-fluoro modified nucleotide
modified_base           10
                        mod_base = OTHER
                        note = 2'-fluoro modified nucleotide
modified_base           11
                        mod_base = OTHER
```

-continued

```
                        note = 2'-fluoro modified nucleotide
modified_base           12
                        mod_base = OTHER
                        note = 2'-O-methyl modified nucleotide
modified_base           13
                        mod_base = OTHER
                        note = 2'-O-methyl modified nucleotide
modified_base           14
                        mod_base = OTHER
                        note = 2'-O-methyl modified nucleotide
modified_base           15
                        mod_base = OTHER
                        note = 2'-O-methyl modified nucleotide
modified_base           16
                        mod_base = OTHER
                        note = 2'-O-methyl modified nucleotide
modified_base           17
                        mod_base = OTHER
                        note = 2'-O-methyl modified nucleotide
modified_base           18
                        mod_base = OTHER
                        note = 2'-O-methyl modified nucleotide
modified_base           19
                        mod_base = OTHER
                        note = 2'-O-methyl modified nucleotide
modified_base           20
                        mod_base = OTHER
                        note = 2'-O-methyl modified nucleotide
modified_base           21
                        mod_base = OTHER
                        note = 2'-O-methyl modified nucleotide
modified_base           22
                        mod_base = OTHER
                        note = 2'-O-methyl modified nucleotide
modified_base           23
                        mod_base = OTHER
                        note = 2'-O-methyl modified nucleotide
modified_base           24
                        mod_base = OTHER
                        note = 2'-O-methyl modified nucleotide
modified_base           25
                        mod_base = OTHER
                        note = 2'-O-methyl modified nucleotide
modified_base           26
                        mod_base = OTHER
                        note = 2'-O-methyl modified nucleotide
modified_base           27
                        mod_base = OTHER
                        note = 2'-O-methyl modified nucleotide
modified_base           28
                        mod_base = OTHER
                        note = C22 hydrocarbon chain, phosphorothioate linkage
modified_base           29
                        mod_base = OTHER
                        note = 2'-O-methyl modified nucleotide
modified_base           30
                        mod_base = OTHER
                        note = 2'-O-methyl modified nucleotide
modified_base           31
                        mod_base = OTHER
                        note = 2'-O-methyl modified nucleotide
modified_base           32
                        mod_base = OTHER
                        note = 2'-O-methyl modified nucleotide
modified_base           33
                        mod_base = OTHER
                        note = 2'-O-methyl modified nucleotide
modified_base           34
                        mod_base = OTHER
                        note = 2'-O-methyl modified nucleotide
modified_base           35
                        mod_base = OTHER
                        note = 2'-O-methyl modified nucleotide
modified_base           36
                        mod_base = OTHER
                        note = 2'-O-methyl modified nucleotide
source                  1..36
                        mol_type = other RNA
                        organism = synthetic construct
```

-continued

```
SEQUENCE: 30
agataggcat tgaaatgaaa gcagccgaaa ggctgc                          36

SEQ ID NO: 31           moltype = RNA  length = 22
FEATURE                 Location/Qualifiers
modified_base           1
                        mod_base = OTHER
                        note = 4'-O-monomethylphosphonate-2'-O-methyl modified
                         nucleotide
modified_base           2
                        mod_base = OTHER
                        note = 2'-fluoro modified nucleotide with a
                         phosphorothioate linkage
modified_base           3
                        mod_base = OTHER
                        note = 2'-fluoro modified nucleotide with a
                         phosphorothioate linkage
modified_base           4
                        mod_base = OTHER
                        note = 2'-fluoro modified nucleotide
modified_base           5
                        mod_base = OTHER
                        note = 2'-fluoro modified nucleotide
modified_base           6
                        mod_base = OTHER
                        note = 2'-O-methyl modified nucleotide
modified_base           7
                        mod_base = OTHER
                        note = 2'-fluoro modified nucleotide
modified_base           8
                        mod_base = OTHER
                        note = 2'-O-methyl modified nucleotide
modified_base           9
                        mod_base = OTHER
                        note = 2'-O-methyl modified nucleotide
modified_base           10
                        mod_base = OTHER
                        note = 2'-fluoro modified nucleotide
modified_base           11
                        mod_base = OTHER
                        note = 2'-O-methyl modified nucleotide
modified_base           12
                        mod_base = OTHER
                        note = 2'-O-methyl modified nucleotide
modified_base           13
                        mod_base = OTHER
                        note = 2'-O-methyl modified nucleotide
modified_base           14
                        mod_base = OTHER
                        note = 2'-fluoro modified nucleotide
modified_base           15
                        mod_base = OTHER
                        note = 2'-O-methyl modified nucleotide
modified_base           16
                        mod_base = OTHER
                        note = 2'-O-methyl modified nucleotide
modified_base           17
                        mod_base = OTHER
                        note = 2'-O-methyl modified nucleotide
modified_base           18
                        mod_base = OTHER
                        note = 2'-O-methyl modified nucleotide
modified_base           19
                        mod_base = OTHER
                        note = 2'-O-methyl modified nucleotide
modified_base           20
                        mod_base = OTHER
                        note = 2'-O-methyl modified nucleotide, phosphorothioate
                         linkage
modified_base           21
                        mod_base = OTHER
                        note = 2'-O-methyl modified nucleotide, phosphorothioate
                         linkage
modified_base           22
                        mod_base = OTHER
                        note = 2'-O-methyl modified nucleotide
source                  1..22
                        mol_type = other RNA
                        organism = synthetic construct
```

-continued

```
SEQUENCE: 31
tttcatttca atgcctatct gg                                          22

SEQ ID NO: 32           moltype = RNA  length = 36
FEATURE                 Location/Qualifiers
modified_base           1
                        mod_base = OTHER
                        note = 2'-O-methyl modified nucleotide, phosphorothioate
                         linkage
modified_base           2
                        mod_base = OTHER
                        note = 2'-O-methyl modified nucleotide
modified_base           3
                        mod_base = OTHER
                        note = 2'-O-methyl modified nucleotide
modified_base           4
                        mod_base = OTHER
                        note = 2'-O-methyl modified nucleotide
modified_base           5
                        mod_base = OTHER
                        note = 2'-O-methyl modified nucleotide
modified_base           6
                        mod_base = OTHER
                        note = 2'-O-methyl modified nucleotide
modified_base           7
                        mod_base = OTHER
                        note = 2'-O-methyl modified nucleotide
modified_base           8
                        mod_base = OTHER
                        note = 2'-fluoro modified nucleotide
modified_base           9
                        mod_base = OTHER
                        note = 2'-fluoro modified nucleotide
modified_base           10
                        mod_base = OTHER
                        note = 2'-fluoro modified nucleotide
modified_base           11
                        mod_base = OTHER
                        note = 2'-fluoro modified nucleotide
modified_base           12
                        mod_base = OTHER
                        note = 2'-O-methyl modified nucleotide
modified_base           13
                        mod_base = OTHER
                        note = 2'-O-methyl modified nucleotide
modified_base           14
                        mod_base = OTHER
                        note = 2'-O-methyl modified nucleotide
modified_base           15
                        mod_base = OTHER
                        note = 2'-O-methyl modified nucleotide
modified_base           16
                        mod_base = OTHER
                        note = 2'-O-methyl modified nucleotide
modified_base           17
                        mod_base = OTHER
                        note = 2'-O-methyl modified nucleotide
modified_base           18
                        mod_base = OTHER
                        note = 2'-O-methyl modified nucleotide
modified_base           19
                        mod_base = OTHER
                        note = 2'-O-methyl modified nucleotide
modified_base           20
                        mod_base = OTHER
                        note = 2'-O-methyl modified nucleotide
modified_base           21
                        mod_base = OTHER
                        note = 2'-O-methyl modified nucleotide
modified_base           22
                        mod_base = OTHER
                        note = 2'-O-methyl modified nucleotide
modified_base           23
                        mod_base = OTHER
                        note = 2'-O-methyl modified nucleotide
modified_base           24
                        mod_base = OTHER
                        note = 2'-O-methyl modified nucleotide
modified_base           25
```

```
                         mod_base = OTHER
                         note = 2'-O-methyl modified nucleotide
modified_base            26
                         mod_base = OTHER
                         note = 2'-O-methyl modified nucleotide
modified_base            27
                         mod_base = OTHER
                         note = 2'-O-methyl modified nucleotide
modified_base            28
                         mod_base = OTHER
                         note = GalNAc (N-acetylgalactosamine) modification attached
                          to an adenine nucleotide
modified_base            29
                         mod_base = OTHER
                         note = GalNAc (N-acetylgalactosamine) modification attached
                          to an adenine nucleotide
modified_base            30
                         mod_base = OTHER
                         note = GalNAc (N-acetylgalactosamine) modification attached
                          to an adenine nucleotide
modified_base            31
                         mod_base = OTHER
                         note = 2'-O-methyl modified nucleotide
modified_base            32
                         mod_base = OTHER
                         note = 2'-O-methyl modified nucleotide
modified_base            33
                         mod_base = OTHER
                         note = 2'-O-methyl modified nucleotide
modified_base            34
                         mod_base = OTHER
                         note = 2'-O-methyl modified nucleotide
modified_base            35
                         mod_base = OTHER
                         note = 2'-O-methyl modified nucleotide
modified_base            36
                         mod_base = OTHER
                         note = 2'-O-methyl modified nucleotide
source                   1..36
                         mol_type = other RNA
                         organism = synthetic construct
SEQUENCE: 32
agataggcat tgaaatgaaa gcagccgaaa ggctgc                              36

SEQ ID NO: 33            moltype = RNA  length = 22
FEATURE                  Location/Qualifiers
modified_base            1
                         mod_base = OTHER
                         note = 4'-O-monomethylphosphonate-2'-O-methyl modified
                          nucleotide
modified_base            2
                         mod_base = OTHER
                         note = 2'-fluoro modified nucleotide with a
                          phosphorothioate linkage
modified_base            3
                         mod_base = OTHER
                         note = 2'-fluoro modified nucleotide
modified_base            4
                         mod_base = OTHER
                         note = 2'-fluoro modified nucleotide
modified_base            5
                         mod_base = OTHER
                         note = 2'-fluoro modified nucleotide
modified_base            6
                         mod_base = OTHER
                         note = 2'-O-methyl modified nucleotide
modified_base            7
                         mod_base = OTHER
                         note = 2'-fluoro modified nucleotide
modified_base            8
                         mod_base = OTHER
                         note = 2'-O-methyl modified nucleotide
modified_base            9
                         mod_base = OTHER
                         note = 2'-O-methyl modified nucleotide
modified_base            10
                         mod_base = OTHER
                         note = 2'-fluoro modified nucleotide
modified_base            11
```

-continued

```
                        mod_base = OTHER
                        note = 2'-O-methyl modified nucleotide
modified_base           12
                        mod_base = OTHER
                        note = 2'-O-methyl modified nucleotide
modified_base           13
                        mod_base = OTHER
                        note = 2'-O-methyl modified nucleotide
modified_base           14
                        mod_base = OTHER
                        note = 2'-fluoro modified nucleotide
modified_base           15
                        mod_base = OTHER
                        note = 2'-O-methyl modified nucleotide
modified_base           16
                        mod_base = OTHER
                        note = 2'-O-methyl modified nucleotide
modified_base           17
                        mod_base = OTHER
                        note = 2'-O-methyl modified nucleotide
modified_base           18
                        mod_base = OTHER
                        note = 2'-O-methyl modified nucleotide
modified_base           19
                        mod_base = OTHER
                        note = 2'-O-methyl modified nucleotide
modified_base           20
                        mod_base = OTHER
                        note = 2'-O-methyl modified nucleotide, phosphorothioate
                         linkage
modified_base           21
                        mod_base = OTHER
                        note = 2'-O-methyl modified nucleotide, phosphorothioate
                         linkage
modified_base           22
                        mod_base = OTHER
                        note = 2'-O-methyl modified nucleotide
source                  1..22
                        mol_type = other RNA
                        organism = synthetic construct
SEQUENCE: 33
tttcatttca atgcctatct gg                                            22

SEQ ID NO: 34           moltype = RNA  length = 36
FEATURE                 Location/Qualifiers
modified_base           1
                        mod_base = OTHER
                        note = C22 hydrocarbon chain, phosphorothioate linkage
modified_base           2
                        mod_base = OTHER
                        note = 2'-O-methyl modified nucleotide
modified_base           3
                        mod_base = OTHER
                        note = 2'-O-methyl modified nucleotide
modified_base           4
                        mod_base = OTHER
                        note = 2'-O-methyl modified nucleotide
modified_base           5
                        mod_base = OTHER
                        note = 2'-O-methyl modified nucleotide
modified_base           6
                        mod_base = OTHER
                        note = 2'-O-methyl modified nucleotide
modified_base           7
                        mod_base = OTHER
                        note = 2'-O-methyl modified nucleotide
modified_base           8
                        mod_base = OTHER
                        note = 2'-fluoro modified nucleotide
modified_base           9
                        mod_base = OTHER
                        note = 2'-fluoro modified nucleotide
modified_base           10
                        mod_base = OTHER
                        note = 2'-fluoro modified nucleotide
modified_base           11
                        mod_base = OTHER
                        note = 2'-fluoro modified nucleotide
modified_base           12
```

-continued

```
                      mod_base = OTHER
                      note = 2'-O-methyl modified nucleotide
modified_base         13
                      mod_base = OTHER
                      note = 2'-O-methyl modified nucleotide
modified_base         14
                      mod_base = OTHER
                      note = 2'-O-methyl modified nucleotide
modified_base         15
                      mod_base = OTHER
                      note = 2'-O-methyl modified nucleotide
modified_base         16
                      mod_base = OTHER
                      note = 2'-O-methyl modified nucleotide
modified_base         17
                      mod_base = OTHER
                      note = 2'-O-methyl modified nucleotide
modified_base         18
                      mod_base = OTHER
                      note = 2'-O-methyl modified nucleotide
modified_base         19
                      mod_base = OTHER
                      note = 2'-O-methyl modified nucleotide
modified_base         20
                      mod_base = OTHER
                      note = 2'-O-methyl modified nucleotide
modified_base         21
                      mod_base = OTHER
                      note = 2'-O-methyl modified nucleotide
modified_base         22
                      mod_base = OTHER
                      note = 2'-O-methyl modified nucleotide
modified_base         23
                      mod_base = OTHER
                      note = 2'-O-methyl modified nucleotide
modified_base         24
                      mod_base = OTHER
                      note = 2'-O-methyl modified nucleotide
modified_base         25
                      mod_base = OTHER
                      note = 2'-O-methyl modified nucleotide
modified_base         26
                      mod_base = OTHER
                      note = 2'-O-methyl modified nucleotide
modified_base         27
                      mod_base = OTHER
                      note = 2'-O-methyl modified nucleotide
modified_base         28
                      mod_base = OTHER
                      note = GalNAc (N-acetylgalactosamine) modification attached
                       to an adenine nucleotide
modified_base         29
                      mod_base = OTHER
                      note = GalNAc (N-acetylgalactosamine) modification attached
                       to an adenine nucleotide
modified_base         30
                      mod_base = OTHER
                      note = GalNAc (N-acetylgalactosamine) modification attached
                       to an adenine nucleotide
modified_base         31
                      mod_base = OTHER
                      note = 2'-O-methyl modified nucleotide
modified_base         32
                      mod_base = OTHER
                      note = 2'-O-methyl modified nucleotide
modified_base         33
                      mod_base = OTHER
                      note = 2'-O-methyl modified nucleotide
modified_base         34
                      mod_base = OTHER
                      note = 2'-O-methyl modified nucleotide
modified_base         35
                      mod_base = OTHER
                      note = 2'-O-methyl modified nucleotide
modified_base         36
                      mod_base = OTHER
                      note = 2'-O-methyl modified nucleotide
source                1..36
                      mol_type = other RNA
```

-continued

```
                         organism = synthetic construct
SEQUENCE: 34
agataggcat tgaaatgaaa gcagccgaaa ggctgc                            36

SEQ ID NO: 35            moltype = RNA  length = 22
FEATURE                  Location/Qualifiers
modified_base            1
                         mod_base = OTHER
                         note = 4'-O-monomethylphosphonate-2'-O-methyl modified
                          nucleotide
modified_base            2
                         mod_base = OTHER
                         note = 2'-fluoro modified nucleotide with a
                          phosphorothioate linkage
modified_base            3
                         mod_base = OTHER
                         note = 2'-fluoro modified nucleotide with a
                          phosphorothioate linkage
modified_base            4
                         mod_base = OTHER
                         note = 2'-fluoro modified nucleotide
modified_base            5
                         mod_base = OTHER
                         note = 2'-fluoro modified nucleotide
modified_base            6
                         mod_base = OTHER
                         note = 2'-O-methyl modified nucleotide
modified_base            7
                         mod_base = OTHER
                         note = 2'-fluoro modified nucleotide
modified_base            8
                         mod_base = OTHER
                         note = 2'-O-methyl modified nucleotide
modified_base            9
                         mod_base = OTHER
                         note = 2'-O-methyl modified nucleotide
modified_base            10
                         mod_base = OTHER
                         note = 2'-fluoro modified nucleotide
modified_base            11
                         mod_base = OTHER
                         note = 2'-O-methyl modified nucleotide
modified_base            12
                         mod_base = OTHER
                         note = 2'-O-methyl modified nucleotide
modified_base            13
                         mod_base = OTHER
                         note = 2'-O-methyl modified nucleotide
modified_base            14
                         mod_base = OTHER
                         note = 2'-fluoro modified nucleotide
modified_base            15
                         mod_base = OTHER
                         note = 2'-O-methyl modified nucleotide
modified_base            16
                         mod_base = OTHER
                         note = 2'-O-methyl modified nucleotide
modified_base            17
                         mod_base = OTHER
                         note = 2'-O-methyl modified nucleotide
modified_base            18
                         mod_base = OTHER
                         note = 2'-O-methyl modified nucleotide
modified_base            19
                         mod_base = OTHER
                         note = 2'-O-methyl modified nucleotide
modified_base            20
                         mod_base = OTHER
                         note = 2'-O-methyl modified nucleotide, phosphorothioate
                          linkage
modified_base            21
                         mod_base = OTHER
                         note = 2'-O-methyl modified nucleotide, phosphorothioate
                          linkage
modified_base            22
                         mod_base = OTHER
                         note = 2'-O-methyl modified nucleotide
source                   1..22
                         mol_type = other RNA
```

-continued

```
                        organism = synthetic construct
SEQUENCE: 35
tttcatttca atgcctatct gg                                              22
```